(12) United States Patent
Brentano et al.

(10) Patent No.: US 10,724,085 B2
(45) Date of Patent: *Jul. 28, 2020

(54) METHODS AND COMPOSITIONS FOR NUCLEIC ACID AMPLIFICATION

(71) Applicant: GEN-PROBE INCORPORATED, San Diego, CA (US)

(72) Inventors: Steven T. Brentano, Santee, CA (US); Dmitry Lyakhov, San Diego, CA (US); Norman C. Nelson, San Diego, CA (US); James D. Carlson, San Diego, CA (US); Michael M. Becker, San Diego, CA (US); Lyle J. Arnold, Jr., Poway, CA (US)

(*) Notice: Subject to any disclaimer, the term of this patent is extended or adjusted under 35 U.S.C. 154(b) by 263 days.

This patent is subject to a terminal disclaimer.

(21) Appl. No.: 15/902,819

(22) Filed: Feb. 22, 2018

(65) Prior Publication Data

US 2018/0208981 A1    Jul. 26, 2018

Related U.S. Application Data

(60) Continuation of application No. 15/058,702, filed on Mar. 2, 2016, now Pat. No. 10,119,163, which is a division of application No. 13/956,158, filed on Jul. 31, 2013, now Pat. No. 9,399,796, which is a division of application No. 12/828,676, filed on Jul. 1, 2010, now Pat. No. 8,512,955.

(60) Provisional application No. 61/222,150, filed on Jul. 1, 2009.

(51) Int. Cl.
*C12Q 1/68* (2018.01)
*C12Q 1/6865* (2018.01)
*C12Q 1/6848* (2018.01)
*C12Q 1/6844* (2018.01)
*C12Q 1/6853* (2018.01)

(52) U.S. Cl.
CPC ........ *C12Q 1/6865* (2013.01); *C12Q 1/6844* (2013.01); *C12Q 1/6848* (2013.01); *C12Q 1/6853* (2013.01)

(58) Field of Classification Search
None
See application file for complete search history.

(56) References Cited

U.S. PATENT DOCUMENTS

| | | | |
|---|---|---|---|
| 4,800,159 A | 1/1989 | Mullis et al. | |
| 5,104,792 A | 4/1992 | Silver et al. | |
| 5,422,252 A | 6/1995 | Walker et al. | |
| 5,442,252 A | 8/1995 | Golz | |
| 5,582,989 A | 12/1996 | Caskey et al. | |
| 5,624,825 A | 4/1997 | Walker et al. | |
| 5,736,365 A | 4/1998 | Walker et al. | |
| 5,837,501 A | 11/1998 | Beumer et al. | |
| 5,882,856 A | 3/1999 | Shuber | |
| 6,027,889 A | 2/2000 | Barany et al. | |
| 6,090,558 A | 7/2000 | Butler et al. | |
| 6,207,372 B1 | 3/2001 | Shuber | |
| 6,251,639 B1 | 6/2001 | Kurn | |
| 6,270,967 B1 | 8/2001 | Whitcombe et al. | |
| 6,361,945 B1 | 3/2002 | Becker et al. | |
| 6,365,729 B1 | 4/2002 | Tyagi et al. | |
| 6,514,706 B1 | 2/2003 | Von Kalle et al. | |
| 6,585,938 B1 | 6/2003 | Su et al. | |
| 6,605,451 B1* | 8/2003 | Marmaro ............ | C12Q 1/6844 435/91.2 |
| 6,618,679 B2 | 9/2003 | Loehrlein et al. | |
| 6,638,722 B2 | 10/2003 | Ji et al. | |
| 6,686,156 B2 | 2/2004 | Kurn | |
| 6,737,253 B1 | 5/2004 | Tillet | |
| 6,797,470 B2 | 9/2004 | Barany et al. | |
| 6,808,888 B2 | 10/2004 | Zhang et al. | |
| 6,812,005 B2 | 11/2004 | Fan et al. | |
| 6,828,098 B2 | 12/2004 | Langmore et al. | |
| 6,844,155 B2 | 1/2005 | Shuber | |
| 6,890,741 B2 | 5/2005 | Fan et al. | |
| 6,942,974 B2 | 9/2005 | Brevnov | |
| 7,041,481 B2 | 5/2006 | Anderson et al. | |

(Continued)

FOREIGN PATENT DOCUMENTS

| EP | 0 408 295 A2 | 1/1919 |
|---|---|---|
| EP | 0201184 B2 | 12/1992 |

(Continued)

OTHER PUBLICATIONS

USPTO Non-Final Office Action, U.S. Appl. No. 12/828,676, dated Aug. 2, 2012.
USPTO Final Office Action, U.S. Appl. No. 12/828,676, dated Jan. 31, 2013.
UPTO Notice of Allowance, U.S. Appl. No. 12/828,676, dated Apr. 19, 2013.
USPTO Non-Final Office Action, U.S. Appl. No. 13/956,158, dated Jun. 16, 2015.
USPTO Final Office Action, U.S. Appl. No. 13/956,158, dated Nov. 3, 2015.

(Continued)

*Primary Examiner* — Stephanie K Mummert
(74) *Attorney, Agent, or Firm* — Nicholas V. Sherbina; Jeffrey E. Landes

(57) ABSTRACT

Compositions, reaction mixtures, and methods for performing an amplification reaction, including multiplex amplification reaction, wherein the method comprises using one or more amplification oligomer complexes comprising linked first and second amplification oligomer members. In one aspect, the amplification oligomer complex is hybridized to a target nucleic acid, the target nucleic acid with hybridized amplification oligomer complex is then captured, and other components are washed away. Target sequences of the target nucleic acids are pre-amplified to generate a first amplification product. The first amplification product is amplified in one or more secondary amplification reactions to generate second amplification products.

20 Claims, 15 Drawing Sheets

Specification includes a Sequence Listing.

(56) References Cited

U.S. PATENT DOCUMENTS

| | | | |
|---|---|---|---|
| 7,087,414 | B2 | 8/2006 | Gerdes et al. |
| 7,105,318 | B2 | 9/2006 | Kessler et al. |
| 7,153,658 | B2 | 12/2006 | Anderson et al. |
| 7,176,002 | B2 | 2/2007 | Lao et al. |
| 7,348,164 | B2 | 3/2008 | Andrus et al. |
| 7,402,386 | B2 | 7/2008 | Kum et al. |
| 7,432,055 | B2 | 10/2008 | Pemov et al. |
| 7,482,119 | B2 | 1/2009 | Parker et al. |
| 7,513,656 | B2 | 4/2009 | Park et al. |
| 7,537,886 | B1 | 5/2009 | Nazarenko et al. |
| 7,615,351 | B2 | 11/2009 | McMaster et al. |
| 8,198,027 | B2 | 6/2012 | Brentano et al. |
| 2002/0119533 | A1 | 8/2002 | Brown |
| 2002/0160361 | A1 | 10/2002 | Loehrlein et al. |
| 2003/0104421 | A1 | 6/2003 | Colangelo et al. |
| 2003/0152925 | A1 | 8/2003 | Chun |
| 2003/0165859 | A1 | 9/2003 | Nazarenko et al. |
| 2003/0204322 | A1 | 10/2003 | Loehrlein et al. |
| 2004/0014129 | A1 | 1/2004 | Brown |
| 2004/0091879 | A1 | 5/2004 | Nolan et al. |
| 2004/0132050 | A1 | 7/2004 | Monforte |
| 2004/0175733 | A1 | 9/2004 | Anderson et al. |
| 2004/0248102 | A1 | 12/2004 | Ilsley-Tyree et al. |
| 2004/0259116 | A1 | 12/2004 | Beckman et al. |
| 2005/0079520 | A1 | 4/2005 | Wu |
| 2005/0170373 | A1 | 8/2005 | Monforte |
| 2005/0196760 | A1 | 9/2005 | Pemov et al. |
| 2005/0227263 | A1 | 10/2005 | Green |
| 2005/0233363 | A1 | 10/2005 | Harding et al. |
| 2005/0250146 | A1 | 11/2005 | McMillan |
| 2006/0029954 | A1 | 2/2006 | Lao |
| 2006/0046265 | A1 | 3/2006 | Becker et al. |
| 2006/0141518 | A1 | 6/2006 | Lao et al. |
| 2006/0177844 | A1 | 8/2006 | Ching et al. |
| 2006/0281108 | A1 | 12/2006 | Monforte et al. |
| 2007/0134652 | A1 | 6/2007 | Slepnev et al. |
| 2007/0141575 | A1 | 6/2007 | Han |
| 2007/0077570 | A1 | 7/2007 | Lao et al. |
| 2007/0281317 | A1 | 12/2007 | Becker et al. |
| 2008/0050724 | A1 | 1/2008 | Devitt |
| 2008/0176294 | A1 | 7/2008 | Deiman et al. |
| 2011/0003305 | A1 | 1/2011 | Bretano et al. |

FOREIGN PATENT DOCUMENTS

| | | |
|---|---|---|
| EP | 1 659 187 A2 | 5/2006 |
| WO | 89/06700 A1 | 7/1989 |
| WO | 88/10315 A1 | 12/1989 |
| WO | 91/15601 A1 | 10/1991 |
| WO | 98/50583 A1 | 11/1998 |
| WO | 00/00638 A2 | 1/2000 |
| WO | 2001/094634 A2 | 12/2001 |
| WO | 2002/020845 A2 | 3/2002 |
| WO | 2005/019479 A1 | 3/2005 |
| WO | 2006/121997 A2 | 11/2006 |
| WO | 2007/025340 A1 | 3/2007 |
| WO | 2008/016988 A1 | 2/2008 |
| WO | 2008024493 A2 | 2/2008 |
| WO | 2008/055691 A1 | 5/2008 |
| WO | 2008/080029 A2 | 7/2008 |
| WO | WO-2008080029 A2 * | 7/2008 ........... C12Q 1/6834 |
| WO | 2008/108843 A2 | 9/2008 |

OTHER PUBLICATIONS

USPTO Notice of Allowance, U.S. Appl. No. 13/956,158, dated Mar. 4, 2016.
USPTO Non-Final Office Action, U.S. Appl. No. 15/058,702, dated Apr. 21, 2017.
USPTO Final Office Action, U.S. Appl. No. 15/058,702, dated Sep. 15, 2017.
USPTO Notice of Allowance, U.S. Appl. No. 15/058,702, dated Nov. 27, 2017.
USPTO Non-Final Rejection, U.S. Appl. No. 15/058,702, dated Mar. 2, 2018.
APO Patent Examination Report No. 1, Australian Patent Application No. 2010266234, dated Jan. 22, 2013.
CIPO Exam Report, Canadian Patent Application No. 2,766,391, dated Mar. 30, 2015.
CIPO Office Action, Canadian Patent Application No. 2,766,391, dated May 12, 2016.
CIPO Notice of Allowance, Canadian Patent Application No. 2,766,391, dated Nov. 17, 2016.
EPO Communication Pursuant to Article 94(3) EPC, European Patent Application No. 10730334.9, dated Oct. 25, 2012.
EPO Communication Pursuant to Article 94(3) EPC, European Patent Application No. 10730334.9, dated Sep. 4, 2013.
EPO Communication Pursuant to Article 94(3) EPC, European Patent Application No. 10730334.9, dated Aug. 20, 2014.
EPO Communication Under Rule 71(3) EPC, European Patent Application No. 10730334.9, dated Dec. 16, 2014.
PCT International Preliminary Report on Patentability, International Application No. PCT/US2010/040819, dated Jan. 4, 2012.
PCT Written Opinion, International Application No. PCT/US2010/040819, dated Oct. 21, 2010.
PCT International Search Report, International Application No. PCT/US2010/040819, dated Oct. 21, 2010.
Bustin, "Absolute quantification of mRNA using real-time reverse transcription polymerase chain reaction assays," Journal of Molecular Endocrinology, 2000, 25, 169-193.
Camilla et al., "Flow Cytometric Microsphere-Based Immunoassay: Analysis of Secreted Cytokines in Wholed-Blood Samples from Asthamtics," Clinical and Diagnostics Laboratory Immunology, 2001, vol. 8, No. 4, 776-784.
Casas et al., "Evaluation of Different Amplification Protocols for Use in Primer-Extension Preamplification," BioTechniques, 1996, 219-225.
Denning et al., "A molecular expression signature distinguishing follicular lesions in thyroid carcinoma using preamplification RT-PCR in archival samples," Modern Pathology, 2007, 1095-1102.
Feray et al., "Reinfection of Liver Graft by Hepatitis C Virus after Liver Transplantation," The American Society for Clinical Investigation, Inc., 1992, vol. 89, 1361-1365.
Gill et al., "Nucleic Acid Isothermal Aplification Technologies—A review," Taylor & Francis Group, LLC, 2008, vol. 27, No. 3, 224-243.
Hamelin et al., "Identification of Root Rot Fungi in Nursery Seedlings by Nested Multiplex PCR," Applied and Environmental Microbiology, 1996, vol. 62, No. 11, 4026-4031.
Jayaraman et al., "A PCR-Mediated Gene Synthesis Strategy Involving the Assembly of Oligonucleotides Representing Only One of the Strands," BioTechniques, 1992, vol. 12, No. 3, 392-398.
Johnson et al., "Structure of the cDNA Encoding Transcobalamin I, a Neutrophil Granule Protein," The Journal of Biological Chemistry, 1989, vol. 264, No. 27, 17754-17757.
Koehler et al., "Multiple Molecular Analyses From Minimal Cell Quantities by Sequential Isolation and Preamplification of DNA and RNA," Diagn. Mol. Pathol., vol. 16, No. 3, 2007, 141-146.
Li et al., "Multiplex co-amlification of 24 retinoblastoma gene exons after pre-amplification by long-distance PCR," Nucleic Acids Research, 1996, vol. 24, No. 3, 538-539.
Lin et al., "Correction of the N-Terminal Sequences of the Human Plastin Isoforms by Using Anchored Ploymerase Chain Reaction: Identification of a Potential Calcium-Binding Domain," Molecular and Cellular Biology, 1990, vol. 10, No. 4, 1818-1821.
Mullis et al., "Specific Enzymatic Amplification of DNA In Vitro: The Ploymerase Chain Reaction," Cold Spring Harbor Symposia on Quantitative Biology, 1986, 263-273.
Mullis et al., "Specific Synthesis of DNA in Vitro via a Plomerase-Catalyzed Chain Reaction," Methods in Enzymology, 1987, vol. 155, No. 21, 335-350.
Peixoto et al., "Quantification of Multiple Gene Expression in Individual Cells," Genome Research, 2004, 1938-1947, vol. 14, Cold Spring Harbor Laboratory Press, NY USA.
Persing et al., "Detection of Babesia microti by Polymerase Chain Reaction," J. Clin. Microbiol, 1992, vol. 30, No. 8, 2097-2103, American Society for Microbiology, Washington, D.C.

(56) References Cited

OTHER PUBLICATIONS

Ruano et al., "Biphasic Amplification of Very Dilute DNA Samples via 'Booster' PCR," Nucleic Acids Research, 1989, vol. 17, 5407 Oxford University Press, Oxford, UK.

Ruano et al., "Haplotype of Multiple Polymorphins Resolved by Enzymatic Amplification of Single DNA Molecules," Genetics, 1990, vol. 87, 6296-6300, Proc. Natl. Acad. Sci., USA.

Ruano et al., "Coupled Amplification and Sequencing of Genomic DBA," Genetics, 1991, vol. 88, 2815-2819, Proc. Natl. Acad. Sci., USA.

Shuber et al., "A Simplified Procedure for Developing Multiplex PCRs." Genome Research-Simplified Method for Multiplex PCR Development, 1995, vol. 5, 488-493, Cold Spring Harbor Laboratory, NY USA.

Simmonds et al., "Detection and Sequencing of Individual Molecules of HIV DNA Amplified by a Modified PCR," International Conf. AIDS, 1989, T.C.P. 92, p. 582.

Van Geldr et al., "Amplified RNA Synthesized From Limited Quatities of Heterogeneous cDNA," Biochemistry, 1990, vol. 87, 1663-1667, Proc. Natl. Acad. Sci., USA.

Zhang et al., "Whole Genome Amplification From a Single Cell: Implications for Genetic Analysis," Genetics, 1992, vol. 89, 5847-5851, Proc. Natl. Acad. Sci., USA.

\* cited by examiner

1. TCR containing TSU primers & capture probes

2. Mix with Sample that contains Target

3. Retrieve the captured target and TSU primer complex

4. Discard unbound TSU primer complexes

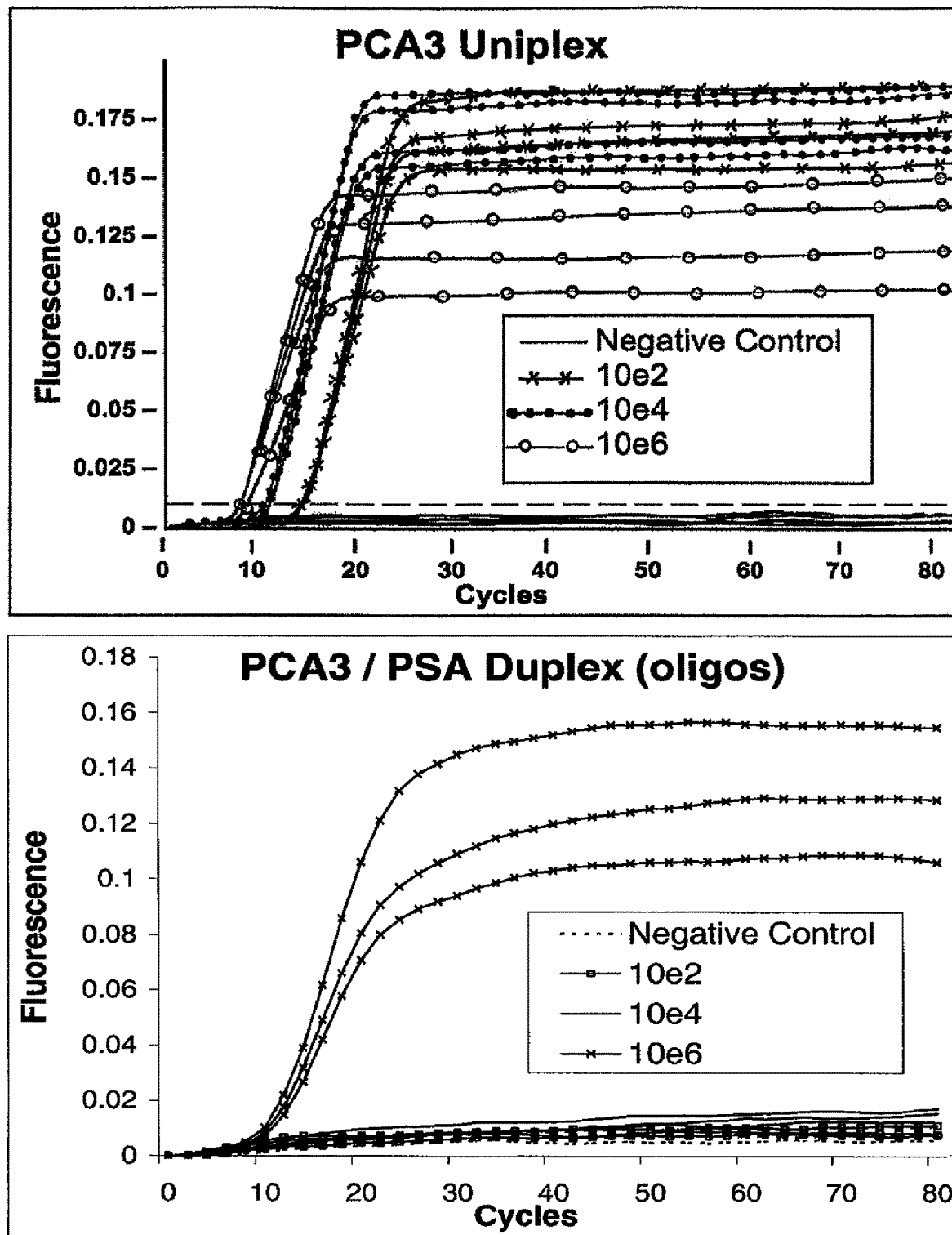

METHODS AND COMPOSITIONS FOR NUCLEIC ACID AMPLIFICATION

CROSS REFERENCE TO RELATED APPLICATIONS

This application is a continuation of U.S. application Ser. No. 15/058,702, filed Mar. 2, 2016, which is a division of U.S. application Ser. No. 13/956,158, filed Jul. 31, 2013, now U.S. Pat. No. 9,399,796, which is a division of U.S. application Ser. No. 12/828,676, filed Jul. 1, 2010, now U.S. Pat. No. 8,512,055, which claims the benefit of priority of U.S. Provisional Application No. 61/222,150, filed on Jul. 1, 2009, the contents of each are incorporated herein by reference in their entirety.

REFERENCE TO SEQUENCE LISTING

The instant application contains a Sequence Listing which has been submitted in ASCII format via EFS-Web and is hereby incorporated by reference in its entirety. Said ASCII Copy, created on Feb. 12, 2018, is named "GP237-06.CN1_ST25.txt" and is 27 KB in size

FIELD

This invention relates to molecular biology, more specifically to in vitro amplification of nucleic acids, which is useful for increasing the number of copies of a nucleic acid sequence to provide sufficient copies to be readily detected.

BACKGROUND

Nucleic acid amplification provides a means for making more copies of a nucleic acid sequence that is relatively rare or unknown, for identifying the source of nucleic acids, or for making sufficient nucleic acid to provide a readily detectable amount. Amplification is useful in many applications, for example, in diagnostics, drug development, forensic investigations, environmental analysis, and food testing. Many methods for amplifying nucleic acid sequences in vitro are known, including polymerase chain reaction (PCR), ligase chain reaction (LCR), replicase-mediated amplification, strand-displacement amplification (SDA), "rolling circle" types of amplification, and various transcription associated amplification methods. These known methods use different techniques to make amplified sequences, which usually are detected by using a variety of methods. PCR amplification uses a DNA polymerase, oligonucleotide primers, and thermal cycling to synthesize multiple copies of both strands of a double-stranded DNA (dsDNA) or dsDNA made from a cDNA (U.S. Pat. Nos. 4,683,195, 4,683,202, and 4,800,159). LCR amplification uses an excess of two complementary pairs of single-stranded probes that hybridize to contiguous target sequences and are ligated to form fused probes complementary to the original target, which allows the fused probes to serve as a template for further fusions in multiple cycles of hybridization, ligation, and denaturation (U.S. Pat. No. 5,516,663 and EP 0320308 B1). Replicase-mediated amplification uses a self-replicating RNA sequence attached to the analyte sequence and a replicase, such as Q.beta.-replicase, to synthesize copies of the self-replicating sequence specific for the chosen replicase, such as a Q.beta.viral sequence (U.S. Pat. No. 4,786,600). The amplified sequence is detected as a substitute or reporter molecule for the analyte sequence. SDA uses a primer that contains a recognition site for a restriction endonuclease which allows the endonuclease to nick one strand of a hemimodified dsDNA that includes the target sequence, followed by a series of primer extension and strand displacement steps (U.S. Pat. Nos. 5,422,252 and 5,547,861). Rolling circle types of amplification rely on a circular or concatenated nucleic acid structure that serves as a template used to enzymatically replicate multiple single-stranded copies from the template (e.g., U.S. Pat. Nos. 5,714,320 and 5,834,252). Transcription associated amplification refers to methods that amplify a sequence by producing multiple transcripts from a nucleic acid template. Such methods generally use one or more oligonucleotides, of which one provides a promoter sequence, and enzymes with RNA polymerase and DNA polymerase activities to make a functional promoter sequence near the target sequence and then transcribe the target sequence from the promoter (e.g., U.S. Pat. Nos. 5,399,491, 5,554,516, 5,130,238, 5,437,990, 4,868,105 and 5,124,246, PCT Pub. WO 1988/010315 A1 and US Pub. 2006-0046265 A1). Nucleic acid amplification methods may amplify a specific target sequence (e.g., a gene sequence), a group of related target sequences, or a surrogate sequence, which may be referred to as a tag or reporter sequence that is amplified and detected in place of the analyte sequence. The surrogate sequence is only amplified if the analyte target sequence is present at some point during the reaction. Modified nucleic acid amplification methods may amplify more than one potential target sequence by using "universal" primer(s) or universal priming. One form of PCR amplification uses universal primers that bind to conserved sequences to amplify related sequences in a PCR reaction (Okamoto et al., 1992, *J. Gen. Virol.* 73(Pt. 3):673-9, Persing et al, 1992, *J. Clin. Microbiol.* 30(8):2097-103). Methods that use universal primers often are paired with use of a species-specific, gene-specific or type-specific primer or primers to generate an amplified sequence that is unique to a species, genetic variant, or viral type, which may be identified by sequencing or detecting some other characteristic of the amplified nucleic acid. Anchored PCR is another modified PCR method that uses a universal primer or an "adapter" primer to amplify a sequence that is only partially known. Anchored PCR introduces an "adaptor" or "universal" sequence into a cDNA and then uses a primer that binds to the introduced sequence in subsequent amplification steps. Generally, anchored-PCR uses a primer directed to a known sequence to make a cDNA, adds a known sequence (e.g., poly-G) to the cDNA or uses a common sequence in the cDNA (e.g., poly-T), and performs PCR by using a universal primer that binds to the added or common sequence in the cDNA and a downstream target-specific primer (Loh et al., 1989, *Science* 243(4888):217-20; Lin et al., 1990, *Mol. Cell. Biol.* 10(4): 1818-21). Nested PCR may use primer(s) that contain a universal sequence unrelated to the analyte target sequence to amplify nucleic acid from unknown target sequences in a reaction (Sullivan et al, 1991, *Electrophoresis* 12(1):17-21; Sugimoto et al., 1991, *Agric. Biol. Chem.* 55(11):2687-92).

Chamberlain, et al., (Nucleic Acid Research, (1988) 16:11141 11156) first demonstrated multiplex PCR analysis for the human dystrophin gene. Multiplex reactions are accomplished by careful selection and optimization of specific primers. Developing robust, sensitive and specific multiplex reactions have demanded a number of specific design considerations and empiric optimizations. This results in long development times and compromises reaction conditions that reduce assay sensitivity. In turn, development of new multiplex diagnostic tests becomes very costly. A number of specific problems have been identified that limit multiplex reactions. Incorporating primer sets for more than one target requires careful matching of the reaction efficiencies. If one primer amplifies its target with even slightly better efficiency, amplification becomes biased toward the more efficiently amplified target resulting in inefficient amplification, varied sensitivity and possible total failure of other target genes in the multiplex reaction. This is called "preferential amplification." Preferential amplification can sometimes be corrected by carefully matching all primer sequences to similar lengths and GC content and optimizing the primer concentrations, for example by increasing the primer concentration of the less efficient targets. Incorporation of inosine into primers in an attempt to adjust the primer amplification efficiencies (Wu, et al., U.S. Pat. No. 5,738,995 (1998)) has also been used. Another approach is to design chimeric primers, wherein each primer contains a 3' region complementary to sequence-specific target recognition and a 5' region made up of a universal sequence. Using the universal sequence primer permits the amplification efficiencies of the different targets to be normalized. See, Shuber, et al., Genome Research, (1995) 5:488 493; and U.S. Pat. No. 5,882,856. Chimeric primers have also been utilized to multiplex isothermal strand displacement amplification (U.S. Pat. Nos. 5,422,252, 5,624,825, and 5,736,365). Since multiple primer sets are present in multiplex amplification reactions, multiplexing is frequently complicated by artifacts resulting from cross-reactivity of the primers. All possible combinations must be analyzed so that as the number of targets increases this becomes extremely complex and severely limits primer selection. Even carefully designed primer combinations often produce spurious products that result in either false negative or false positive results. The reaction kinetics and efficiency is altered when more than one reaction is occurring simultaneously. Each multiplexed reaction for each different specimen type must be optimized for $MgCl_2$ concentration and ratio to the deoxynucleotide concentration, KCl concentration, amplification enzyme concentration, and amplification reaction times and temperatures. There is competition for the reagents in multiplex reactions so that all of the reactions plateau earlier. As a consequence, multiplexed reactions in general are less sensitive than the corresponding uniplex reaction. Another consideration to simultaneous amplification reactions is that there must be a method for the discrimination and detection of each of the targets. The number of multiplexed targets is then further limited by the number of dye or other label moieties distinguishable within the reaction. As the number of different fluorescent moieties to be detected increases, so does the complexity of the optical system and data analysis programs necessary for result interpretation. An approach is to hybridize the amplified multiplex products to a solid phase then detect each target. This can utilize a planar hybridization platform with a defined pattern of capture probes (U.S. Pat. No. 5,955, 268), or capture onto a beadset that can be sorted by flow cytometry (U.S. Pat. No. 5,981,180). Due to the summation of all of the technical issues discussed, current technology for multiplex gene detection is costly and severely limited in the number and combinations of genes that can be analyzed. Generally, these reactions multiplex only two or three targets with a maximum of around ten targets. Isothermal amplification reactions are more complex than PCR and even more difficult to multiplex. See, Van Deursen, et al., Nucleic Acid Research, (1999) 27:e15. U.S. Pat. No. 6,605,451 discloses a two-step PCR multiplex reaction wherein a small amount of each primer pair is added into a first PCR reaction mix and a first amplification is performed to increase the amount of target nucleic acids in the reaction. The first reaction is stopped mid log phase and is then separated into second reactions each containing primer pairs for one of the target nucleic acids. A full amplification is then performed. Though a limited amount of each of the multiplex primer pairs is present in the first reaction, the above discussed problems common to multiplexing are still present. Further, these various primer pair species can all transfer into the secondary amplification reactions, causing common multiplex problems there as well. There is still a need, therefore, for a method, which permits multiplexing of large numbers of targets without extensive design and optimization constraints, and which avoids problems common to multiplexing in the presence of a plurality of different amplifications oligomer pairs. There is also a further need for a method of detecting a significantly larger number of gene targets from a small quantity of initial target nucleic acid.

SUMMARY

The current invention is directed to compositions, methods and kits for performing amplification reactions, and preferably multiplex amplification reactions. In one embodiment, there is a composition comprising a first amplification oligomer member linked to a second amplification oligomer member to form an amplification oligomer complex. In one aspect, the first and second amplification oligomer members are a primer amplification oligomer and a promoter primer or promoter provider amplification oligomer. In one aspect, the first and second amplification oligomer members are a first primer amplification oligomer and a second primer amplification oligomer. In one aspect, the first and second amplification oligomer members are a promoter primer or promoter provider amplification oligomer and a primer amplification oligomer. In one aspect, the first and second oligomer members forming the complex are linked together directly. In another aspect, the first and second amplification oligomer members are a primer amplification oligomer and a promoter primer or promoter provider amplification oligomer, and the first and second oligomer members forming the complex are linked together indirectly. In one aspect, one or both of the first and second oligomer members forming the complex comprises a universal tag sequence region. A universal tag sequence region is useful for allowing subsequent amplification to occur using a universal amplification oligomer targeting that universal tag sequence region.

In one embodiment, there is a method for performing an amplification reaction wherein the method comprises one or more amplification oligomer complexes comprising linked first and second amplification oligomer members. In one aspect of the method, the amplification oligomer complex is hybridized to a target nucleic acid, the target nucleic acid with hybridized amplification oligomer complex is then captured, and other components are washed away. In one aspect, target capture is performed using a target capture oligomer, an immobilized probe oligomer and a solid support such as a magnetic bead. In this aspect, the captured target nucleic acid and hybridized amplification oligomer complex is separated from other sample components using a magnetic bead capture system, is washed and is then resuspended. In one aspect, the captured target nucleic acid and hybridized amplification oligomer complex is resuspended into an amplification reaction mixture. In another aspect, the captured target nucleic acid and hybridized amplification oligomer complex is resuspended into a pre-amplification reaction mixture. In an embodiment of the method wherein the target nucleic acid is resuspended into a pre-amplification reaction, the pre-amplification reaction mixture is an oligomer-less reaction mixture. In one aspect, the pre-amplification reaction mixture comprises a reverse transcriptase and/or an RNA polymerase. The pre-amplification reaction step, then, includes forming of a complementary strand of the target nucleic acid and generating RNA transcripts therefrom. In embodiments wherein the amplification oligomer complex comprises first and second amplification oligomers wherein one or both of these oligomers comprises an universal tag sequence region, then the RNA transcripts generated therefrom will comprise a universal sequence region or complement thereof. Following pre-amplification, initial/first amplification product in the pre-amplified sample is then amplified in a secondary amplification reaction. The secondary amplification reaction mixtures comprise either target specific amplification oligomers, universal amplification oligomer or both. Secondary amplifications are preferably performed by transferring all or a part of the pre-amplified product to one or more reaction wells containing an amplification reaction mixture. In the secondary amplification reaction a secondary amplification product is generated from template transferred from the pre-amplified sample. Amplified product is detected by any of a number of detection methods. In one aspect, the detection step is a detection probe based detection step. In another aspect, the detection step is a real-time detection step. In another aspect, the detection step is a sequencing step. In another aspect, the detection step uses mass spectrometry.

In one embodiment, there is a method for performing a multiplex amplification reaction wherein the method comprises two or more amplification oligomer complexes comprising linked first and second amplification oligomer members, and wherein each of the two or more amplification oligomers is configured to hybridize to a different target nucleic acid. In one aspect of the method, the amplification oligomer complexes are hybridized to their target nucleic acids, the target nucleic acids with hybridized amplification oligomer complexes are then captured, and other components are washed away, including unhybridized amplification oligomer complexes. The target capture step is performed using a target capture oligomer, an immobilized probe oligomer and a solid support such as a magnetic bead. Following magnetic bead capture and wash, the target nucleic acids and hybridized amplification oligomer complexes are resuspended into a pre-amplification reaction mixture. The pre-amplification reaction mixture is an oligomer-less reaction mixture, preferably comprising a reverse transcriptase and/or an RNA polymerase. For each of the target nucleic acids in the pre-amplification, the hybridized amplification oligomer complex is used by the enzymes to first form complementary strands for each of the target nucleic acids, and to then generate RNA transcripts therefrom. Following pre-amplification, initial/first amplification product in the pre-amplified sample is then split into two or more secondary amplification reactions, each of which comprises target specific amplification oligomers for one of the target nucleic acid RNA products. In the secondary amplification reaction a secondary amplification product is generated from template transferred from the pre-amplified sample. Amplification is performed and the amplified product is detected by any of a number of detection methods. In one aspect, the detection step is a detection probe based detection step. In another aspect, the detection step is a real-time detection step. In another aspect, the detection step is a sequencing step. In another aspect, the detection step uses mass spectrometry.

In one embodiment, an amplification oligomer complex composition is disclosed that includes a target specific universal (TSU) promoter oligonucleotide that includes a 5' promoter sequence, an internal first universal sequence (U1), and a 3' first target specific sequence (TS1) that binds specifically to a target sequence contained in a target nucleic acid, wherein the TSU promoter oligonucleotide is a TSU promoter primer that has a 3' terminus that is capable of being extended by a polymerase, or is a TSU promoter provider oligonucleotide that has a blocked 3' terminus that is incapable of being extended by a polymerase, a TSU non-promoter primer oligonucleotide made up of a 5' second universal sequence (U2) and a 3' second target specific sequence (TS2) which is different from the TS1, and a means for directly or indirectly joining the TSU promoter oligonucleotide to the TSU non-promoter primer oligonucleotide, thereby forming a target specific universal (TSU) primer complex or TSU-complex.

In another embodiment, an amplification oligomer complex composition is disclosed that includes a first promoter oligonucleotide that includes a 5' promoter sequence, and a 3' first target specific sequence (TS1) that binds specifically to a target sequence contained in a target nucleic acid, wherein the promoter oligonucleotide is a promoter primer that has a 3' terminus that is capable of being extended by a polymerase, or is a promoter provider oligonucleotide that has a blocked 3' terminus that is incapable of being extended by a polymerase, a second non-promoter primer oligonucleotide made up of a second target specific sequence (TS2) which is different from the TS1, and a means for directly or indirectly joining the promoter oligonucleotide to the non-promoter primer oligonucleotide, thereby forming an amplification oligomer complex. In one aspect, the means for means for joining the promoter oligonucleotide to the non-promoter primer oligonucleotide is an indirect means. In another aspect, the means for means for joining the promoter oligonucleotide to the non-promoter primer oligonucleotide is a direct hybridization, wherein the non-promoter primer oligomer comprises a 3' target specific sequence and a 5' nucleic acid sequence that is substantially complementary to all or a portion of the promoter sequence of the first promoter oligomer, thereby forming a DH-complex.

In one embodiment, the means for directly joining the promoter oligonucleotide to the non-promoter primer oligonucleotide is a covalent linkage. In another embodiment, the covalent linkage is formed via a polynucleotide linker sequence, which may be a covalent linkage formed via a non-nucleotide a basic linker compound. Another embodiment uses a means for indirectly joining the promoter oligonucleotide to the non-promoter primer oligonucleotide that is a non-covalent linkage of members of a binding pair to join the promoter oligonucleotide and the non-promoter primer oligonucleotide to a support, in which one member of the binding pair is present on the promoter oligonucleotide or the non-promoter primer oligonucleotide and the other member of the binding pair is attached to the support. In another embodiment, the means for directly joining the promoter oligonucleotide to the non-promoter primer oligonucleotide is a hybridization complex between a first sequence on the promoter oligonucleotide and a second sequence on the non-promoter primer that is complementary to the first sequence on the promoter oligonucleotide. The means for indirectly joining the promoter oligonucleotide to the non-promoter primer oligonucleotide may be a hybridization complex that includes an S-oligonucleotide that contains a first sequence complementary to a sequence in the promoter oligonucleotide and a second sequence complementary to a sequence in the non-promoter primer oligonucleotide. In one embodiment the S-oligonucleotide contains a first sequence complementary to the universal sequence in the promoter oligonucleotide and the S-oligonucleotide contains a second sequence complementary to the universal sequence in the non-promoter primer oligonucleotide. The composition may also include a target specific capture oligonucleotide that contains a sequence that hybridizes specifically to a sequence in the target nucleic acid. The target specific capture oligonucleotide may hybridize to the target nucleic acid at a target sequence that is different from the target sequence hybridized by the promoter oligonucleotide TS sequence or by the non-promoter primer TS sequence. The target capture oligonucleotide may contain a means for binding the target nucleic acid to a support. The composition may also include a universal promoter primer made up a 5' promoter sequence and a 3' universal sequence that is the same as the universal sequence of the promoter oligonucleotide. Another embodiment is a composition that further includes a universal primer made up a universal sequence that is the same as the universal sequence of the non-promoter primer oligonucleotide. The composition may also include a blocker oligonucleotide that hybridizes specifically to a sequence in a target nucleic acid strand that is completely different, partially different or the same as the sequence in the target nucleic acid strand that the TS sequence of the promoter oligonucleotide or the TS sequence of the non-promoter primer oligonucleotide binds, and wherein the blocker oligonucleotide has a 3' blocked terminus that is not capable of being extended by a polymerase. In some embodiments that include an S-oligonucleotide, it is made up of (1) a first terminal region sequence that is complementary to the U1 sequence of the promoter primer and (2) a second terminal region sequence that is complementary to the U2 sequence of the TSU non-promoter primer, and (3) a linking moiety that links the first and second terminal region sequences. The linking moiety may be a non-nucleic acid chemical compound that covalently links the first and second terminal region sequences. The composition may also include at least one universal promoter primer made up of a 5' promoter sequence and a 3' U1 sequence and at least one target specific primer (TSP) made up of a sequence that is complementary to a sequence contained in an RNA transcript made from a double stranded DNA that contains a cDNA sequence made from synthetic extension of the 3' end of the promoter primer oligonucleotide.

Also disclosed is a method of amplifying a target nucleic acid comprising the steps of: isolating a target nucleic acid from a mixture by binding to the target nucleic acid a target capture probe that binds specifically to the target nucleic acid and provides a means for attaching the bound target nucleic acid to a support that is separated from the mixture, and further hybridizing to the target nucleic acid in the mixture a amplification oligomer complex made up of (A)(1) a TSU promoter primer oligonucleotide that includes a 5' promoter sequence, an internal first universal sequence (U1), and a 3' first target specific sequence (TS1) that binds specifically to a target sequence contained in a target nucleic acid, and a 3' terminus that is capable of being extended by a polymerase, (2) a TSU non-promoter primer oligonucleotide made up of a 5' second universal sequence (U2) and a 3' second target specific sequence (TS2) which is different from the TS1, and (3) a means for directly or indirectly joining the TSU promoter oligonucleotide to the TSU non-promoter primer oligonucleotide; or (B)(1) a promoter primer oligonucleotide that includes a 5' promoter sequence, and a 3' first target specific sequence (TS1) that binds specifically to a target sequence contained in a target nucleic acid, and a 3' terminus that is capable of being extended by a polymerase, (2) a non-promoter primer oligonucleotide comprising at least a second target specific sequence (TS2) which is different from the TS1, and (3) a means for directly or indirectly joining the promoter oligonucleotide to the non-promoter primer oligonucleotide. The method includes hybridizing the promoter primer oligonucleotide to a target sequence in the target nucleic acid via a TS sequence in the promoter primer, synthetically extending the 3' terminus of the promoter primer oligonucleotide hybridized to the target nucleic acid by using a polymerase in vitro nucleic acid synthesis in which the target nucleic acid is a template to make a first cDNA strand, hybridizing the non-promoter primer oligonucleotide to the first cDNA strand by specific hybridization of the TS sequence in the non-promoter primer oligonucleotide to a target sequence contained in the first cDNA strand, synthetically extending the 3' terminus of the non-promoter primer oligonucleotide hybridized to the first cDNA strand by a polymerase in vitro nucleic acid synthesis to made a second DNA strand, thereby making a substantially double-stranded DNA. Depending on whether complex A or complex B, described directly above, is used as the amplification oligomer complex, then the double stranded DNA will contain a functional promoter sequence and, optionally, the U1 sequence. RNA transcripts are then enzymatically transcribed from the functional promoter sequence of the substantially double-stranded DNA. The RNA transcripts comprise a first target specific sequence (TS1), a second target specific sequence (TS2'). Further, when the amplification oligomer complex at A is used that the RNA transcripts further comprise a 5' U1 region sequence, and a 3' universal sequence (U2') that is complementary to the U2 sequence. The method further comprises amplification either using target specific amplification oligomers or, if the U1 and/or U2' sequences are present in the RNA transcript, using a universal primer oligonucleotide (UP2) that contains a universal sequence U2 to the RNA transcript at the U2' sequence. Amplification is performed under isothermal conditions, synthetically extending the 3' terminus of primer oligomer (either universal or target specific, depending on the amplification oligomer complex used) by enzymatic in vitro nucleic acid synthesis to make a cDNA strand, and enzymatically removing the RNA transcript strand, hybridizing a promoter primer oligonucleotide (either universal or target specific) to the cDNA made in the previous step under isothermal conditions, synthetically extending at the 3' terminus by enzymatic in vitro nucleic acid synthesis to make a dsDNA that contains a functional promoter, and transcribing multiple RNA transcripts from the functional promoter of the dsDNA, which are amplification products that may serve as templates for further enzymatic in vitro nucleic acid synthesis under isothermal conditions. The method may also include the step of detecting the amplification products to indicate the presence of an analyte in the mixture from which the target nucleic acid was isolated. Detection can be real-time detection and/or quantitative detection.

Another disclosed method of amplifying a target nucleic acid includes isolating a target nucleic acid from a mixture by binding to the target nucleic acid a target capture probe that binds specifically to the target nucleic acid and provides a means for attaching the bound target nucleic acid to a support that is separated from the mixture, and further hybridizing to the target nucleic acid in the mixture an amplification oligomer complex made up of (A)(1) a TSU promoter oligonucleotide that includes a 5' promoter sequence, an internal first universal sequence (U1), and a 3' first target specific sequence (TS1) that binds specifically to a target sequence contained in a target nucleic acid, wherein the TSU promoter oligonucleotide is a TSU promoter provider oligonucleotide that has a blocked 3' terminus that is incapable of being extended by a polymerase, (2) a TSU non-promoter primer oligonucleotide made up of a 5' second universal sequence (U2) and a 3' second target specific sequence (TS2) which is different from the TS1, and (3) a means for directly or indirectly joining the TSU promoter oligonucleotide to the TSU non-promoter primer oligonucleotide; or (B)(1) a promoter oligonucleotide that includes a 5' promoter sequence and a 3' first target specific sequence (TS1) that binds specifically to a target sequence contained in a target nucleic acid, wherein the TSU promoter oligonucleotide is a TSU promoter provider oligonucleotide that has a blocked 3' terminus that is incapable of being extended by a polymerase, (2) a TSU non-promoter primer oligonucleotide comprising at least a 3' second target specific sequence (TS2) which is different from the TS1, and (3) a means for directly or indirectly joining the promoter oligonucleotide to the non-promoter primer oligonucleotide. The method steps also include hybridizing the non-promoter primer oligonucleotide to a target sequence in the target nucleic acid via the TS sequence in the non-promoter primer, optionally hybridizing a blocker oligonucleotide with a 3' blocked end that is incapable of being extended synthetically by a polymerase to a sequence on the target nucleic acid that is in the 5-primer direction away from the position that the non-promoter primer oligonucleotide hybridizes in the target nucleic acid, synthetically extending the 3' terminus of the non-promoter primer hybridized to the target nucleic acid by using a polymerase in vitro nucleic acid synthesis in which the target nucleic acid is a template to make a first cDNA strand, hybridizing the promoter provider oligonucleotide to the first cDNA strand by specific hybridization of the TS sequence in the promoter provider oligonucleotide to a target sequence contained in the first cDNA strand, synthetically extending the 3' terminus of the first cDNA by using sequence in the promoter provider as a template to make a substantially double-stranded DNA that contains a functional promoter sequence and, when the amplification oligomer complex at A is used, described directly above, further comprises the U1 sequence. RNA transcripts are then enzymatically transcribed from the functional promoter sequence of the substantially double-stranded DNA. The RNA transcripts comprise a first target specific sequence (TS1), a second target specific sequence (TS2'). Further, when the amplification oligomer complex at A is used that the RNA transcripts further comprise a 5' U1 region sequence, and a 3' universal sequence (U2') that is complementary to the U2 sequence. The method further comprises amplification either using target specific amplification oligomers or, if the U1 and/or U2' sequences are present in the RNA transcript, using a universal primer oligonucleotide (UP2) that contains a universal sequence U2 to the RNA transcript at the U2' sequence. Amplification is performed under isothermal conditions, synthetically extending the 3' terminus of the primer oligomer, either universal or target specific, by enzymatic in vitro nucleic acid synthesis to made a cDNA strand, and enzymatically removing the RNA transcript strand, hybridizing a promoter oligonucleotide, either universal or target specific, that contains a promoter sequence, optionally, a universal sequence U1, and a target specific sequence with a 3' blocked end to the cDNA made in the previous step and, under isothermal conditions, synthetically extending the 3' terminus of the cDNA to make a functional double-stranded promoter and transcribing multiple RNA transcripts from the functional promoter of the dsDNA. These RNA transcripts are amplification products that may serve as templates for further enzymatic in vitro nucleic acid synthesis under isothermal conditions. The method may further include the step of detecting the amplification products to indicate the presence of an analyte in the sample from which the target nucleic acid was isolated.

Also discloses is a method of amplifying a target nucleic acid that includes steps of isolating a target nucleic acid from a mixture by binding to the target nucleic acid a target capture probe that binds specifically to the target nucleic acid and provides a means for attaching the bound target nucleic acid to a support that is separated from the mixture and further hybridizing to the target nucleic acid in the mixture a target specific universal (TSU) promoter primer oligonucleotide that includes a 5' promoter sequence, an internal first universal sequence (U1), and a 3' first target specific sequence (TS1) that binds specifically to a target sequence contained in a target nucleic acid, and a 3' terminus that is capable of being extended by a polymerase, synthetically extending the 3' terminus of the TSU promoter primer oligonucleotide hybridized to the target nucleic acid by using a polymerase in vitro nucleic acid synthesis in which the target nucleic acid is a template to make a first cDNA strand, adding to the amplification reaction mixture a target specific (TS) non-promoter primer that contains a second target specific sequence (TS2) which is different from the TS1, hybridizing the TS non-promoter primer oligonucleotide to the first cDNA strand by specific hybridization of the TS2 sequence to a target sequence contained in the first cDNA strand, synthetically extending the 3' terminus of the TS non-promoter primer oligonucleotide hybridized to the first cDNA strand by a polymerase in vitro nucleic acid synthesis to made a second DNA strand, thereby making a substantially double-stranded DNA that contains a functional promoter sequence and the U1 sequence, enzymatically transcribing RNA transcripts from the functional promoter sequence of the substantially double-stranded DNA to make RNA transcripts that contain a 5' U1 region sequence, a first target specific sequence (TS1), a second target specific sequence (TS2'), hybridizing a universal promoter primer oligonucleotide that contains a universal sequence U1' to the RNA transcript at the U1 sequence, under isothermal conditions, synthetically extending the 3' terminus of the universal promoter primer by enzymatic in vitro nucleic acid synthesis to made a cDNA strand, and enzymatically removing the RNA transcript strand, hybridizing a TS non-promoter primer oligonucleotide to a specific sequence in the cDNA made in the previous step, under isothermal conditions, synthetically extending the 3' terminus of the TS non-promoter primer by enzymatic in vitro nucleic acid synthesis to made a dsDNA that contains a functional promoter, and transcribing multiple RNA transcripts from the functional promoter of the dsDNA, which transcripts are amplification products that may serve as templates for further enzymatic in vitro nucleic acid synthesis under isothermal conditions by repeating the synthetic steps. The method may further include detecting the amplification products to indicate the presence of an analyte in the mixture from which the target nucleic acid was isolated.

Another disclosed method of amplifying a target nucleic acid includes the steps of isolating a target nucleic acid from a mixture by binding to the target nucleic acid a target capture probe that binds specifically to the target nucleic acid and provides a means for attaching the bound target nucleic acid to a support that is separated from the mixture and further hybridizing to the target nucleic acid in the mixture a TSU non-promoter primer oligonucleotide made up of a 5' universal sequence (U2) and a 3' target specific sequence (TS2), hybridizing the TSU non-promoter primer oligonucleotide to a target sequence in the target nucleic acid via the TS2 sequence to a complementary sequence in the target nucleic acid, hybridizing a blocker oligonucleotide with a 3' blocked end that is incapable of being extended synthetically by a polymerase to a sequence on the target nucleic acid that is downstream from the position that the TSU non-promoter primer oligonucleotide hybridizes in the target nucleic acid, synthetically extending the 3' terminus of the TSU non-promoter primer hybridized to the target nucleic acid by using a polymerase in vitro nucleic acid synthesis in which the target nucleic acid is a template to make a first cDNA strand, hybridizing to the first cDNA strand a target specific TS promoter provider oligonucleotide that includes a 5' promoter sequence and a 3' target specific sequence (TS1) that binds specifically to a target sequence contained in a target nucleic acid, and a blocked 3' terminus that is incapable of being extended by a polymerase, by specific hybridization of the TS1 sequence to a complementary sequence in the first cDNA strand, synthetically extending the 3' terminus of the first cDNA by using sequence in the TS promoter provider as a template to make a substantially double-stranded DNA that contains a functional promoter sequence and a TS1 sequence, enzymatically transcribing RNA transcripts from the functional promoter sequence to make RNA transcripts that contain a 5' target specific sequence TS1, a target specific sequence TS2' and a U2' sequence, hybridizing a universal primer oligonucleotide (UP2) that contains a universal sequence U2 to the RNA transcript at the U2' sequence, under isothermal conditions, synthetically extending the 3' terminus of the UP2 by enzymatic in vitro nucleic acid synthesis to made a cDNA strand, and enzymatically removing the RNA transcript strand, hybridizing a TS promoter provider oligonucleotide that contains a promoter sequence and a 3' blocked end to the cDNA made in the previous step, under isothermal conditions, synthetically extending the 3' terminus of the cDNA to make a functional double-stranded promoter by using the TS promoter provider oligonucleotide as a template and by enzymatic in vitro nucleic acid synthesis to made a dsDNA that contains a functional promoter, and transcribing multiple RNA transcripts from the functional promoter of the dsDNA, which transcripts are amplification products that may serve as templates for further enzymatic in vitro nucleic acid synthesis under isothermal conditions by repeating the synthetic steps. The method may also include detecting the amplification products to indicate the presence of an analyte in the sample from which the target nucleic acid was isolated.

One embodiment is a method for simultaneously amplifying at least two different target nucleic acid sequences contained in a sample comprising the steps of: contacting a sample with at least two amplification oligomer complexes that hybridize to different target nucleic acid sequences, wherein each of the amplification oligomer complexes comprises a first amplification oligomer member that is directly joined to a second amplification oligomer member; pre-amplifying the target nucleic acid sequences using the amplification oligomer complexes, thereby generating first amplification products for each target nucleic acid hybridized by an amplification oligomer complex; splitting the pre-amplified sample into at least two separate secondary target specific amplification reactions; amplifying the pre-amplified sample generated in the pre-amplification reaction above using target specific amplification oligomers, thereby generating second amplification products. In this embodiment, the amplification oligomer complexes are configured to hybridize with different target nucleic acid sequences. In the pre-amplification step, an amount of first amplification product is generated, thereby increasing the amount of each target nucleic acid sequence that is available for secondary amplification in separate containers. The secondary amplification containers perform a specific amplification, either by way of target specific amplification primers in that secondary amplification reaction, and/or by target specific detection probes. Separate target specific amplification reactions avoid the problems encountered with multiplex amplification, e.g., primer dimers, different amplification efficiencies, target biased reagent consumption, mis-priming, cross-reactivity and other known problems.

In one aspect of this embodiment the sample is contacted with at least two amplification oligomer complexes and at least two target capture oligomers that hybridize to different target nucleic acid sequences. In one aspect, the at least two amplification oligomer complexes and the at least two target capture oligomers are contacted to the sample under conditions for hybridizing the at least two amplification oligomer complexes and the at least two target capture oligomers to their respective different target nucleic acid sequences present in the sample. In one aspect, the at least two target capture oligomers are contacted by a solid support and immobilized probe for performing a target capture step. In one aspect, a wash step is performed.

In one aspect of this embodiment, target nucleic acid sequences hybridized to amplification oligomer complexes are contacted with an oligomerless pre-amplification reaction reagent. Thus, the pre-amplification reaction occurs using just the amplification oligomer members forming the amplification oligomer complex. In one aspect, the oligomerless pre-amplification reaction reagent comprises a reverse transcriptase, an RNA polymerase or both. In one aspect, the pre-amplifying reaction comprises contacting the at least two target nucleic acid sequences with an oligomerless pre-amplification reaction reagent comprises a reverse transcriptase, an RNA polymerase or both. In one aspect, the pre-amplification reaction generates from one of the at least two target nucleic acid sequences, a first amplification product that is a plurality of RNA transcripts.

In one aspect of this embodiment, the amplifying reaction that generates secondary amplification products is a quantitative amplification reaction. In one aspect, the amplifying reaction that generates secondary amplification products is an exponential amplification reaction.

In one aspect of this embodiment, a portion of the pre-amplification reaction is transferred into a secondary target specific amplification reaction comprising at least one target specific amplification oligomer. In one aspect, an additional portion of the pre-amplification reaction is transferred into a secondary target specific amplification reaction comprising at least one different target specific amplification oligomer. The different first amplification products generated from each different target nucleic acid sequence hybridized to one of the different amplification oligomer complexes is then amplified in a separate target specific secondary amplification. In another aspect, the secondary amplification can be a multiplex amplification reaction that is configured to amplify fewer targets that what is suspected to be in the sample. For example, if it is suspected that the sample has four targets, the pre-amplification reaction will generate up to four different first amplification products, and then the pre-amplification reaction can be split into at least one, more preferably two, more preferably three, more preferably four or more separate secondary amplification reactions. If just one, then the pre-amplification reaction was to increase the amount of template for the secondary amplification reaction and/or to incorporate universal tag sequences. If two or three, then at least one of the secondary amplifications is a multiplex reaction but with fewer than four target nucleotide sequences. Multiplex reactions having fewer targets or optimized pairs can avoid some of the multiplex problems, this is more true is universal tag sequences have been incorporated. If four, then there can be a separate secondary amplification reaction for each target suspected in the sample. If more than four, then the first amplification products can be specifically amplified more than one target sequence and/or can be amplified in duplicate. In one aspect, the first amplification products are divided into a number of secondary target specific amplification reactions that is equal to the number of different target nucleic acid sequences suspected of being present in the sample.

In one aspect, the pre-amplifying reaction is accomplished using a substantially isothermal amplification reaction. In one aspect, the secondary amplification reaction is accomplished using a substantially isothermal amplification reaction. In one aspect, the first amplification product generated in the pre-amplifying step for a target nucleic acid hybridized by an amplification oligomer complex is from 100 to 10000 RNA transcripts.

In one aspect, the amplification oligomer complex is a first amplification oligomer indirectly joined to a second amplification oligomer complex. In one aspect, the amplification oligomer complex is a first amplification oligomer directly joined to a second amplification oligomer complex. In an aspect, the first and second amplification oligomers are joined using a DH-complex. In an aspect, the first and second amplification oligomers are joined using an S-oligo. In an aspect, the first and second amplification oligomers are joined using a non-nucleotide linker. In one aspect, the first and second oligomer members of the amplification oligomer complex are non-promoter primers, promoter primers (with or without blocked 3'-ends), and combinations thereof. In one aspect, the amplification oligomer complex comprises a first amplification oligomer member that is a non-promoter primer comprising a target specific sequence joined on its 5' end to a linking member for linking the first amplification oligomer member to a second amplification oligomer member of the amplification oligomer complex. In one aspect, the second amplification oligomer member is a promoter primer, optionally comprising a blocked 3' terminus. In an aspect, the first oligomer member comprises a linking member that is a nucleotide sequence that is complementary to a portion of the nucleotide sequence of the second amplification oligomer member. In an aspect, the first oligomer member comprises a linking member that is a nucleotide sequence that is complementary to the promoter sequence of the second amplification oligomer member. In one aspect, the amplification oligomer complex is formed before being added into the pre-amplification reaction mixture. In one aspect, the amplification oligomer complex is formed and then is added into a target capture reaction mixture. In one aspect, the amplification oligomer complex is formed under hybridizing conditions during a target capture step.

In one aspect, a target capture reagent is contacted to the sample, hybridization conditions are provided and the captured target nucleic acids and amplification oligomer complexes are removed from the sample components and then resuspended in an oligomerless pre-amplification reagent for pre-amplification.

In one aspect, the pre-amplification reaction method further comprises using a blocker oligomer. Blockers are useful in defining the 3'-end of an amplification product In one aspect, the secondary amplification product is detected. In one aspect the first amplification product is detected. Detection can be probe based, sequencing based, mass-spectrometry based, gel electrophoresis based, or other common detection technique known in the art. In one aspect, amplifications product from the secondary amplification reaction is detected using a probe based detection step. In one aspect, the probe based detection step is a real-time detection step.

One embodiment is a method for simultaneously amplifying at least two different target nucleic acid sequences contained in a sample comprising the steps of: contacting a sample with at least two different amplification oligomer complexes, wherein each of the amplification oligomer complexes comprise a first amplification oligomer member with a 3' target specific sequence, joined to a second amplification oligomer member with a 3' target specific sequence; generating first amplification products for each target nucleic acid hybridized by an amplification oligomer complex; splitting the first amplification products into at least two separate secondary target specific amplification reactions; and then generating second amplification products. In one aspect, the first amplification oligomer members for each of the different amplification oligomer complexes, are non-promoter primers. In one aspect, the first amplification oligomers comprise a universal nucleotide sequence joined at the 5' end of the target specific sequence (universal tag). In one aspect, each first amplification oligomer from each different amplification oligomer complex has a universal nucleotide sequence with substantially similar nucleotide sequences. In one aspect, the first amplification oligomer members for each of the different amplification oligomer complexes, are promoter oligonucleotides, optionally blocked at their 3' ends. In one aspect, the first amplification oligomers comprise a universal nucleotide sequence joined at the 5' end of the target specific sequence and at the 3' end of the promoter sequence. In one aspect, the first amplification oligomer from each different amplification oligomer complex has a universal nucleotide sequence with substantially similar nucleotide sequences. In one aspect, the second amplification oligomer members for each of the different amplification oligomer complexes, are non-promoter primers. In one aspect, the second amplification oligomers comprise a universal nucleotide sequence joined at the 5' end of the target specific sequence. In one aspect, the second amplification oligomer members for each of the amplification oligomer complexes, are promoter oligonucleotides, optionally blocked at their 3' ends. In one aspect, each second amplification oligomer from each different amplification oligomer complex has a universal nucleotide sequence with substantially similar nucleotide sequences. In one aspect, the different amplification oligomer complexes are made of first and second amplification oligomer combinations selected from the group consisting of: two non-promoter primers; two non-promoter primers, one of which has a universal tag; two non-promoter primers, both of which have a universal tag; a non-promoter primer and a promoter primer (with or without a 3'blocked end); a non-promoter primer and a promoter primer (with or without a 3'blocked end), one of which has a universal tag sequence; a non-promoter primer and a promoter primer (with or without a 3'blocked end), both of which have a universal tag sequence; a promoter primer (with or without a 3'blocked end) and a non-promoter primer; a promoter primer (with or without a 3'blocked end) and a non-promoter primer, one of which has a universal tag sequence; a promoter primer (with or without a 3'blocked end) and a non-promoter primer, both of which have a universal tag sequence.

In one aspect, the amplification oligomer complex is a first amplification oligomer indirectly joined to a second amplification oligomer complex. In one aspect, the amplification oligomer complex is a first amplification oligomer directly joined to a second amplification oligomer complex. In an aspect, the first and second amplification oligomers are joined using a DH-complex. In an aspect, the first and second amplification oligomers are joined using an S-oligo. In an aspect, the first and second amplification oligomers are joined using a non-nucleotide linker. In one aspect, the first amplification oligomer member and the second amplification oligomer member of the amplification oligomer complex are both non-promoter primers joined at their 5' ends using a non-nucleotide linker, and wherein at least one of the first amplification oligomer or the second amplification oligomer has a universal nucleotide sequence joined at the 5' end of the target specific sequence. In one aspect, the first and second oligomer members of the amplification oligomer complex are non-promoter primers, promoter primers (with or without blocked 3'-ends), and combinations thereof. In one aspect, the amplification oligomer complex comprises a first amplification oligomer member that is a non-promoter primer comprising a target specific sequence joined on its 5' end to a linking member for linking the first amplification oligomer member to a second amplification oligomer member of the amplification oligomer complex. In one aspect, the second amplification oligomer member is a promoter primer, optionally comprising a blocked 3' terminus. In an aspect, the first oligomer member comprises a linking member that is a nucleotide sequence that is complementary to a portion of the nucleotide sequence of the second amplification oligomer member. In an aspect, the first oligomer member comprises a linking member that is a nucleotide sequence that is complementary to the promoter sequence of the second amplification oligomer member. In one aspect, the amplification oligomer complex is formed before being added into the pre-amplification reaction mixture. In one aspect, the amplification oligomer complex is formed and then is added into a target capture reaction mixture. In one aspect, the amplification oligomer complex is formed under hybridizing conditions during a target capture step. In one aspect, the first amplification oligomer complex is made of a non-promoter primer and a promoter primer, optionally blocked at its 3' end, wherein the non-promoter primer comprises a nucleotide sequence that is joined to the 5' end of the target specific sequence, and wherein the nucleotide sequence is substantially the complement of the promoter primer promoter sequence oligomer member, thereby joining the first and second amplification oligomer members by hybridizing the complementary promoter sequence to the promoter sequence.

In one aspect, the first amplification product is generated in a substantially isothermal amplification reaction. In one aspect, the e first amplification products are RNA transcripts.

In one aspect, the method includes contacting the sample with at least one target capture oligomer. In one aspect. at least one target capture oligomer and at least two different amplification oligomer complexes hybridize to a target nucleic acid sequence in the sample, thereby capturing the target nucleic acid sequence, and wherein the target capture oligomer:target nucleic acid sequence:amplification oligomer complex is isolated from other components of the sample. For simplicity in describing these entities, the use of ":" means that the components are hybridized together. In one aspect. a wash step is performed.

In one aspect, a target capture oligomer:target nucleic acid sequence:amplification oligomer complex is resuspended in an oligomerless pre-amplification reaction mixture. In one aspect, the oligomerless pre-amplification reaction mixture comprises a polymerase. In one aspect, the oligomerless pre-amplification reaction mixture comprises a reverse transcriptase. In one aspect, the pre-amplification reaction mixture comprises an enzyme selected from the group consisting of: a polymerase, an RNA-dependent DNA polymerase, a DNA-dependent DNA polymerase, a DNA-dependent DNA polymerase, a reverse transcriptase, an RNase, or a combination thereof.

In one aspect, the amplification oligomer complex comprises two amplification oligomer members selected from the group consisting of: non-promoter primers and promoter primers, optionally blocked at the 3' end, wherein at least one of the amplification oligomer members comprises a universal tag sequence, the first amplification products are split into at least two separate secondary target specific amplification reactions, wherein the secondary target specific amplification reaction includes at least one primer targeting all or a portion of the universal tag sequence. In one aspect, the secondary amplification products are detected using a target specific detection probe oligomer. In one aspect, the secondary amplification products are detected in real-time.

In one aspect, at least two different amplification oligomer complexes are configured to hybridize two different target nucleic acid sequences on the same target nucleic acid. In this aspect, it can be determined whether two amplification products are part of the same target nucleic acid or are part of separate target nucleic acids. For example, whether an insertion element has integrated into a genome, as is the case with antibiotic resistance genes integrating into bacterial genomes. Also, fusions can be determined, such as promoter sequence fused to an oncogene. By capturing, the single target nucleic acid that can comprise one or two of these target sequences, hybridizing the different amplification oligomer complexes, removing the hybridized complex from other sample components, and then performing an amplification reaction, it can be determined whether both target nucleotide sequence are on a single target nucleic acid by detecting the presence of one or both amplification products. Both products means both target nucleotide sequence were present on the same target nucleic acid. In one aspect, a target capture oligomer is hybridized to the target nucleic acid and the target capture oligomer:target nucleic acid:two different amplification oligomer complexes is separated from other components in the sample. In one aspect, a first target nucleic acid sequence is an insertion sequence in the target nucleic acid and a second target nucleic acid sequence is not an insertion sequence in the target nucleic acid, and wherein the pre-amplification reaction generates first amplification products from the non-insertion sequence and from the insertion sequence if present in the target nucleic acid. In one aspect, the presence of the target nucleic acid sequences can be determined by detecting the first amplification product, or by performing a single secondary target specific amplification reaction or by performing two different secondary target specific amplification reactions.

In one aspect, a blocker oligomer is used to define the 3' end of the first amplification product.

In one aspect, a first amplification product is detected in a detecting step. Detection can be probe based, sequencing based, mass-spectrometry based, gel electrophoresis based, or other common detection technique known in the art. In one aspect, amplifications product from the secondary amplification reaction is detected using a probe based detection step.

In one aspect, a second amplification product is detected in a detecting step. Detection can be probe based, sequencing based, mass-spectrometry based, gel electrophoresis based, or other common detection technique known in the art. In one aspect, amplifications product from the secondary amplification reaction is detected using a probe based detection step. In one aspect, the probe based detection step is a real-time detection step.

In one embodiment, there is a target capture reaction mixture for use in a pre-amplification reaction method that is preferably followed by a secondary target specific amplification reaction method, wherein the reaction mixture comprises at least one target nucleic acid and at least one amplification oligomer complex. In one aspect, the target capture reaction mixture further comprising at least one solid support. In one aspect, the solid support is a magbead (magnetic bead). In one aspect, the at least one target capture oligomer is a wobble probe. (See, e.g., U.S. App. Pub. No.: 2008/0286775 A1 describing wobble probes) In one aspect, the target capture reaction mixture further comprises an imidazolium compound in an amount sufficient to provide 0.05M to 4.2M when combined with the sample.

In one embodiment, there is a pre-amplification reaction mixture for generating first amplification products, wherein the pre-amplification reaction mixture comprises an enzyme selected from the group consisting of: a polymerase, an RNA-dependent DNA polymerase, a DNA-dependent DNA polymerase, a DNA-dependent DNA polymerase, a reverse transcriptase, an RNase, or a combination thereof. In one aspect, the reaction mixture is an oligomerless reaction mixture.

In one embodiment, there is a secondary amplification reaction mixture for generating second amplification products from first amplification products, wherein the secondary amplification reaction mixture comprises a pair of amplification oligomer selected from the group consisting of: two non-promoter primers; a promoter primer, optionally blocked at its 3'-end, and a non-promoter primer, a universal non-promoter primer that hybridizes to a universal tag sequence in a first amplification product and a prompter primer, optionally blocked at it 3'-end; a non-promoter primer and a promoter primer, optionally blocked at its 3'-end, and that hybridizes to a universal tag sequence in a first amplification product; two non-promoter primers, each that hybridize to universal tag sequences in a first amplification product; and a universal non-promoter primer that hybridizes to a first universal tag sequence in a first amplification product and a promoter primer, optionally blocked at its 3'-end, and that hybridizes to a second universal tag sequence in a first amplification product. The amplification enzymes may be provided as part of the first amplification product being transferred into the secondary target specific amplification reaction or the amplification enzymes may be part of the secondary amplification reaction mixture. In one aspect, the secondary amplification reaction mixture further comprises an enzyme selected from the group consisting of: a polymerase, an RNA-dependent DNA polymerase, a DNA-dependent DNA polymerase, a DNA-dependent DNA polymerase, a reverse transcriptase, an RNase, or a combination thereof.

The accompanying drawings, which constitute a part of the specification, illustrate some embodiments of the invention. These drawings, together with the description, serve to explain and illustrate the principles of the invention.

BRIEF DESCRIPTION OF THE DRAWINGS

The amplification oligomer complexes illustrated in the figures comprise amplification oligomer members containing universal tag sequences, and thus are referred to as TSU-complexes. This is for illustration and not limitation. Amplification oligomer complexes comprising oligomer members that do not contain universal tag sequences, e.g., DH-complexes, are, for the most part similarly configured and used.

FIG. 19 shows data obtained from an isothermal amplification of a single target ("PCA3 uniplex" panel) present in samples at $10^2$, $10^4$ and $10^6$ copies per reaction, and of two targets ("PCA3/PSA duplex (oligos)" panel) present in samples at $10^6$ copies per reaction, in which amplification products were detected in real time by using a fluorescent-labeled probe. For both panels, the x-axis shows cycles of amplification and the y-axis shows fluorescence units.

DETAILED DESCRIPTION

Figure 1:
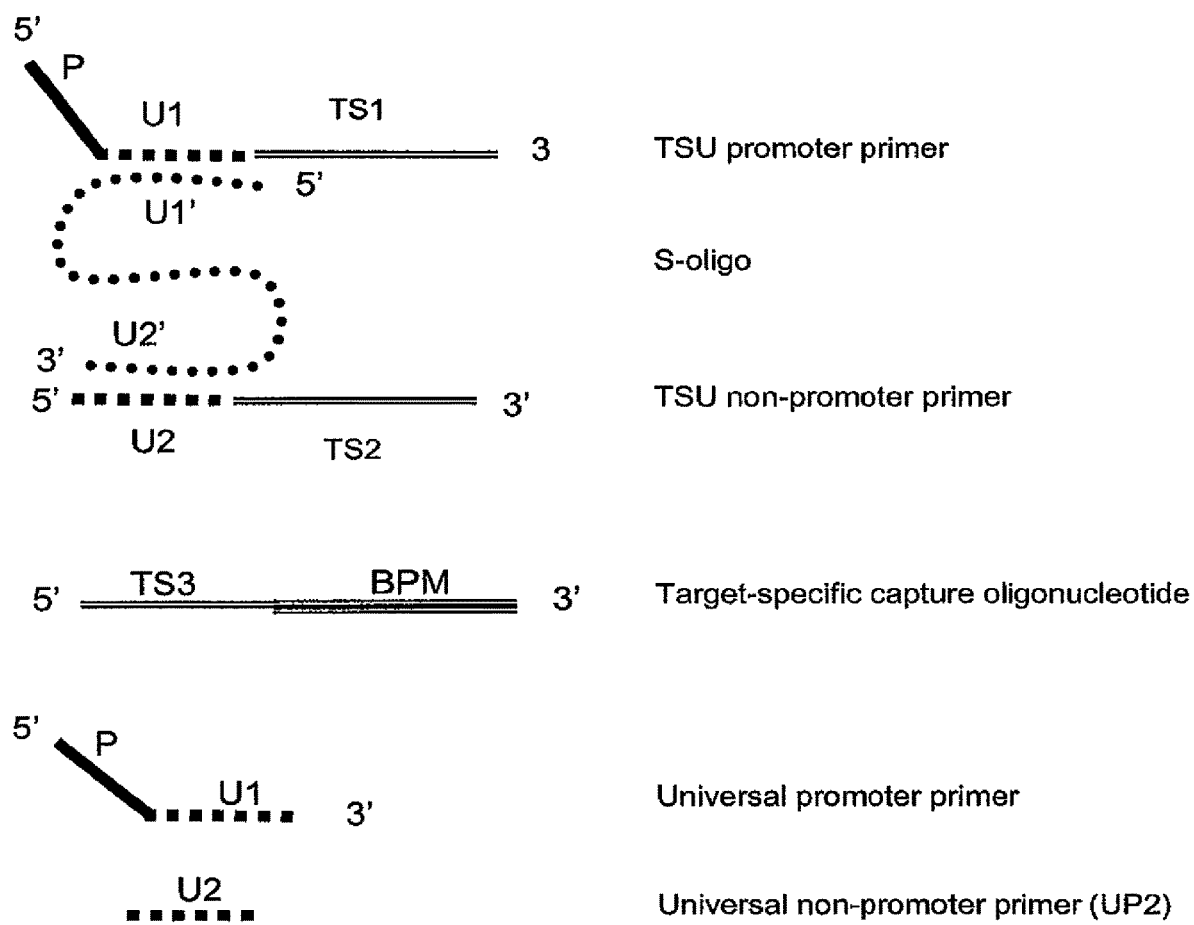
FIG. 1 is a schematic drawing showing: a three-component target-specific universal (TSU) primer complex that includes a TSU promoter primer made up of a 5' promoter sequence (solid line) labeled P, a universal sequence (dashed line) labeled U1, and a 3' target-specific sequence (double lines) labeled TS1, which is hybridized to an S-oligonucleotide (S-shaped dotted line) that includes a 5' universal sequence labeled U1' and a 3' universal sequence labeled U2', which is hybridized to a TSU non-promoter primer made up of a 5' universal sequence (dashed line) labeled U2 and a 3' target-specific sequence (double line) labeled TS2; a target-specific capture oligonucleotide made up of a 5' target-specific sequence (double line) labeled TS3 and a 3' binding pair member (triple line) labeled BPM; a universal promoter primer (UP1) made up of a 5' promoter sequence (solid line) labeled P and a 3' universal sequence (dashed line) labeled U1; and a universal non-promoter primer (UP2) made up of a universal sequence (dashed line) labeled U2.

Methods and compositions are disclosed that are useful for amplifying target nucleic acid sequences in vitro in substantially isothermal conditions to produce amplified sequences that can be detected to indicate the presence of the target nucleic acid in a sample. The methods and compositions are useful for synthesizing amplified nucleic acids to provide useful information for making diagnoses and/or prognoses of medical conditions, detecting the purity or quality of environmental and/or food samples, or investigating forensic evidence. The methods and compositions are advantageous because they allow synthesis of a variety of nucleic acids to provide highly sensitive assays over a wide dynamic range that are relatively rapid and inexpensive to perform, making them suitable for use in high throughput and/or automated systems. The methods and compositions are useful for assays that simultaneously analyze multiple different genetic sequences, i.e., multiplex amplification systems. Preferred compositions are provided in kits that include defined assay components that are useful because they allow a user to efficiently perform methods that use the components together in an assay to amplify desired targets.

The disclosed compositions and methods increase the efficiency of isothermal amplification of nucleic acids, which is particularly useful in multiplex assays that amplify multiple analytes in a single reaction mixture, e.g., for array-based assays. Multiplex isothermal transcription based amplification assays are often limited to amplification of about six or fewer analyte targets in a single reaction because of primer/primer interactions and spurious product formation, which result in inefficient amplification of one or more of the targets, thereby decreases assay sensitivity. Although design and testing of many different primers and primer combinations may improve amplification efficiency in certain multiplex assays, the disclosed systems minimize the common problems encountered in multiplex reactions by using target-specific primers in an initial phase of amplification followed by use of universal primers to amplify all of target amplicons in a second phase of amplification. Thus, amplification efficiency increases while the need to design and test many individual primers or primer combinations in multiplex reactions decreases. That is, for each desired target only one or a pair of amplification oligomer complexes unique to the desired target are designed for use in an initial amplification phase, and a subsequent amplification phase uses universal reagents that are used in common for amplification of many targets. The disclosed methods are versatile and may be used to detect a single target or multiple different targets, all amplified in a single reaction, from which amplification products may be detected at the end of a reaction (end-point detection) or during the reaction (real-time detection). Typically, the amplification oligomer primers and/or providers are provided in a target capture reagent (TCR), preferably as an amplification oligomer complex, and so these complexed oligomers and the target capture oligomers are hybridized to a target nucleic acid, and isolated along with during the target capture step. Then, an initial phase of amplification is then performed. One advantage is that by hybridizing the amplification oligomer complex to the target nucleic acid during target capture, the captured nucleic acids can be washed to remove sample components, such as unhybridized amplification oligomer complexes. In a multiplex reaction, removing unhybridized amplification oligomers allows the multiplex amplification reaction to occur without interference from these excess amplification oligomers, thereby substantially reducing or eliminating the problems common to multiplex reactions. Further, if the amplification oligomer complex comprises one or more members comprising a universal tag sequence, then the U sequences are incorporated into the initial amplification products, thereby allowing for subsequent amplification using universal primers specific for these universal sequences. Furthermore, following initial multiplex amplification, such as a pre-amplification using a amplification oligomer complex, the pre-amplified sample can be split into two or more secondary amplification reactions each comprising specific amplification oligomer for each of the targets. This multiplex pre-amplification followed by secondary target specific amplification is an advantageous use of the amplification oligomer complexes. For one, the multiplex pre-amplification uses only the amplification oligomers hybridized to target nucleic acids; unhybridized amplification oligomers are removed from the reaction. This substantially reduces or eliminates interference in the reaction caused by the amplification oligomers for the various targets. Pre-amplification then generates a plurality of RNA transcripts from each of the target nucleic acid using the amplification oligomer complex as is described herein. These RNA transcripts are then split into a plurality of secondary amplification reactions, each having a single set of target specific amplification oligomers for the isothermal amplification of one of the species of RNA transcripts. Thus, in the secondary amplification reaction, there is again no interference from having a plurality of amplification oligomer pairs in the reaction, as would occur with a multiplex reaction. Further, because the pre-amplification reaction had no excess oligomers, interfering oligomers are not transferred into the target specific secondary amplification, here too avoiding the problems common in multiplex reactions, such as is the case with two-step multiplex reactions in the art.

Unless otherwise described, scientific and technical terms used herein have the same meaning as commonly understood by those skilled in the art of molecular biology based on technical literature, e.g., *Dictionary of Microbiology and Molecular Biology*, 2nd ed. (Singleton et al., 1994, John Wiley & Sons, New York, N.Y.), or other well-known technical publications related to molecular biology. Unless otherwise described, techniques employed or contemplated herein are standard methods well known in the art of molecular biology. To aid in understanding aspects of the disclosed methods and compositions, some terms are described in more detail or illustrated by embodiments described herein.

Nucleic acid refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions. Nitrogenous bases may be conventional bases (A, G, C, T, U), analogs thereof (e.g., inosine; *The Biochemistry of the Nucleic Acids* 5-36, Adams et al., ed., 11th ed., 1992), derivatives of purine or pyrimidine bases (e.g., $^{N4}$-methyl deoxygaunosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121). Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, *Biochemistry* 43(42):13233-41).

The interchangeable terms "oligonucleotide" and "oligomer" refer to nucleic acid polymers generally made of less than 1,000 nucleotide (nt), including those in a size range having a lower limit of about 2 to 5 nt and an upper limit of about 500 to 900 nt. Preferred oligomers are in a size range having a 5 to 15 nt lower limit and a 50 to 500 nt upper limit, and particularly preferred embodiments are in a size range having a 10 to 20 nt lower limit and a 25 to 150 nt upper limit Preferred oligonucleotides are made synthetically by using any well-known in vitro chemical or enzymatic method, and may be purified after synthesis by using standard methods, e.g., high-performance liquid chromatography (HPLC). Representative oligonucleotides discussed herein include, non-promoter primers, promoter primers, promoter providers (which are promoter primers comprising a blocked 3'-end), detection probe oligomers, target capture oligomers, and blockers, to name a few. Promoter primers, promoter providers and non-promoter primers are amplification oligomers. An amplification oligomer complex is two of these amplification oligomers directly or indirectly joined together, as is discussed below. Thus, an amplification oligomer complex is made of a first amplification oligomer member and a second amplification oligomer member that are joined together. Additionally, amplification oligomers can have universal tag sequences, as is also described herein. These universal tag nucleotide sequences are present on one or both of the first and second amplification oligomers. The universal tag sequences present on first and second amplification oligomer members can be identical sequences, substantially identical sequences or different sequences. Further, for multiplex amplification reactions wherein there are two or more different first amplification oligomer members and two or more different second amplification oligomer members, individually each amplification oligomer member can have a tag sequence. If more than one amplification oligomer member for the multiplex amplification reaction has a tag sequence, they may be identical, substantially identical, different or a combination thereof, when the tag sequences are compared one to another. Similarly, amplification oligomer complexes can have amplification oligomer members that have tag sequences, and the tag sequences can be identical, substantially identical or different. Same for a multiplex amplification reaction wherein there are two or more different amplification oligomer complexes, one or more amplification oligomer members can have a tag sequences and the tag sequences can be identical, substantially identical or different when compared one to another. Tag sequences are also referred to as "U" sequences for universal.

Oligonucleotides that are not extended enzymatically include promoter provider oligomers and blocker oligomers. These oligomers hybridize to a target nucleic acid, or its complement, but do not participate in an in vitro nucleic acid amplification reaction wherein new nucleic acid strands are synthesized from a template strand by using an end of the promoter provider or blocker as an initiation point for a nucleic acid synthesis that is catalyzed by enzymatic polymerase activity. To prevent enzymatic extension of an oligonucleotide, the 3'-terminus of the oligonucleotide can be chemically or structurally blocked using a blocking moiety, as is generally known in the art. Blocked oligonucleotides are described in, e.g., U.S. Pat. Nos. 5,399,491, 5,554,516, 5,824,518, and US App. No. 2006-0046265. A blocked oligonucleotide refers to an oligonucleotide that includes a chemical and/or structural modification that is usually near or at the 3' terminus and that prevents or impedes initiation of DNA synthesis from the oligonucleotide by enzymatic means. Examples of such modifications include use of a 3'2'-dideoxynucleotide base, a 3' non-nucleotide moiety that prevents enzymatic extension, or attachment of a short sequence in 3' to 5' orientation to the oligonucleotide to make a final oligonucleotide with two 5' termini (i.e., a first 5' to 3' oligonucleotide attached to a second, usually shorter, 5' to 3' oligonucleotide by covalently joining the oligonucleotides at their 3' termini). Another example of a modification is a "cap" made up of a sequence that is complementary to at least 3 nt at the 3'-end of the oligonucleotide such that the 5'-terminal base of the cap is complementary to the 3'-terminal base of the oligonucleotide. Although blocked oligonucleotides are not extended synthetically, they may participate in nucleic acid amplification, e.g., by hybridizing to a specific location on a nucleic acid template strand to impede synthesis of a complementary strand beyond the position at which the blocked oligonucleotide is bound. Amplification oligonucleotides that are extended enzymatically include primers and promoter-primers. Universal primers (UP) contain a sequence used to amplify an initial amplification product (or analyte) sequence containing a universal or tag sequence that has been incorporated into the initial amplification product. Universal primers (UP) may contain only a nucleotide sequence that is substantially complementary to a universal sequence. A UP may further contain a nucleotide sequence, such as a promoter sequence. UP sequences may also comprise blocked 3' termini. Terms such as "universal non-promoter primer" "universal promoter provider" or "universal promoter primer" may be used to distinguish between different UP types.

Sizes of the amplification oligonucleotides are generally determined by the function portions that are included in the oligonucleotide. Component portions of a promoter primer or promoter provider oligonucleotide include a promoter sequence specific for a RNA polymerase (RNP). RNP and their corresponding promoter sequences are well known and may be purified from or made synthetically in vitro by using materials derived from a variety of sources, e.g., viruses, bacteriophages, fungi, yeast, bacteria, animal, plant or human cells. Examples of RNP and promoters include RNA polymerase III and its promoter (U.S. Pat. No. 7,241,618), bacteriophage T7 RNA polymerase and its promoter or mutants thereof (U.S. Pat. Nos. 7,229,765 and 7,078,170), RNA polymerase and promoter from *Thermus thermophilus* (U.S. Pat. No. 7,186,525), RNA polymerases from HIV-1 or HCV, and plant directed RNPs (U.S. Pat. No. 7,060,813). A promoter primer or provider oligonucleotide includes a promoter sequence that is linked functionally to the chosen RNP. Preferred embodiments of promoter primer or promoter provider oligonucleotides include a T7 promoter sequence that is used with T7 RNP, where the promoter sequence is in the range of 25 to 30 nt, such as a promoter sequence of SEQ ID NOS. 67 or 68 (SEQ ID NO:67, aatttaatacgactcactatagggaga; SEQ ID NO:68, gaaattaatac-gactcactatagggaga). Amplification oligonucleotides that include a universal (U) portion typically include a U sequence in a range of 5 to 40 nt, with preferred embodiments in a range of 10 to 25 nt, or 10 to 30 nt, or 15 to 30 nt. Amplification oligonucleotides that include a target specific (TS) portion typically include a TS sequence in a range of 10 to 45 nt, with preferred embodiments in a range of 10 to 35 nt or 20 to 30 nt. Amplification oligonucleotides that include multiple U sequences and/or multiple TS sequences will be in a size range that is determined by the length of its individual functional sequences, e.g., a promoter primer or provider oligonucleotide that includes a U sequence and a TS sequence will be the sum of the sizes of the promoter, U and TS sequences, and may optionally include linking nucleotides or non-nucleotide portions (e.g., abasic linkers). Amplification oligonucleotides made up of multiple functional components as described herein may be covalently linked by standard phosphodiester linkages, nucleic acid analog linkages, or non-nucleic acid linkages directly between the different functional portions or may be covalently linked together by using additional nucleic acid sequences or non-nucleic (e.g., abasic linkages) compounds that serve as spacers between functional portions. Some embodiments of amplification oligonucleotides may be linked together to form a complex by using non-covalent linkages, such as by using interactions of binding pair members between the oligonucleotides, which includes direct hybridization of complementary sequences contained in two or more oligonucleotides, or via a linking component to which the individual binding pair member of an oligonucleotide binds (e.g., a binding pair member for each oligonucleotide attached to a support).

A promoter provider oligonucleotide refers to an oligonucleotide that contains a promoter sequence usually on an oligonucleotide that includes a first region that hybridizes to a 3'-region of a DNA primer extension product (e.g., a cDNA) to form a hybridization complex between the promoter provider oligonucleotide and the extension product, and a second region, located 5' to the first region, that is a promoter sequence for an RNA polymerase. By forming the hybridization complex with the extension product, the promoter provider oligonucleotide can serve as a template for making a dsDNA that includes a functional promoter when the extension product or cDNA is used as a template for further strand synthesis, i.e., by extending a newly synthesized strand made from using the cDNA as a template and using the promoter sequence of the promoter provider oligonucleotide as a template, a substantially double-stranded structure that contains a functional promoter is synthesized in vitro.

Amplification of a nucleic acid refers to the process of creating in vitro nucleic acid strands that are identical or complementary to a complete or portion of a target nucleic acid sequence, or a universal or tag sequence that serves as a surrogate for the target nucleic acid sequence, all of which are only made if the target nucleic acid is present in a sample. Typically, nucleic acid amplification uses one or more nucleic acid polymerase and/or transcriptase enzymes to produce multiple copies of a target polynucleotide or fragments thereof, or of a sequence complementary to the target polynucleotide or fragments thereof, or of a universal or tag sequence that has been introduced into the amplification system to serve as a surrogate for the target polynucleotide, such as in a detection step, to indicate the presence of the target polynucleotide at some point in the assay. In vitro nucleic acid amplification techniques are well known and include transcription-associated amplification methods, such as transcription mediated amplification (TMA) or nucleic acid sequence based amplification (NASBA), and other methods such as the Polymerase Chain Reaction (PCR), reverse transcriptase-PCR, replicase mediated amplification, and the Ligase Chain Reaction (LCR).

To aid in understanding some of the embodiments disclosed herein, the TMA method that has been described in detail previously (e.g., U.S. Pat. Nos. 5,399,491, 5,554,516 and 5,824,518) is briefly summarized. In TMA, a target nucleic acid that contains the sequence to be amplified is provided as single stranded nucleic acid (e.g., ssRNA or ssDNA). Any conventional method of converting a double stranded nucleic acid (e.g., dsDNA) to a single-stranded nucleic acid may be used. A promoter primer binds specifically to the target nucleic acid at its target sequence and a reverse transcriptase (RT) extends the 3' end of the promoter primer using the target strand as a template to create a cDNA copy, resulting in a RNA:cDNA duplex. RNase activity (e.g., RNaseH of RT enzyme) digests the RNA of the RNA:cDNA duplex and a second primer binds specifically to its target sequence in the cDNA, downstream from the promoter-primer end. Then RT synthesizes a new DNA strand by extending the 3' end of the second primer using the cDNA as a template to create a dsDNA that contains a functional promoter sequence. RNA polymerase specific for the functional promoter initiates transcription to produce about 100 to 1000 RNA transcripts (amplified copies or amplicons) of the initial target strand. The second primer binds specifically to its target sequence in each amplicon and RT creates a cDNA from the amplicon RNA template to produce a RNA:cDNA duplex. RNase digests the amplicon RNA from the RNA:cDNA duplex and the target-specific sequence of the promoter primer binds to its complementary sequence in the newly synthesized DNA and RT extends the 3' end of the promoter primer to create a dsDNA that contains a functional promoter to which the RNA polymerase binds and transcribes additional amplicons that are complementary to the target strand. Autocatalytic cycles that use these steps repeatedly during the reaction produce about a billion-fold amplification of the initial target sequence. Amplicons may be detected during amplification (real-time detection) or at an end point of the reaction (end-point detection) by using a probe that binds specifically to a sequence contained in the amplicons. Detection of a signal resulting from the bound probes indicates the presence of the target nucleic acid in the sample.

Another form of transcription associated amplification that uses a single primer and one or more additional amplification oligomers to amplify nucleic acids in vitro by making transcripts that indicate the presence of the target nucleic acid has been described in detail previously (US App. 2006-0046265). Briefly, this single-primer method uses a priming oligomer, a promoter oligomer (or promoter provider oligonucleotide) that is modified to prevent the initiation of DNA synthesis from its 3' end and, optionally, a binding molecule (e.g., a 3'-blocked oligomer) to terminate elongation of a cDNA from the target strand. The method synthesizes multiple copies of a target sequence by treating a target nucleic acid that includes a RNA target sequence with (i) a priming oligonucleotide which hybridizes to the 3'-end of the target sequence such that a primer extension reaction can be initiated therefrom and (ii) a binding molecule that binds to the target nucleic acid adjacent to or near the 5'-end of the target sequence. The priming oligonucleotide is extended in a primer extension reaction by using a DNA polymerase to give a DNA primer extension product complementary to the target sequence, in which the DNA primer extension product has a 3' end determined by the binding molecule and which is complementary to the 5'-end of the target sequence. The method then separates the DNA primer extension product from the target sequence by using an enzyme which selectively degrades the target sequence and treats the DNA primer extension product with a promoter oligonucleotide made up of a first region that hybridizes to a 3'-region of the DNA primer extension product to form a promoter oligonucleotide:DNA primer extension product hybrid, and a second region that is a promoter for an RNA polymerase which is situated 5' to the first region, wherein the promoter oligonucleotide is modified to prevent the initiation of DNA synthesis from the promoter oligonucleotide. The method extends the 3'-end of the DNA primer extension product in the promoter oligonucleotide:DNA primer extension product hybrid to add a sequence complementary to the second region of the promoter oligonucleotide, which is used to transcribe multiple RNA products complementary to the DNA primer extension product using an RNA polymerase which recognizes the promoter and initiates transcription therefrom. This method produces RNA transcripts that are substantially identical to the target sequence.

An embodiment of the one-primer transcription mediated amplification method synthesizes multiple copies of an RNA target sequence by hybridizing to the target RNA a primer at a location in the 3' portion of the target sequence and a 3' blocked oligomer (i.e., the blocker oligomer) at a location in the 5' portion of the target sequence. Then the DNA polymerase activity of RT initiates extensions from the 3' end of the primer to produce a cDNA in a duplex with the template strand (a RNA:cDNA duplex). The 3' blocked oligomer binds to the target strand at a position adjacent to the intended 5' end of the sequence to be amplified because the bound 3' blocked oligomer impedes extension of the cDNA beyond that location. That is, the 3' end of the cDNA is determined by the position of the binding molecule because polymerization stops when the extension product reaches the blocking molecule bound to the target strand. The RNA:cDNA duplex is separated by RNAse activity (RNase H of RT) that degrades the RNA, although those skilled in the art will appreciate that any form of strand separation may be used. A promoter provider oligomer includes a 5' promoter sequence for an RNA polymerase and a 3' sequence complementary to a sequence in the 3' region of the cDNA to which it hybridizes. The promoter provider oligomer has a modified 3' end that includes a blocking moiety to prevent initiation of DNA synthesis from the 3' end of the promoter provider oligomer. In the duplex made of the promoter provider hybridized to the cDNA, the 3'-end of the cDNA is extended by using DNA polymerase activity of RT and the promoter provider oligomer serves as a template to add a promoter sequence to the 3' end of the cDNA, which creates a functional double-stranded promoter made up of the sequence on the promoter provider oligomer and the complementary cDNA sequence made from the promoter provider template. RNA polymerase specific for the promoter sequence binds to the functional promoter and transcribes multiple RNA transcripts that are complementary to the cDNA and substantially identical to the target sequence of the initial target RNA strand. The resulting amplified RNA can cycle through the process again by binding the primer and serving as a template for further cDNA production, ultimately producing many amplicons from the initial target nucleic acid present in the sample. Embodiments of the single primer transcription associated amplification method do not require use of the 3' blocked oligomer that serves as a binding molecule and, if a binding molecule is not included the cDNA product made from the primer has an indeterminate 3' end, but amplification proceeds substantially the same as described above. Due to the nature of this amplification method, it is performed under substantially isothermal conditions, i.e., without cycles of raising and lowering incubation temperatures to separate strands or allow hybridization of primers as is used in PCR-based methods.

Detection of the amplified products may be accomplished by using any known method. For example, the amplified nucleic acids may be associated with a surface that results in a detectable physical change, e.g., an electrical change. Amplified nucleic acids may be detected in solution phase or by concentrating them in or on a matrix and detecting labels associated with them (e.g., an intercalating agent such as ethidium bromide or cyber green). Other detection methods use probes complementary to a sequence in the amplified product and detect the presence of the probe:product complex, or use a complex of probes to amplify the signal detected from amplified products (e.g., U.S. Pat. Nos. 5,424,413, 5,451,503 and 5,849,481). Other detection methods use a probe in which signal production is linked to the presence of the target sequence because a change in signal results only when the labeled probe binds to amplified product, such as in a molecular beacon, molecular torch, or hybridization switch probe (e.g., U.S. Pat. Nos. 5,118,801, 5,312,728, 5,925,517, 6,150,097, 6,849,412, 6,835,542, 6,534,274, and 6,361,945 and US Apps. 2006-0068417 A1 and US 2006-0194240 A1). Such probes typically use a label (e.g., fluorophore) attached to one end of the probe and an interacting compound (e.g., quencher) attached to another location of the probe to inhibit signal production from the label when the probe is in one conformation ("closed") that indicates it is not hybridized to amplified product, but a detectable signal is produced when the probe is hybridized to the amplified product which changes its conformation (to "open"). Detection of a signal from directly or indirectly labeled probes that specifically associate with the amplified product indicates the presence of the target nucleic acid that was amplified.

Members of a specific binding pair (or binding partners) are moieties that specifically recognize and bind each other. Members may be referred to as a first binding pair member (BPM1) and second binding pair member (BPM2), which represent a variety of moieties that specifically bind together. Specific binding pairs are exemplified by a receptor and its ligand, enzyme and its substrate, cofactor or coenzyme, an antibody or Fab fragment and its antigen or ligand, a sugar and lectin, biotin and streptavidin or avidin, a ligand and chelating agent, a protein or amino acid and its specific binding metal such as histidine and nickel, substantially complementary polynucleotide sequences, which include completely or partially complementary sequences, and complementary homopolymeric sequences. Specific binding pairs may be naturally occurring (e.g., enzyme and substrate), synthetic (e.g., synthetic receptor and synthetic ligand), or a combination of a naturally occurring BPM and a synthetic BPM.

Target capture refers to selectively separating a target nucleic acid from other components of a sample mixture, such as cellular fragments, organelles, proteins, lipids, carbohydrates, or other nucleic acids. A target capture system may be specific and selectively separate a predetermined target nucleic acid from other sample components, e.g., by using a sequence specific to the intended target nucleic acid, or it may be nonspecific and selectively separate a target nucleic acid from other sample components by using other characteristics of the target, e.g., a physical trait of the target nucleic acid that distinguishes it from other sample components which do not exhibit that physical characteristic. Preferred target capture methods and compositions have been previously described in detail (U.S. Pat. Nos. 6,110,678 and 6,534,273 and US App. 2008-0286775 A1). Preferred target capture embodiments use a capture probe in solution phase and an immobilized probe attached to a support to form a complex with the target nucleic acid and separate the captured target from other components.

A capture probe refers to at least one nucleic acid oligomer that joins a target nucleic acid and an immobilized probe by using binding pair members that may be complementary nucleic acid sequences. One capture probe embodiment binds nonspecifically to a target nucleic acid and links it to a support for separation from the sample, whereas another embodiment includes a target specific (TS) sequence that binds specifically to a sequence in the target nucleic acid and an immobilized probe-binding region that binds to an immobilized probe, e.g., by specific binding pair interaction. In embodiments in which the TS sequence and immobilized probe-binding region are both nucleic acid sequences, they may be covalently joined or may be on different oligonucleotides joined by one or more linkers Immobilized probe refers to a moiety attached to a support that joins the capture probe to a support, directly or indirectly, e.g., by joining members of a specific binding pair, which includes non-nucleic acid binding (e.g., avidin with biotin) and nucleic acid sequence hybridization Immobilized probes include an oligonucleotide attached to a support to facilitate separation of bound target from unbound material, such as other sample components and/or other oligonucleotides included in a target capture reaction mixture. A target capture (TC) complex includes the capture probe's TS sequence hybridized specifically to a sequence in the target nucleic acid and the capture probe's immobilized probe-binding region bound to an immobilized probe on a support.

Support refers to known materials, such as matrices or particles dispersed in solution, which may be made of nitrocellulose, nylon, glass, polyacrylate, mixed polymers, polystyrene, silane, metal or polypropylene. Preferred supports are magnetically attractable particles, e.g., monodisperse magnetic spheres of uniform size±5% to provide consistent results, to which an immobilized probe is joined directly (via covalent linkage, chelation, or ionic interaction), or indirectly (via one or more linkers), to provide stable attachment of the immobilized probe to the support in conditions used in the target capture reaction. Commonly, these are referred to as magnetic beads or magbeads.

Separating or purifying refers to removal of one or more components of a mixture, such as a sample, from one or more other components in the mixture. Sample components include nucleic acids in a generally aqueous solution phase, which may include cellular fragments, proteins, carbohydrates, lipids, and other compounds. Preferred embodiments separate or remove at least 70% to 80%, and more preferably about 95%, of the target nucleic acid from other components in the mixture.

Label refers to a molecular moiety or compound that can be detected or lead to a detectable response, which may be joined directly or indirectly to a nucleic acid probe. Direct labeling may use bonds or interactions to link label and probe, which includes covalent bonds, non-covalent interactions (hydrogen bonds, hydrophobic and ionic interactions), or chelates or coordination complexes. Indirect labeling may use a bridging moiety or linker (e.g. antibody, oligomer, or other compound), which is directly or indirectly labeled, which may amplify a signal. Labels include any detectable moiety, e.g., radionuclide, ligand such as biotin or avidin, enzyme, enzyme substrate, reactive group, chromophore (detectable dye, particle, or bead), fluorophore, or luminescent compound (bioluminescent, phosphorescent, or chemiluminescent label). Preferred chemiluminescent labels include acridinium ester ("AE") and derivatives thereof (U.S. Pat. Nos. 5,656,207, 5,658,737, and 5,639,604). Preferred labels are detectable in a homogeneous assay in which bound labeled probe in a mixture exhibits a detectable change compared to that of unbound labeled probe, e.g., stability or differential degradation, without requiring physical separation of bound from unbound forms (e.g., U.S. Pat. Nos. 5,283,174, 5,656,207 and 5,658,737). Methods of synthesizing labels, attaching labels to nucleic acids, and detecting labels are well known (e.g., Sambrook et al., *Molecular Cloning, A Laboratory Manual,* 2nd ed. (Cold Spring Harbor Laboratory Press, Cold Spring Harbor, N.Y., 1989), Chapt. 10; U.S. Pat. Nos. 5,658,737, 5,656,207, 5,547,842, 5,283,174, and 4,581,333).

An array refers to multiple components arranged in a two-dimensional or three-dimensional format to allow similar or identical method steps to be performed on the components substantially simultaneously. Examples of arrays are well known and include high-density microarrays or gene chips that contain 10 to thousands of oligonucleotides attached to a support in predetermined configuration. Such arrays allow performance of assay steps on all the oligonucleotides in different positions under the same conditions, e.g., hybridization of nucleic acids in a sample applied to the array or detection of specific sequences.

Sample refers to a specimen that may contain an analyte of interest, e.g., microbe, virus, nucleic acid such as a gene, or components thereof, which includes nucleic acid sequences in or derived from an analyte. Samples may be from any source, such as biological specimens or environmental sources. Biological specimens include any tissue or material derived from a living or dead organism that may contain an analyte or nucleic acid in or derived from an analyte. Examples of biological samples include respiratory tissue, exudates (e.g., bronchoalveolar lavage), biopsy, sputum, peripheral blood, plasma, serum, lymph node, gastrointestinal tissue, feces, urine, or other fluids, tissues or materials. Examples of environmental samples include water, ice, soil, slurries, debris, biofilms, airborne particles, and aerosols. Samples may be processed specimens or materials, such as obtained from treating a sample by using filtration, centrifugation, sedimentation, or adherence to a medium, such as matrix or support. Other processing of samples may include treatments to physically or mechanically disrupt tissue, cellular aggregates, or cells to release intracellular components that include nucleic acids into a solution which may contain other components, such as enzymes, buffers, salts, detergents and the like.

"Consisting essentially of" is used to mean that additional component(s), composition(s) or method step(s) that do not materially change the basic and novel characteristics of a TSU complex composition or an amplification method that uses universal sequences and TS sequences as described herein may be included in the compositions or methods. Such characteristics include the structures of TSU oligonucleotides, including complexes of multiple TSU oligonucleotides as described herein and the ability of the methods to detect one or more analytes or target nucleic acids in a sample by associating one or more universal sequences with the respective target sequences, amplifying in an in vitro condition at least one universal sequence, and detecting a response resulting from amplification of the universal sequence to indicate the presence of at least one analyte in the assayed sample. Any component(s), composition(s), or method step(s) that have a material effect on the basic characteristics of the claimed compositions and/or methods fall outside of this term.

Preferred embodiments of the disclosed methods use aspects of isothermal amplification systems that are generally referred to as transcription associated amplification methods, which have been previously described in detail (U.S. Pat. Nos. 5,399,491, 5,554,516, 5,437,990, 5,130,238, 4,868,105 and 5,124,246, PCT Nos. WO 88/01302 WO 95/03430, and WO 88/10315, and US App. 2006-0046265 A1). Examples include transcription mediated amplification (TMA) and nucleic acid sequence based amplification (NASBA). Typically, transcription-associated amplification uses an RNA polymerase to produce multiple RNA transcripts from a nucleic acid template by using a series of steps that employ an RNA polymerase, a DNA polymerase, deoxyribonucleoside triphosphates, ribonucleoside triphosphates, a template complementary amplification oligonucleotide that includes a promoter sequence, and optionally one or more other oligonucleotides, which may serve as primers. Preferred disclosed embodiments are based on TMA (U.S. Pat. Nos. 5,399,491 and 5,554,516) or one-primer transcription-associated amplification (US 2006-0046265 A1), although a person of ordinary skill in the art will understand that other amplification methods based on polymerase mediated extension of oligonucleotide sequences may be used with the compositions and/or method steps described herein.

TMA methods disclosed herein use three basic steps in a transcription-associated amplification reaction. First, a target capture (TC) step includes hybridizing one or more amplification oligomers (which may be in a linked complex and which may include a universal tag sequence) to the target nucleic acid and capturing the hybridization complex that includes the target and the primer(s) from a mixture that separates the target nucleic acid from other sample components. A target capture mixture may include multiple primers, each type specific for a different target nucleic acid that may be present in a sample mixture. During the TC step, only those primers that are specific for a target nucleic acid that is present in the sample mixture will be bound to a target and carried into the subsequent amplification steps, because primers specific for other targets that are not present in the sample will remain in solution phase and be discarded or washed away with other sample components before amplification begins using the captured target nucleic acids. Thus, extraneous oligonucleotides that might otherwise result in interference or competition for resources during amplification are eliminated before the amplification steps begin. The captured target-primer complex is used in an isothermal amplification reaction, which is described as a first phase of amplification (or initial amplification) and a second phase of amplification (or exponential amplification). In the first phase of amplification, an initiation step extends the primer attached to the target nucleic acid strand by enzymatic in vitro nucleic acid synthesis which, in some embodiments, links a universal sequence region to an initial amplicon made from the target strand which serves as a template. For example, if the target strand is RNA, a TSU primer hybridizes to the RNA and serves as an initiation site for synthesis of the cDNA strand that includes the U sequence present on the TSU primer. In the second phase of amplification, subsequent synthetic steps in the reaction use the initial amplicons, which may include the U sequence incorporated into the product in the initial phase, and amplify the initial and subsequent amplicons by using target specific primer or universal primers that hybridize to the universal sequences and are extended enzymatically by using amplicons as templates. In some embodiments, two universal sequences are introduced into the initial amplified products of the isothermal amplification reaction and those universal sequences are the targets of subsequent amplifications that use primers that contain complementary universal sequences to make more amplicons from the captured target sequence. In other embodiments, no universal sequences are introduced into the initial amplified products of the isothermal amplification reaction and subsequent amplifications use primers that contain target specific sequences to make more amplicons from the captured target sequence. In other embodiments, one universal sequence is introduced into the initial amplified products and in the second amplification phase steps, primers include one with a universal sequence specific for the introduced universal sequence and another target specific primer (TSP) that is specific for a sequence contained in the target nucleic acid strand or a complementary strand. In some embodiments, universal primers are provided in a reagent that is mixed with the captured hybridization complexes that include the target strand and TSU primer, in which the reagent also provides one or more other components used in in vitro nucleic acid synthesis (e.g., nucleotide triphosphates, enzymes, cofactors and the like) in the second phase.

Oligonucleotides are disclosed for use in preferred embodiments of the universal transcription associated amplification methods that include: (1) a target specific capture oligomer (which may be referred to as a capture probe), (2) a target-specific universal (TSU) promoter primer or TSU promoter provider, (3) a target-specific universal (TSU) non-promoter primer, (4) an optional linker oligonucleotide that may be referred to as an S-oligonucleotide which serves to link TSU primers in a complex that is hybridized via a portion of one TSU oligonucleotide to the target strand, (5) a universal promoter primer (which may be referred to as UP1), and (6) a universal non-promoter primer (which may be referred to as UP2). In some embodiments, two TSU primers are linked together into a complex that is then hybridized to a target strand by using hybridization of a TS sequence in a TSU primer to a complementary sequence on the target strand. Such linking of TSU primers may be mediated by hybridization of the TSU primers to a linking oligonucleotide, which is sometimes referred to as an S-oligonucleotide due to its serpentine shape when it non-covalently joins two TSU primers in a three-oligonucleotide complex, in which a first end sequence of the S-oligonucleotide that is complementary to and hybridized to part of a first TSU primer and a second end sequence of the S-oligonucleotide is complementary to and hybridized to part of a second TSU primer. In some embodiments, a TSU promoter primer sequence may be linked to a TSU non-promoter primer sequence without use of a S-oligonucleotide linker. For example, a TSU promoter primer sequence and TSU non-promoter primer sequence may be synthesized as a single oligonucleotide in which both functional sequences are covalently linked, either directly or indirectly, such as by using an intervening spacer oligonucleotide sequence or a non-nucleotide covalent linker compound. In other embodiments, the two TSU oligonucleotide sequences may be synthesized as separate oligonucleotides that are joined covalently by subsequently ligating then together directly or indirectly, e.g., by use of a random linker sequence. In embodiments in which multiple TSU oligonucleotides are linked non-covalently into a complex they may be synthesized as separate oligonucleotides and then joined to a single support, e.g., via binding pair members attached to the support, or the separate TSU oligonucleotides may contain complementary sequences that are directly hybridized to link the two functional TSU oligonucleotides into a complex. For example (shown below in "Embodiment a"), a first TSU oligonucleotide is synthesized to contain, in a 5' to 3' orientation, a 5' promoter sequence (P), a middle universal sequence (U1), and a 3' target specific sequence (TS1), and a second TSU oligonucleotide is synthesized to contain a 5' sequence complementary to the promoter sequence (P'), a middle universal sequence (U2), and a 3' target specific sequence (TS2). Alternatively (shown below in "Embodiment b"), the second TSU oligonucleotide may be without the U2 sequence to contain a 5' sequence complementary to the promoter sequence (P') and a 3' target specific sequence (TS2). When the two TSU oligonucleotides are mixed under hybridization conditions, they form a directly hybridized (DH) complex of TSU oligonucleotides as diagrammed below, where vertical lines (|||) indicate the hybridization of the complementary P and P' sequences.

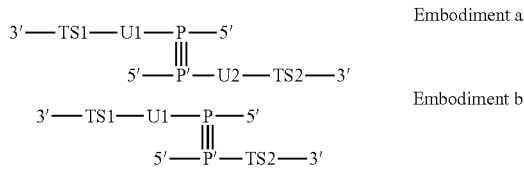

Embodiment a

Embodiment b

Figure 17:
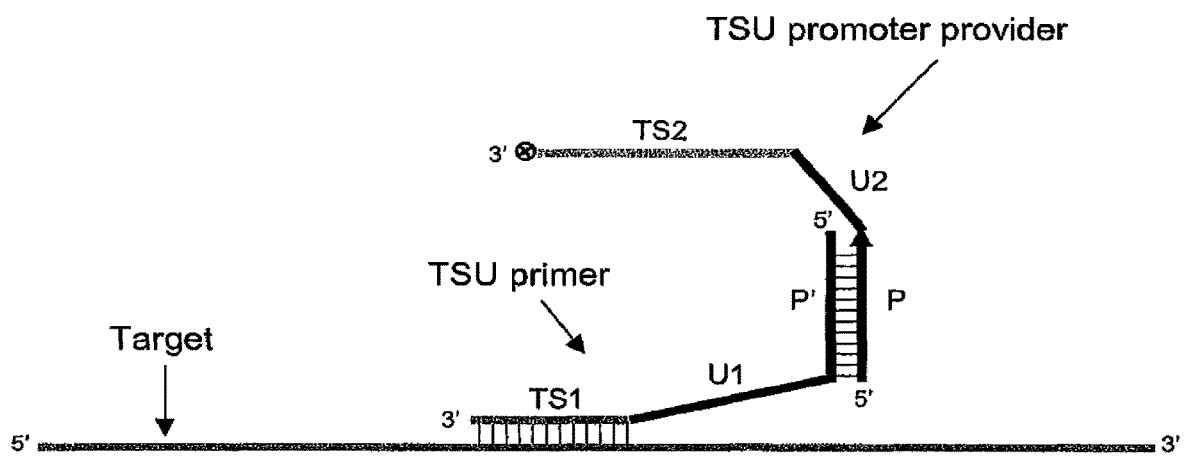
FIG. 17 is a schematic drawing of an embodiment showing two TSU oligonucleotides in a hybridization complex that is hybridized to a target strand via the TS1 sequence of a TSU primer which also includes a U1 sequence and a promoter complementary sequence (P'), which is hybridized to a TSU promoter provider oligonucleotide via hybridization of the complementary P' sequence and the P sequence of the TSU promoter provider oligonucleotide which also contains a U2 sequence, a TS2 sequence and a blocked 3' end.

A version of Embodiment a is illustrated schematically in FIG. 17 in which the two TSU oligonucleotides are shown in a hybridization complex that is hybridized to a target strand via the TS1 sequence of a first TSU primer which is hybridized via the complementary P' and P sequences to the second TSU oligonucleotide, which is a TSU promoter provider oligonucleotide with a blocked 3' end. Amplification oligomer complexes that do not include universal sequence regions are shown below in embodiment C. Embodiment c illustrated a DH-complex, wherein P is a promoter sequence and P' is a complementary promoter sequence. Direct hybridization is not limited to promoter-complementary promoter, as is illustrated herein.

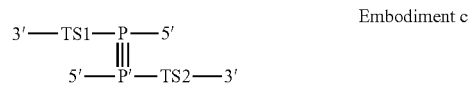

Embodiment c

Figure 18:
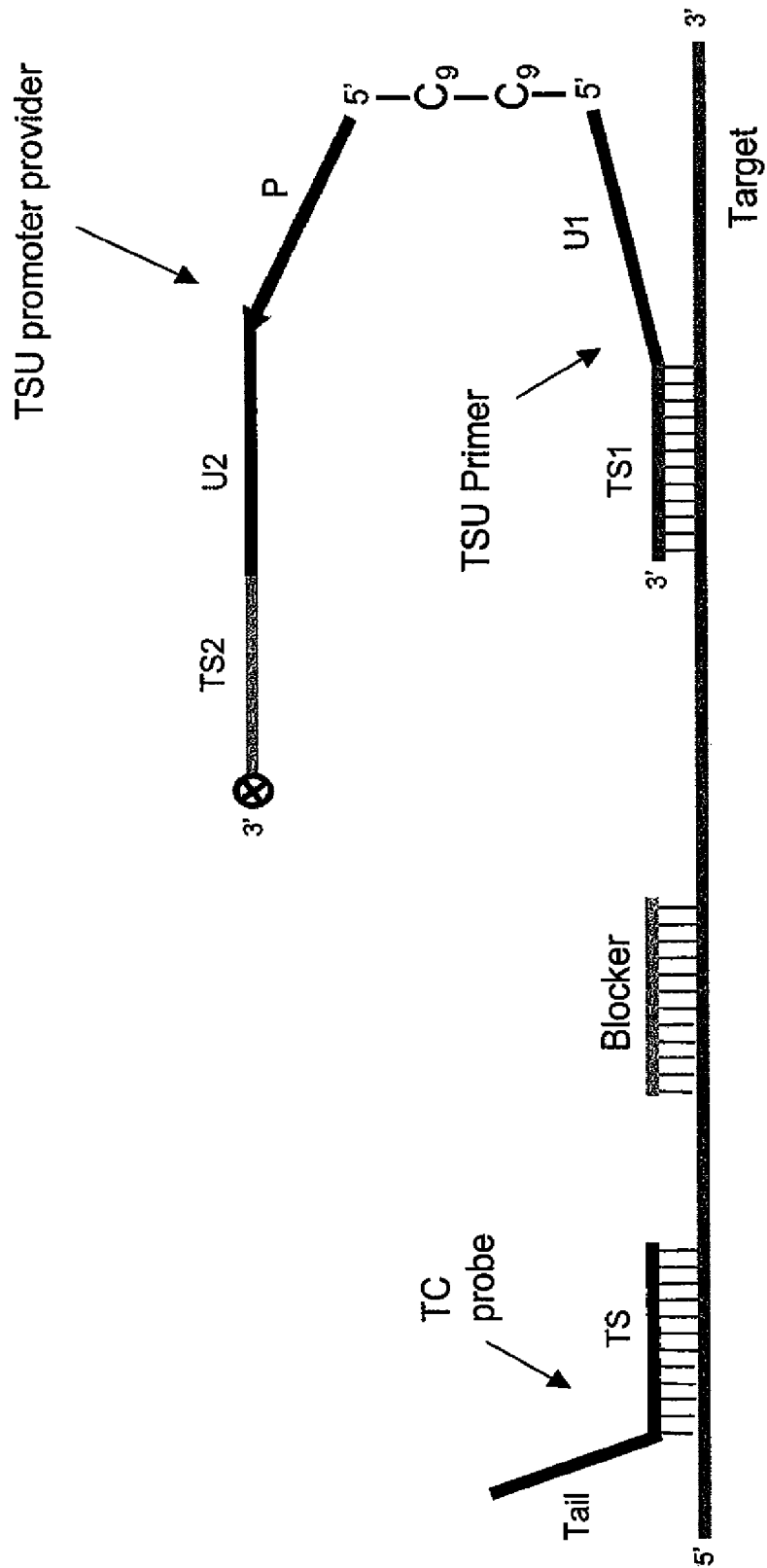
FIG. 18 is a schematic drawing of an embodiment showing two TSU oligonucleotides joined covalently via a non-nucleotide linker (—$C_9$-$C_9$—). This forms a complex made up of a TSU promoter provider that includes a blocked 3' end, and TS2, U2 and promoter (P) sequences in a 3' to 5' orientation linked to a TSU primer that includes U1 and TS1 sequences in a 5' to 3' orientation, providing one extendable 3' terminus in the complex which is hybridized to a target strand via the TS1 sequence of the TSU primer. Also shown hybridized to the Target strand are a blocker oligonucleotide and a TC probe, hybridized to the target via its TS sequence and shown with an unhybridized tail sequence.

Alternatively, two primers may be linked together covalently into a complex that is then hybridized to a target strand by using hybridization of a TS sequence in a primer to a complementary sequence on the target strand. FIG. 18 illustrates such an embodiment. This embodiment shows two TSU oligonucleotides joined covalently via a non-nucleotide linker (—C.sub.9-C.sub.9-) to form a complex made up of a TSU promoter provider that includes a blocked 3' end, and TS2, U2 and promoter (P) sequences in a 3' to 5' orientation linked to a TSU primer that includes U1 and TS1 sequences in a 5' to 3' orientation. This complex provides one extendable 3' terminus in the complex that hybridizes to a target strand via the TS1 sequence of the TSU primer. FIG. 18 also shows, hybridized to the target, a blocker oligonucleotide and a TC probe, hybridized to the target via its TS sequence. Many methods of making covalently linked primers to make a TSU primer complex are envisioned. For example, coupling after the 2 different oligos (primer and promoter primer or provider) are synthesized by using an aldehyde:hydrazine coupling pair. Other coupling pairs may be used, e.g. a carboxyl and an amine, condensed using standard carbodiimide chemistry. Alternatives for making covalently linked TSU primer complexes include constructing the entire complex on the DNA synthesizer. For example, by using standard 3' to 5' synthesis of a TSU primer, incorporation of spacers (e.g., non-nucleotide linkers or nucleotide linkers, such as poly-T), 5' to 3' synthesis of the TSU promoter primer or provider oligonucleotide by using reverse polarity phosphoramidites, and finishing the synthesis by adding a 3' blocker structure, e.g., a C added in 3' to 5' orientation. Other alternatives use the same basic strategy, but start with the TSU T7 promoter primer or provider oligonucleotide and end with the non-promoter TSU primer.

Embodiments of the amplification oligonucleotides may be used in method steps in which the TSU oligonucleotides do not form a hybridization complex or covalently linked complex of multiple functional sequence regions. That is, amplification oligonucleotides may be provided in solution phase as individual oligonucleotides or mixtures of oligonucleotides in which the individual amplification oligonucleotides function in the method steps without first forming a complex of multiple amplification oligonucleotides independent of the target nucleic acid.

In some embodiments, only one TSU oligonucleotide is used in the initial amplification phase in combination with a target specific primer (TSP) that does not contain a universal (U) sequence. For example, a TSU promoter primer or TSU promoter provider oligonucleotide may be used in combination with a TS primer, or in another example, a TSU primer may be used in combination with a promoter primer or promoter provider oligonucleotide that does not contain a U sequence. That is, only one TSU oligonucleotide is used in the initial amplification phase to introduce a U sequence into an amplicon made during in the initial phase and a TS primer is used as an initiation point for enzymatic synthesis of the initial complementary strand made from the target strand or to serve as a primer to make a strand complementary to the strand made from the target strand. In an embodiment that uses only one TSU oligonucleotide, one universal primer specific for the universal sequence introduced by the TSU oligonucleotide is used in the second phase of amplification. That is, a single universal sequence serves as the surrogate or tag sequence for that target during the second phase of amplification.

In certain embodiments in which the promoter sequence in a TSU promoter primer or promoter provider oligonucleotide is one recognized by a bacteriophage T7 RNA polymerase, the TSU promoter primer or provider may be referred to as a "TSU T7 primer" or "TSU T7 provider" oligonucleotide which may be distinguished from a TSU non-promoter primer oligonucleotide (referred to as a "TSU non-T7 primer"), and a universal primer (UP1) that includes a T7 promoter sequence may be referred to as a "T7-UP1 primer" which is distinguished from a universal primer (UP2) that does not contain a promoter sequence (referred to as a "non-T7-UP2 primer").

Embodiments of compositions and steps included in amplification methods described herein are illustrated by the figures.

Referring to FIG. 1, oligonucleotides used in methods disclosed herein are schematically drawn. At the top, a hybridization complex is illustrated that is made up of a TSU promoter primer linked non-covalently to the S-oligonucleotide which is linked non-covalently to the TSU non-promoter primer. In this complex, the TSU promoter primer is diagramed at the top as including a 5' promoter sequence (P, solid line), a middle universal sequence, U1 (dashed line), and a 3' target-specific sequence, TS1 (double line). The S-oligonucleotide is shown as an S-shaped curve (dotted line) having a 5' region that includes sequence U1' that is complementary to the universal sequence U1 of the TSU promoter primer and a 3' region that includes sequence U2' that is complementary to the universal sequence U2 of the TSU non-promoter primer. The TSU non-promoter primer is diagramed at the bottom of the complex includes a 5' universal sequence, U2 (dashed line) and a 3' target-specific sequence, TS2 (double line). Hybridization between the universal sequences of the TSU primers and the complementary sequences of the S-oligonucleotide forms the complex. Under the complex that contains the TSU primers is shown the target-specific capture oligonucleotide, which is diagramed as having a 5' target-specific region, TS3 (double line), and a 3' moiety that is a member of a specific binding pair (triple line), which in some embodiments is a homopolymeric nucleic acid sequence. Next is shown the universal promoter primer (UP1), which is diagramed as having a 5' promoter sequence region (solid line) and a 3' universal sequence region, U1 (dashed line). Next is a diagram of the universal non-promoter primer (UP2), which is shown as a universal sequence, U2 (dashed line).

In preferred embodiments, target capture and amplification oligonucleotides are provided in a minimum of reagents, to minimize the number of addition steps required to perform an assay. In one preferred embodiment, two reagent mixtures are provided as follows. A first reagent mixture, referred to as a Target Capture Reagent (TCR), comprises the TSU primers (e.g., TSU-T7 primer and TSU non-T7 primer) and all cofactors needed for their specific attachment to the desired target sequences are included (e.g., appropriate salts and buffers for hybridization when mixed with a sample that contains the target nucleic acids). The TCR also includes all of the oligonucleotides used in the target capture step, e.g., a capture probe specific for each desired target or a non-specific capture probe, a support to capture the capture probe attached to the target nucleic acid, and any intermediary oligonucleotides used in target capture, such as an immobilized probe on the support. A second reagent mixture, referred to as an Amplification Reagent (AR), provides only one set of universal primers, the universal promoter primer and the universal non-promoter primer, in addition to compounds used in in vitro nucleic acid synthesis, e.g., nucleotide triphosphates (NTPs, dNTPs), salts, buffering agents, enzyme cofactors, and enzyme(s). In another preferred embodiment, a first reagent mixture (e.g., TCR) comprises TSU primers and providers (e.g., TSU T7 providers and TSU non-T7 primers) as well as needed cofactors. Target capture oligomers are also preferably included in the TCR. A second reagent (e.g., AR) comprises universal primers and providers, as well as additional components. In another embodiment useful with amplification reactions such as PCR, a first reagent mixture (e.g., TCR) comprises TSU primers (e.g., two separate TSU non-T7 primers) as well as needed cofactors. Target capture oligomers are also preferably included in the TCR. A second reagent (e.g., AR) comprises universal primers, as well as additional components. In alternate embodiments, second reagents can comprise one universal primer or provider and one target specific primer or provider.

In use, the TCR is mixed with a sample that contains the intended target nucleic acids. The TCR that contains target capture oligonucleotides and TSU primers, or primer and provider allows all of the introduced oligonucleotides to simultaneously hybridize specifically to their respective complementary sequences for each intended target nucleic acid in the sample. By including the TSU primers, or primer and provider and the target capture oligonucleotides in the first reagent, which is mixed with the sample, the TSU complex and the capture oligonucleotide hybridized to separate sequence regions of the target nucleic acid. Then the target capture oligomer is attached to a support using first and second binding members and is then separated from other sample components, including TSU complexes that are not bound to their intended target nucleic acid, thus limiting the nucleic acids carried into the amplification step to the desired targets which are already linked to their specific TSU primers. An initial amplification product can then be synthesized using the TSU member of the TSU complex that is hybridized to the target nucleic acid, and thus the universal sequence of that TSU member is incorporated into a strand of the initial amplification product. The second member of the TSU complex then hybridizes to its target sequence on the first strands of the initial amplification product and a second strand can be synthesized, thereby incorporating the universal sequence of that TSU member into a second strand of the initial amplification product. Preferably, the first and second TSU members of the TSU complex remain linked into the complex during synthesis of the first and second strands. By remaining linked, reaction efficiencies are increased because of the proximity of the second TSU member to its target binding sequence, once formed. Amplification of the initial amplification product is then performed using universal amplification oligomers. In embodiment wherein only one of the TSU members of the TSU complex comprises a universal sequence that gets incorporated into the initial amplification product, then secondary amplification uses a universal amplification oligomer and a target specific amplification oligomer. Preferred amplification methods include TMA, PCR and other known amplification methods.

Figure 2:
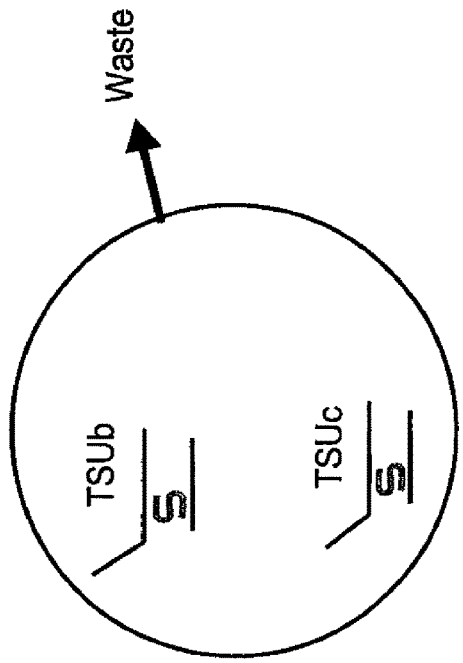
FIG. 2 is a schematic drawing illustrating target capture in which: (1) target capture reagent (TCR) contains multiple three-component target-specific universal (TSU) primer complexes (see FIG. 1) specific for three different targets (labeled TSUa, TSUb, TSUc) and capture probes specific for the three different targets in which the BPM is shown as poly-A sequences (AAA) and the target-specific sequences are labeled TSa, TSb, and TSc; (2) TCR is mixed with a sample that contains "Target a", which allows the TSUa primer complex to hybridize to Target a and the TSa capture probe to hybridize to Target a; (3) the poly-A sequence of the TSa capture probe hybridizes to an immobilized probe (poly-T sequence shown as TTTT) which is attached to a support (shaded circle), which allows the complex attached to the support to be separated from the mixture to retrieve the captured target and TSU primer complex; and (4) the portion containing the unbound TSU primer complexes (labeled TSUb and TSUb) is discarded as waste.
Figure 2:
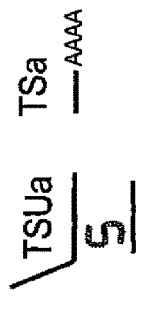
Figure 2:
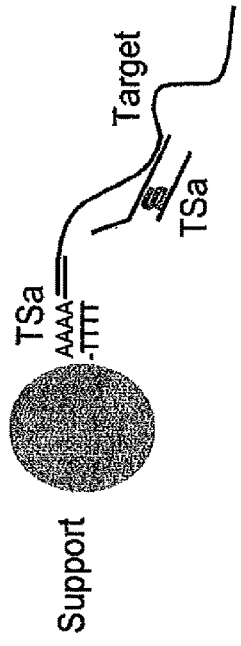
Figure 2:
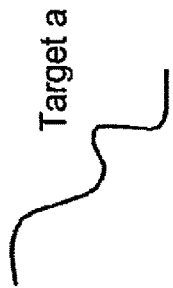

An embodiment diagramed in FIG. 2 illustrates the target capture phase of the universal isothermal amplification method that involves specific binding of a target nucleic acid in the sample to its respective TSU primers and to its respective target-specific capture oligonucleotide. FIG. 2, 1. illustrates a target capture reagent (TCR) that is a mixture of multiple different TSU primer complexes (each containing target specific sequences, TSa, TSb, and TSc, which are specific for the different targets, a, b, and c). The TCR also contains the target-specific capture oligonucleotides for each of the potential targets, with the 3' member of the binding pair shown as a poly-A sequence. The TSU primer complexes are shown as a TSU promoter primer linked via an S-oligonucleotide to a TSU non-promoter primer, and the capture oligomers are shown as a solid line and a poly-A region, both substantially as shown in FIG. 1. For each set of TSU primer complexes and capture oligomers specific for a target nucleic acid, the target-specific regions are labeled as TSa, TSb, or TSc. The TCR also contains a support with an attached immobilized moiety that binds specifically to the capture oligomers (see FIG. 2, 3.). In FIG. 2, 2., the sample which contains a target nucleic acid (Target a) is mixed with the TCR, which allows binding of the target specific sequence of the TSa capture probe to bind to its complementary sequence in Target a, and the target specific sequence of the promoter primer in the TSU primer complex to bind to its complementary sequence in Target a. The poly-A sequence of the TSa capture probe binds to its complementary poly-T sequence of the immobilized probe attached to the support, which allows the captured Target a with the TSa TSU primer complex to be retrieved from the mixture with the support (see FIG. 2, 3.). The waste products of the target capture step, following separation of the immobilized complexes on the supports, include the unbound TSU primer complexes (TSUb and TSUc primer complexes, see FIG. 2. 4.), thereby removing them from the captured target nucleic acid that is used in a subsequent amplification process.

Figure 3:
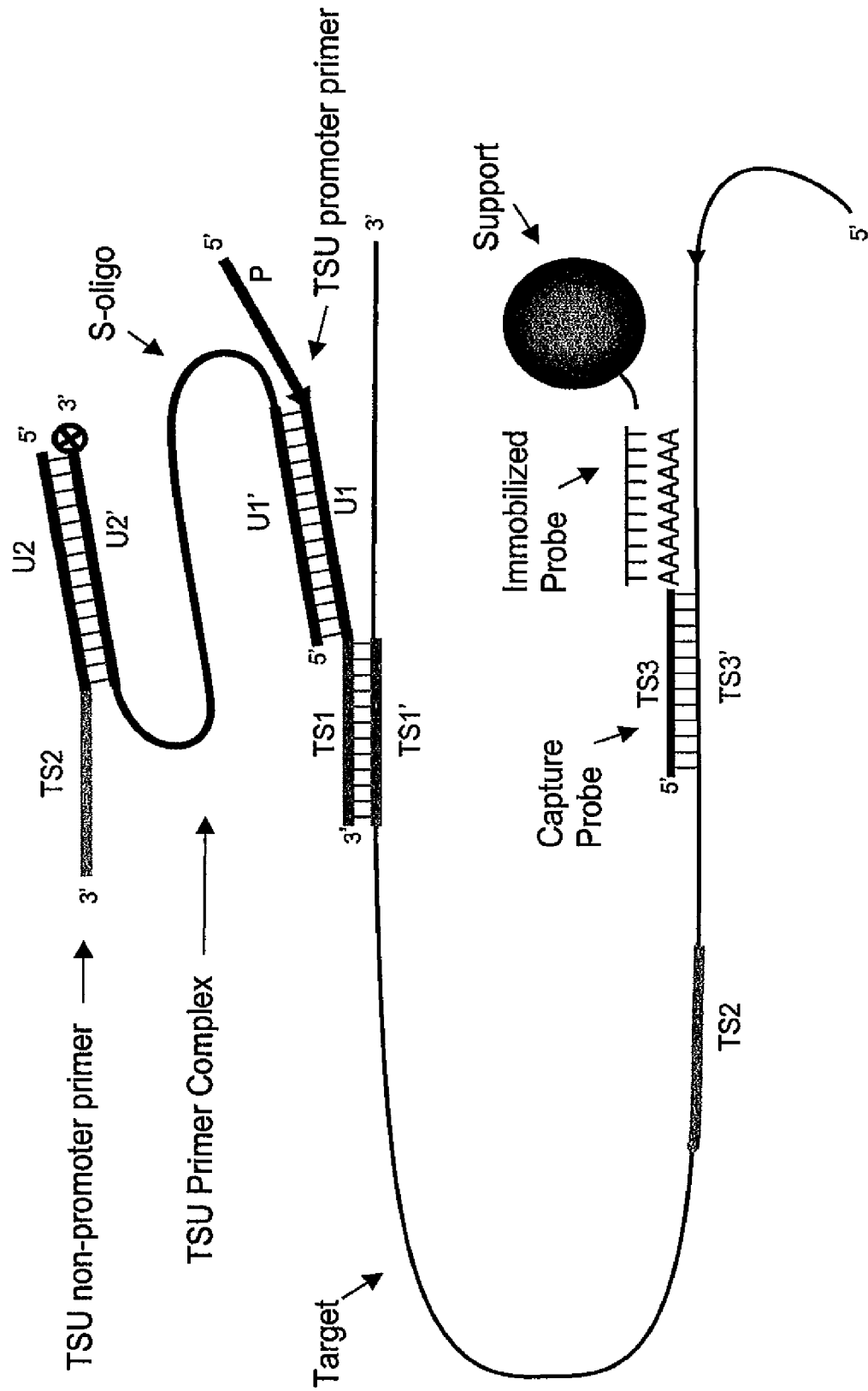
FIG. 3 is a schematic drawing that illustrates a three-component TSU primer complex which is attached to a target strand via hybridization of the TS1 sequence of the TSU promoter primer to a complementary TS1' sequence in the target nucleic acid, which is attached to a support (shaded circle) via hybridization of the target specific TS3 sequence of a capture probe to a complementary TS3' sequence of the target nucleic acid and the poly-A portion of the capture probe is hybridized to an immobilized poly-T probe that is attached to the support. Vertical connecting lines (| | | | |) indicate sequence hybridization. The TSU primer complex is made up of the TSU non-promoter primer hybridized at its U2 sequence region to the complementary U2' sequence region of the S-oligonucleotide which has a 3' blocked end (⊖) and a 5' region that is hybridized at its U1' sequence region to a complementary U1 sequence region in the TSU promoter primer that includes a 5' promoter sequence region (solid line P) and a 3' target specific sequence region (TS1) which is complementary to the TS1' sequence in the target strand. The target strand also contains another target specific sequence region (TS2) that is the same as the TS2 region of the TSU non-promoter primer. The capture probe contains a 5' target specific sequence (TS3) that is complementary to part of the target strand (sequence TS3') and a 3' poly-A sequence that is complementary to a poly-T sequence that serves as the BPM of the immobilized probe.

FIG. 3 illustrates a TSU primer complex, such as shown in FIG. 2 (3.), in more detail. The target strand is in a capture complex made up of the target strand, a capture probe that contains a 5' target specific sequence (TS3) that hybridizes specifically to a complementary target sequence (TS3') and a 3' poly-A sequence, shown hybridized to an immobilized probe that is a complementary poly-T sequence which is attached to a support. Vertical lines (| | | | |) are used to indicate hybridization between some of the complementary sequence regions. The target strand is also attached to a TSU primer complex by hybridization between the target's TS1' sequence region and the complementary target specific sequence region (TS1) of the TSU promoter primer in the TSU primer complex. The TSU primer complex is made up of the TSU non-promoter primer hybridized at its U2 sequence region to the complementary U2' sequence region of the S-oligonucleotide, which has a 3' blocked end ($\ominus$), and the 5' region of the S-oligonucleotide is hybridized at its U1' sequence region to the complementary U1 sequence region in the TSU promoter primer that includes a 5' promoter sequence region (P) and a 3' TS1 region. The target strand contains a target specific sequence region (TS2), which is identical to the target specific sequence region (TS2) of the TSU non-promoter primer. All of the target specific regions of the target strand (TS1', TS2 and TS3') are independent sequences in the target strand.

Figure 4:
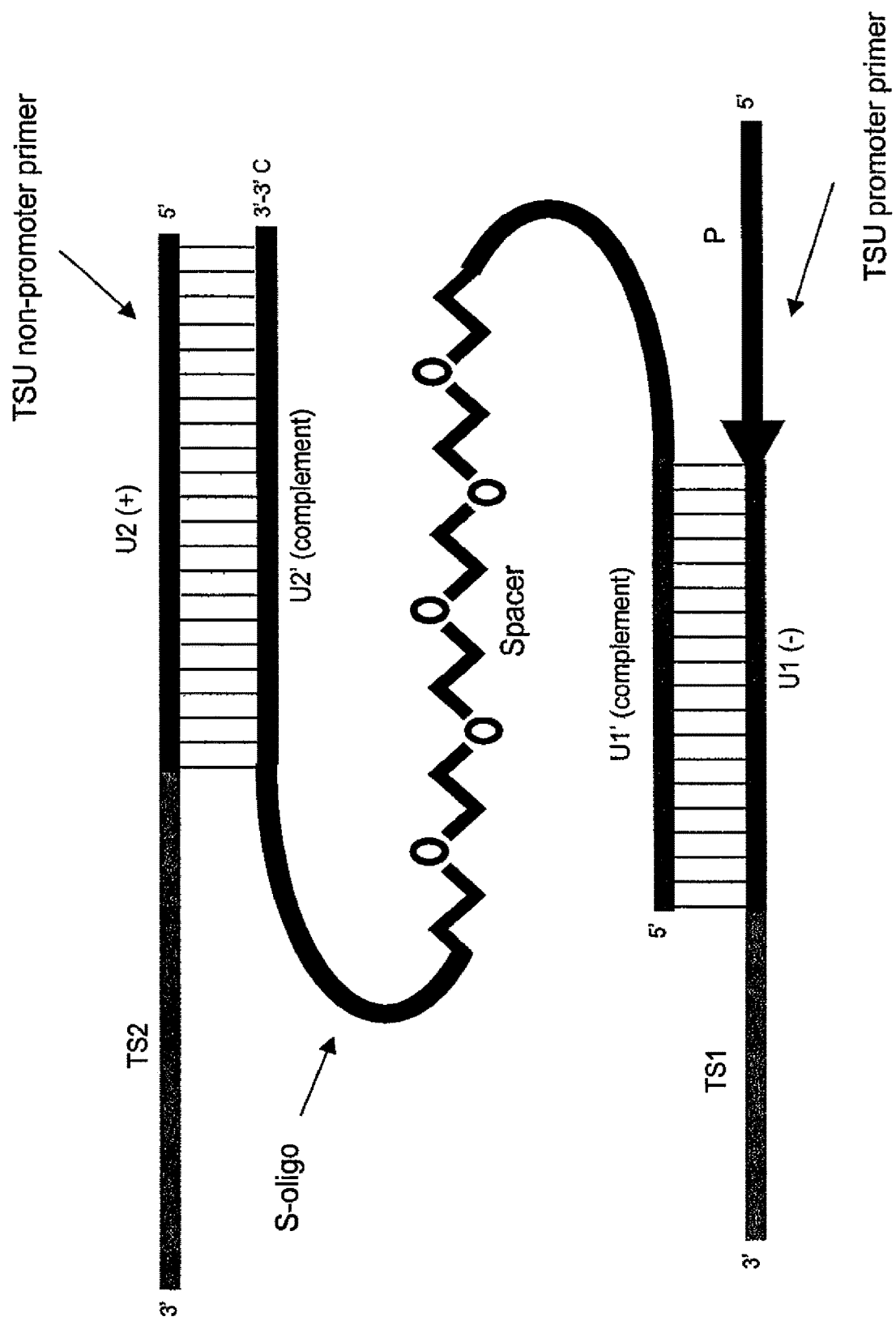
FIG. 4 is a schematic drawing that illustrates a TSU primer complex in which the upper strand is a TSU non-promoter primer made up of a 3' target specific region (TS2) and a 5' universal sequence region, labeled U2(+), which is hybridized to a complementary 3' U2' sequence region of the S-oligonucleotide (labeled S-oligo) which is contains an abasic spacer that links the 3' U2' sequence to a 5' U1' sequence region that is the complement of and hybridized to the U1 (−) sequence region in the TSU promoter primer that includes a 5' promoter sequence (P) and a 3' target specific sequence region (TS1). The illustrated S-oligonucleotide includes a 3' blocked end in which terminal bases are joined by a 3' to 3' linkage (labeled 3'-3'C) and an internal abasic compound (e.g., (C9).sub.2 or (C9).sub.3) that is a spacer that covalently joins the 5' U1' sequence and the 3' U2' sequence.

FIG. 4 illustrates a preferred embodiment of a TSU primer complex, similar to one illustrated in FIG. 3, in which the upper strand is a TSU non-promoter primer made up of a 3' TS2 region and a 5' universal sequence region, U2(+), which is hybridized to a 3' complementary U2' sequence region of the S-oligonucleotide, which has a 3' blocked end made up of a 3' to 3' C linkage. The S-oligonucleotide contains an abasic spacer that links the 3' U2' sequence region to the 5' U1' sequence region which is the complement of the U1(-) sequence region in the TSU promoter primer, to which it is hybridized. The TSU promoter primer includes a 5' promoter sequence (P) and a 3' target specific sequence region (TS1) that flank an internal U1 region. Preferred embodiments of this type of S-oligonucleotide include as the spacer an abasic compound, e.g., (C9).sub.2 or (C9).sub.3 that is covalently joined to the flanking U1' and U2' sequences.

Although FIG. 2 illustrates only three different TSU primer complexes and capture probes (labeled TSUa, TSUb, and TSUc for Targets a, b and c, respectively) and only one target nucleic acid (Target a), it will be appreciated that many different TSU complexes and capture oligonucleotides, each specific for its own respective target nucleic acid, may be included in a TCR. And a sample may include many different target nucleic acids, all of which may be selectively removed from other sample components. Thus, by including additional TSU primer complexes and probes in a TCR, but using substantially the same steps illustrated in FIG. 2, one or more different targets with attached TSU primers and capture oligonucleotides each bound specifically to their respective targets, may be separated from the mixture by using one or more supports that bind to one or more target-primer complexes selectively. For example, different size particles may be used as supports, each with a different immobilized probe that selectively binds a target specific capture probe, so that each desired target present in a single sample may be selectively removed by size separating the supports with their attached captured target and TSU primer complexes. Although FIG. 2 illustrates capture probes that include poly-A regions to hybridize to immobilized poly-T sequences, those skilled in the art will appreciate that members of any specific binding pair may be used to capture a target nucleic acid to a support, and different binding pair members may be used to selectively isolate different targets from a complex sample mixture. For example, referring to FIG. 2, the TSUa primer complexes specific to Target a, could be separated from the mixture by using a TSa capture probe that contains a ligand for receptor a in which receptor a is associated with the support as the immobilized probe. And, for example, Targets a, b, and c all contained in one sample could be associated with their respective TSU primers and separated from other sample components by using different combinations of binding pair members (BPM) on the capture probes (BPMa1, BPMb1, and BPMc1, respectively) which bind to immobilized probes via a specific binding pair partner (BPMa2, BPMb2, and BPMc2, respectively), to capture individually the targets, either all to the same support or to supports specifically for one or more targets determined by the second binding pair partner(s) associated with the support(s). For example, a capture probe for Target a associated with BPMa1 of avidin selectively removes Target a from the sample by using an immobilized probe having a BPMa2 of biotin attached to a first support, whereas in the same TCR, a capture probe for Target b is associated with a BPMb1 of an Fab fragment which selectively removed Target b by using an immobilized probe having a BPMa2 of the ligand for the Fab fragment attached to a second support, where the first and second supports are separable by standard methodologies. Supports with attached complexes that include the desired target nucleic acids may be separated from the other components in the mixture, including other sample components, such as cell debris, organelles, proteins, lipids, carbohydrates, other nucleic acids, and from unbound primers and capture probes. Any of a variety of well-known ways may be used to separate supports with attached complexes from other components in the mixture, e.g. by centrifugation, filtration, gravity separation, magnetic separation of magnetized materials, aspiration, and the like. Thus, following target capture, only TSU primers bound to their respective targets are carried into the amplification phase of the assay because unbound oligonucleotides are separated from the targets during the target capture phase. Additional washing step(s) may be included in the target capture phase to wash supports with the attached targets and primer complexes, thus further purifying the captured target nucleic acids with attached TSU primers form other sample components and unbound oligonucleotides before the amplification phase.

Figure 5:
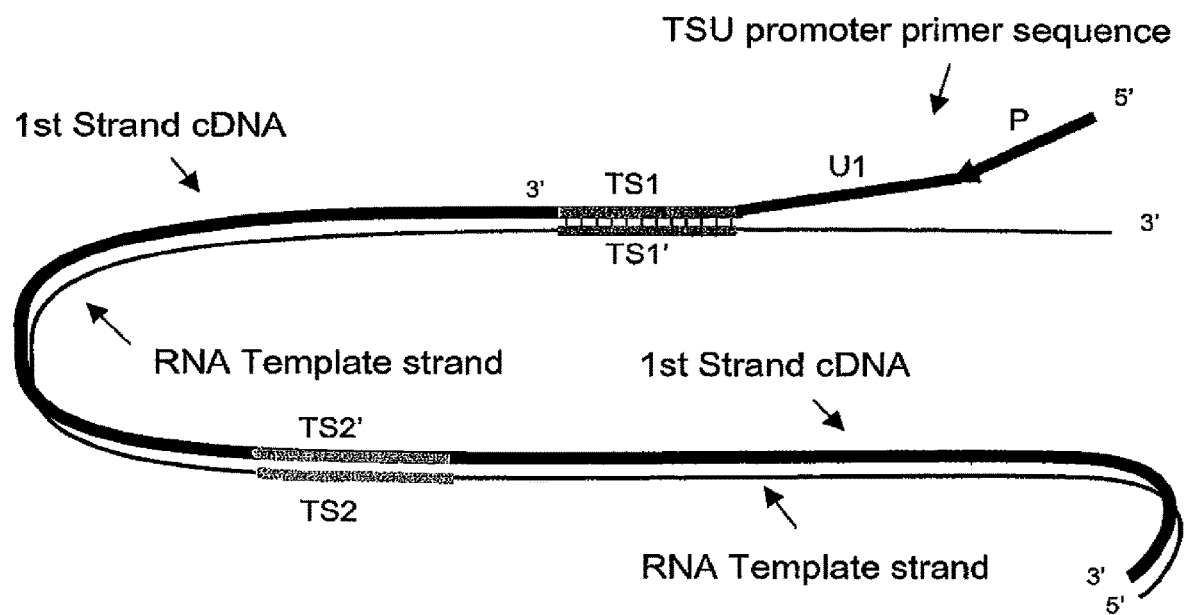
FIG. 5 is a schematic drawing that illustrates the product that results from an initial synthetic step of the initial amplification phase in which the 3' end of the TSU promoter primer, hybridized via its TS1 sequence to the complementary TS1' sequence in an RNA template strand (narrow solid line), has been synthetically extended to make a first strand cDNA (wider solid line) by using a reverse transcriptase (RT) polymerase. The RNA template strand also contains a TS2 sequence that is complementary to the TS2' sequence made in the first strand cDNA.
Figure 6:
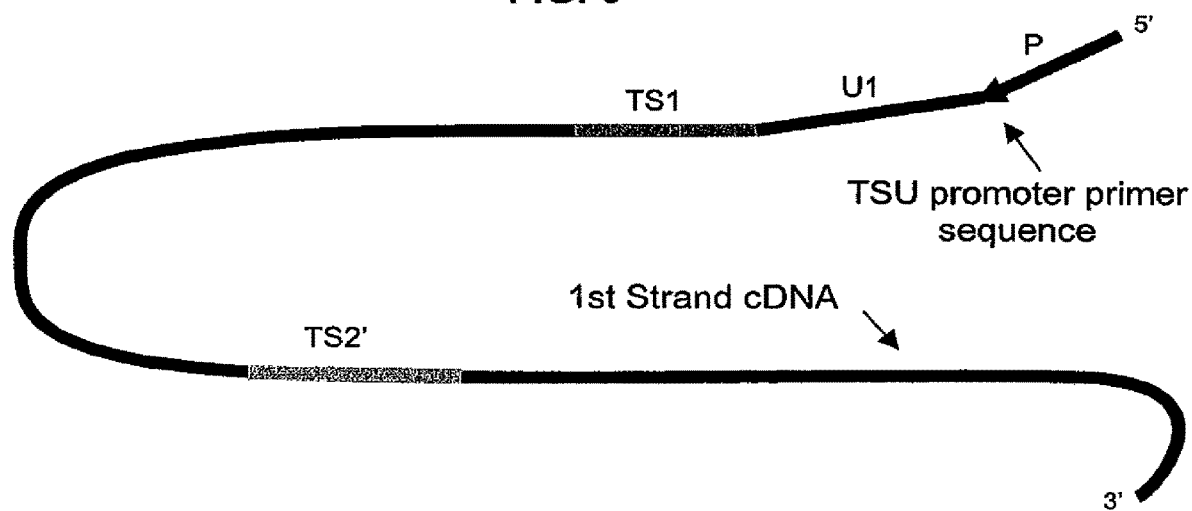
FIG. 6 is a schematic drawing that illustrates the first strand cDNA product (as shown in FIG. 5) following degradation of the RNA template strand that was shown in FIG. 5, in which the cDNA contains a 5' promoter sequence (P), a universal sequence (U1), a target-specific sequence (TS1), a cDNA sequence that was made from the template strand and that contains a second target-specific sequence (TS2').

Next, amplification is initiated by using the TSU primers specific for the intended target nucleic acids, i.e., primers carried into the amplification mixture with the captured complex that includes the target nucleic acid strand linked by hybridization to its corresponding TSU primer(s). In some preferred embodiments, the TSU primers carried into the amplification phase are in a TSU primer complex made up of a TSU promoter primer, S-oligonucleotide, and TSU non-promoter primer for the intended target (see FIG. 1 and FIG. 2). Other TSU primers specific for other analytes that were absent from the sample, and therefore not captured, are discarded in the target capture stage and are substantially absent from the amplification reaction mixture. Thus, the initial synthetic step in amplification relies on TSU primers attached specifically to the intended target nucleic acids present in at initial amplification phase. Because the TSU primers are already linked specifically to their intended target nucleic acid sequences, amplification initiates efficiently when other reaction components (e.g., enzymes and co-factors, synthetic substrates) are mixed with the captured target and its attached TSU primer or primer complex. The 3' end of the TSU promoter primer is extended synthetically as illustrated in FIG. 5 which shows the product that results from a first synthetic step in the initial amplification phase, in which the 3' end of the TSU promoter primer, hybridized at its TS1 sequence to the TS1' sequence of the target strand, has been synthetically extended to make a first strand cDNA. For simplicity, the other components of a TSU primer complex (the S-oligonucleotide and TSU non-promoter primer) have not been illustrated in FIG. 5, but it will be understood that the entire TSU primer complex may be attached to the RNA template strand during this synthetic step. Synthesis that initiates from the TSU promoter primer on the RNA template strand uses an RNA directed DNA polymerase of a reverse transcriptase (RT) enzyme supplied in the amplification reaction mixture to synthesize a complementary DNA (cDNA) strand. A preferred RT is one that includes RNAse H activity to degrade an RNA target/template strand, although the RNA dependent DNA polymerase activity and the RNA degradation activity may be supplied by different enzymes in the amplification reaction mixture. The synthesized cDNA strand contains a sequence TS2' which is complementary to the TS2 sequence in the target/template strand. Following synthesis of the cDNA, degradation of the RNA template strand occurs from the RNAse H activity in the reaction mixture, resulting in a single strand DNA that contains a 5' promoter sequence, the U1 sequence and the TS1 sequence, all supplied by the TSU promoter primer, and a 3' sequence that contains sequence complementary to the RNA template strand, including the TS2' sequence which is 3' of the TS1, U1 and P sequences. This resulting cDNA strand is shown in FIG. 6.

Figure 7:
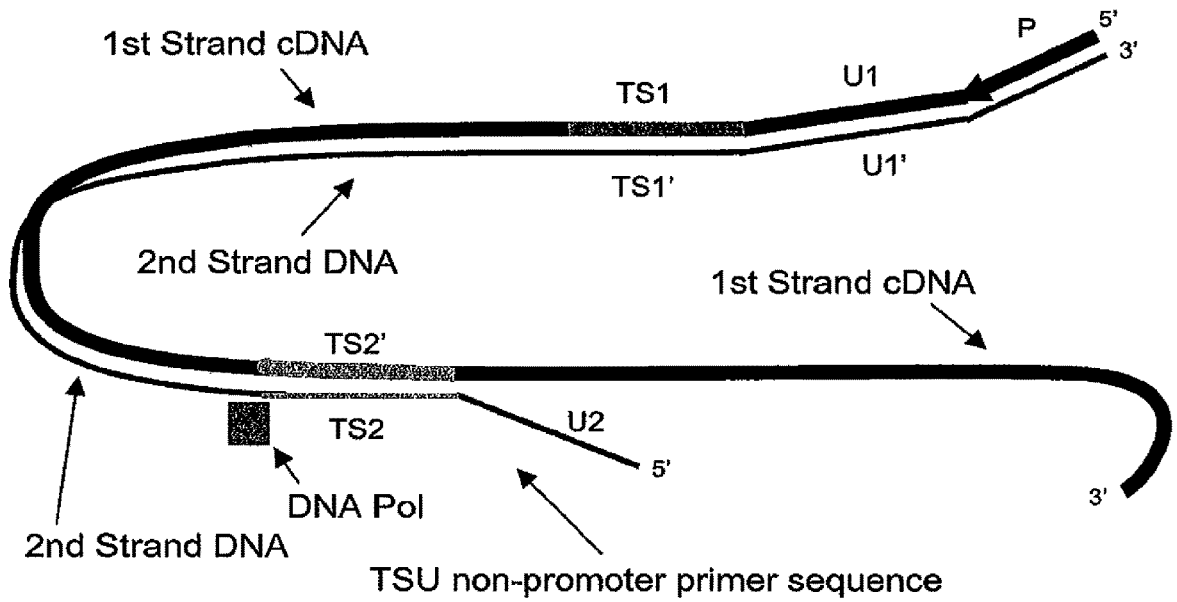
FIG. 7 is a schematic drawing that illustrates the product that results from a second synthetic step in the initial phase of amplification. This product results from hybridization of the TSU non-promoter primer to the first strand cDNA product (see FIG. 6) by hybridizing the TS2 sequence of the TSU non-promoter primer to the complementary TS2' sequence of the cDNA and extending the 3' end of the TSU non-promoter primer by using a DNA polymerase (shaded rectangle) to make a complementary second strand of DNA. The second strand contains the primer's 5' U2 sequence and TS2 sequence, the complementary sequence to the first strand cDNA which includes a target specific sequence TS1', a universal sequence U1' and a 3' sequence that is complementary to the promoter sequence of the cDNA, thus making a double-stranded DNA that contains a functional promoter sequence.

The first strand cDNA then binds to the TSU non-promoter primer by hybridization between the TS2' sequence of the cDNA and the complementary TS2 sequence of the TSU non-promoter primer, which was carried into the amplification reaction mixture as part of the TSU primer complex bound to the captured target nucleic acid. In preferred embodiments, the isothermal amplification conditions maintain the TSU non-promoter primer in a TSU primer complex (i.e., linked via the S-oligonucleotide to the TSU promoter primer) during the initial cDNA synthesis step and then the 3' TS2 portion of the TSU non-promoter primer in the complex hybridizes to the cDNA strand. Such embodiments are advantageous because they make use of efficient kinetics of hybridization that performs substantially as intramolecular hybridization because the TS2 and TS2' sequences are in close proximity due to the maintained structure of the TSU primer complex joined to the cDNA. Referring to FIG. 7, the 3' end of the TSU non-promoter primer hybridized the cDNA strand via hybridization of the TS2 and TS2' sequences is enzymatically extended by a DNA polymerase using the cDNA as a template strand to synthesize a second strand of DNA. For simplicity, FIG. 7 shows the TSU non-promoter primer without the other components of the TSU primer complex as described above, but those components may be maintained during synthesis of the second strand DNA. The second strand DNA includes a 5' universal sequence (U2) and TS2 sequence, both contributed by the TSU non-promoter primer, a DNA strand extended from the 3' end of the TSU primer, which includes a TS1' sequence and universal sequence U1' (both complementary to the TS1 and U1 sequences, respectively, of the cDNA and the TSU promoter primer), and a 3' sequence complementary to the promoter sequence (P) of the TSU promoter primer. The resulting structure is a substantially dsDNA that contains a functional promoter sequence for its respective RNA polymerase enzyme.

Figure 8:
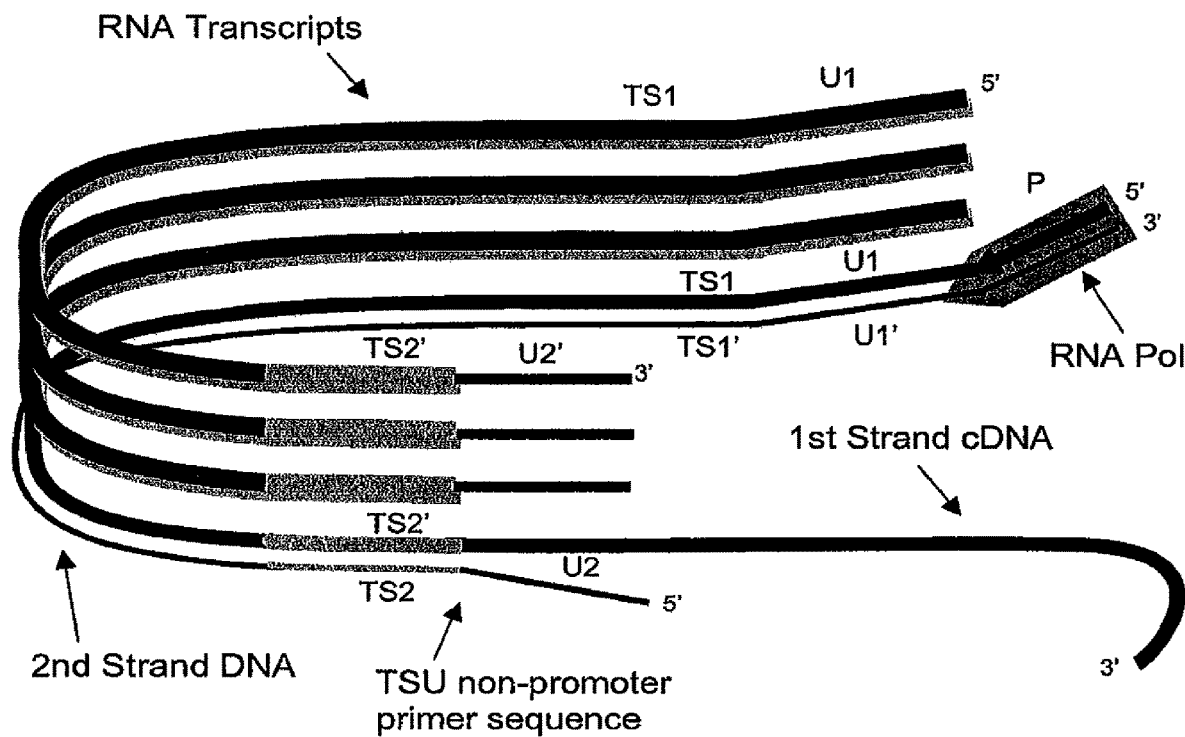
FIG. 8 is a schematic drawing that illustrates the substantially dsDNA made up of the first strand cDNA and the second strand DNA (see FIG. 7) and three RNA transcripts (broader lines) above the dsDNA. RNA transcripts are made by transcription that initiates at the functional double-stranded promoter sequence (P) by using its respective RNA polymerase (shaded area labeled RNA Pol). RNA transcripts include, in a 5' to 3' direction, a 5' U1 sequence, a TS1 sequence, a transcript from the target strand, a TS2' sequence, and a 3' U2' sequence.
Figure 9:
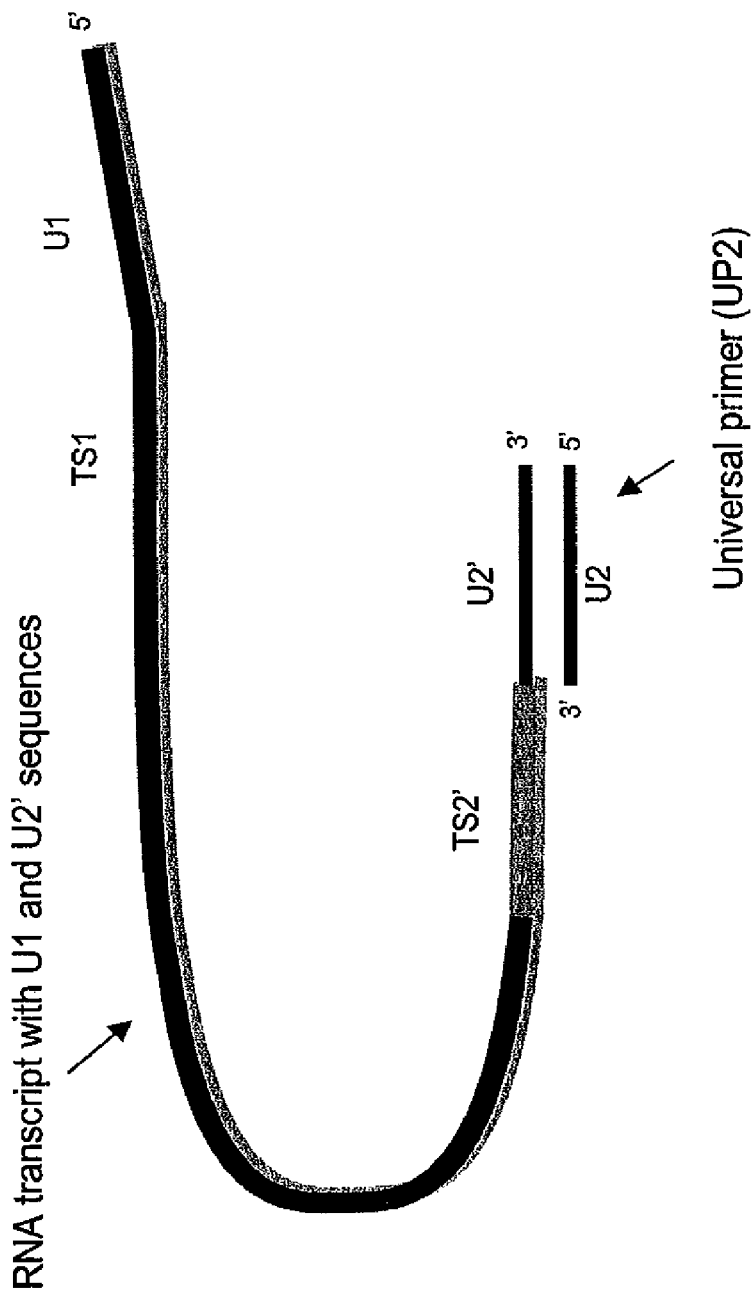
FIG. 9 is a schematic drawing showing a single RNA transcript, as illustrated in FIG. 8, from the first phase of isothermal amplification with terminal universal sequences, U1 and U2', which flank the target specific sequences TS1 and TS2', which flank the transcript of other target strand sequence, and a universal primer (UP2) that includes sequence U2 that is complementary to sequence U2' in the transcript.

Continuing the initial phase of isothermal amplification, as shown in FIG. 8, the RNA polymerase (RNA Pol) specific for the promoter sequence binds to the functional promoter and initiates transcription from the substantially dsDNA, to make multiple RNA transcripts. These transcripts include a 5' U1 sequence, followed by the TS1 sequence, additional target-specific sequence located between the TS1 and TS2' sequences, the TS2' sequence, and a 3' U2' sequence. The RNA transcripts contain target specific sequences flanked by a first universal sequence (U1), and a second universal sequence (U2'), which differ from each other (one such transcript is illustrated in FIG. 9).

Figure 10:
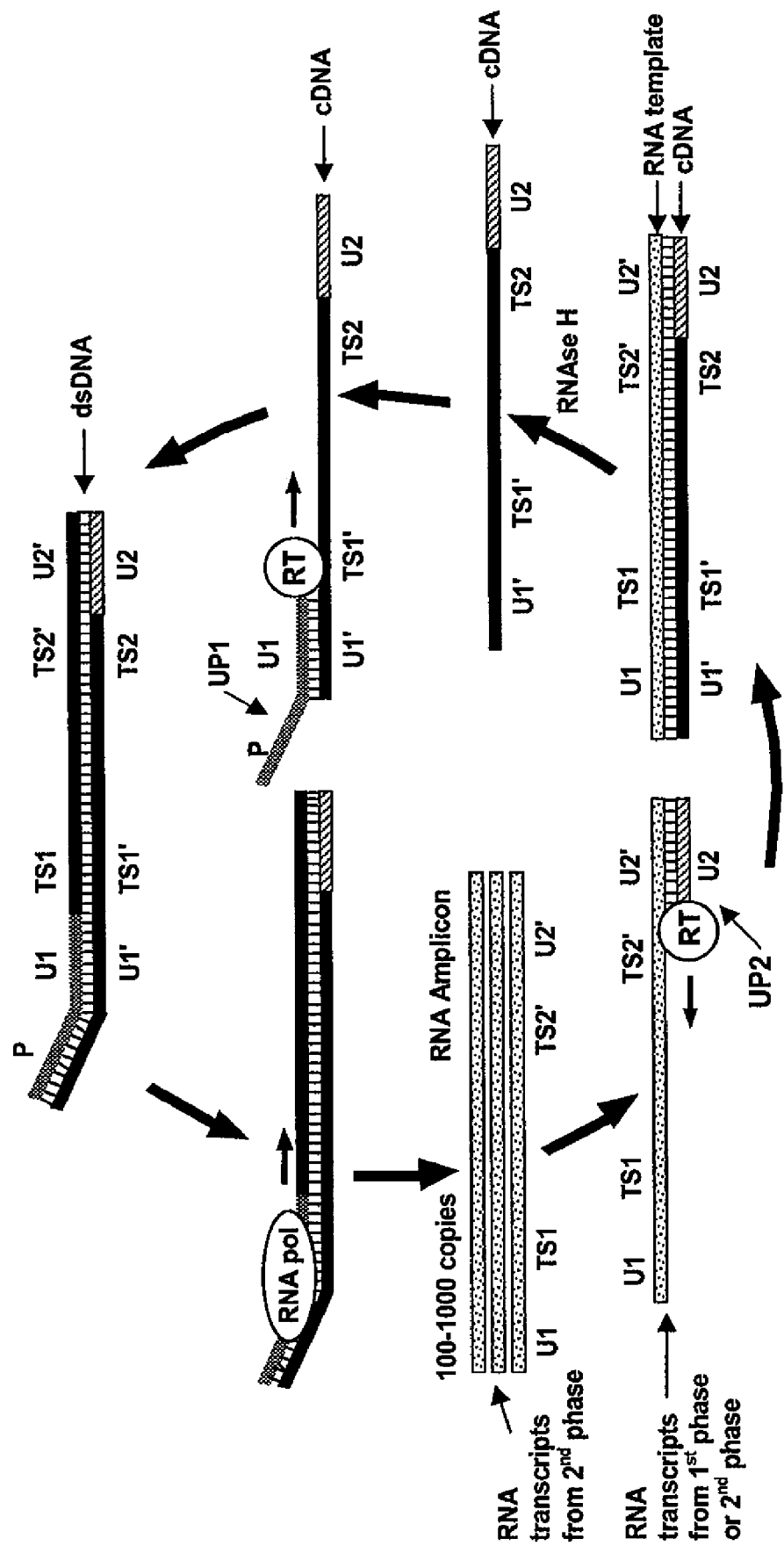
FIG. 10 is a schematic drawing showing the steps in the second phase of isothermal amplification in which RNA transcripts (as illustrated in FIG. 9) enter the system at the lower left where the RNA transcript hybridizes to the universal primer UP2 via complementary pairing of the U2' and U2 sequences (hybridization shown by vertical lines | | | | |) and reverse transcriptase enzyme (open circle labeled RT) attaches to UP2 and uses its RNA directed DNA polymerase activity to enzymatically extend the UP2 primer by using the RNA transcript as a template. The next step, after the arrow pointing to the right, shows the resulting cDNA (lower strand) hybridized to the RNA template (upper strand), which after the upward pointing arrow, is digested by RNAse H activity of the RT enzyme that leaves the cDNA strand. After the next upward pointing arrow, the cDNA is hybridized via its U1' sequence to the complementary U1 sequence of the universal promoter primer (UP1) which includes a 5' promoter sequence (P) and the UP1 primer is extended by DNA directed DNA polymerase activity of the RT enzyme to make a dsDNA that is illustrated at the top of the circle, above the arrow pointing upward and leftward. The dsDNA contains two universal sequences per strand (U1 and U2' on the upper strand and U1' and U2 on the lower strand) that flank target specific sequences (TS1, TS2' and the intervening sequence on the upper strand and TS1' and TS2 and the intervening sequence on the lower strand), and a functional promoter (P). Following the arrow downward to the left, the functional promoter interacts with a RNA polymerase (oval labeled RNA Pol) specific for the promoter sequence to make transcripts from the dsDNA, which are shown after the next downward pointing arrow, to result in 100 to 1000 transcripts or RNA amplicons which contain two universal sequences (U1 and U2') and target specific sequences (TS1 and TS2' and the intervening sequence). Following the next arrow downward and to the right, these RNA transcripts enter the amplification system and are used as templates for further isothermal amplification in a cyclic manner as shown, repeating the steps as described above for the first phase RNA transcripts.

In the second phase of amplification, universal primers (UP1 and UP2 of FIG. 1) are used to make additional RNA transcripts in a continuous cycle of isothermal amplification, using RNA transcripts as templates for synthesis of additional amplification products or amplicons. Preferred embodiments use the universal primers in an isothermal amplification reaction similar to TMA or NASBA reactions. In a first step of the second phase of amplification, a universal non-promoter primer (UP2), which consists essentially of a U2 sequence complementary to the 3' U2' sequence of the RNA transcripts produced in the first phase of amplification, hybridizes to the initial RNA transcripts (see FIG. 9). The 3' end of the UP2 primer is extended synthetically in an enzymatic isothermal reaction as illustrated in FIG. 10, in which the RNA transcripts from the initial phase of amplification enter the second phase at the lower left. The RT enzyme binds and initiates cDNA synthesis from the 3' end of the UP2 primer by using the RNA directed DNA polymerase activity and the transcript as a template. Following the dark arrows in FIG. 10 illustrates the steps in the second phase of amplification. The RNA template strand in the duplex with the cDNA is degraded by RNAse H activity, allowing the cDNA to hybridize at the U1' sequence to the complementary U1 sequence of the universal promoter primer (UP1). The RT binds to the 3' end of the UP1 primer and initiates second strand DNA synthesis by using the DNA directed DNA polymerase activity and the cDNA strand as a template strand. The resulting dsDNA contains a functional promoter sequence and, on each strand, two universal sequences flanking the target specific sequences. RNA polymerase (RNA Pol) specific for the promoter sequence binds to the functional promoter and makes 100 to 1000 transcripts (RNA amplicons) that are identical structurally to the initial RNA transcripts made in the first phase of amplification. The additional transcripts serve as templates for more iterations of the process. The RNA transcripts made in the second phase of amplification become available for use in the amplification process when they are made, i.e., no denaturation step is required, thus efficiently amplifying the universal and target specific sequences in a continuous isothermal process. RNA transcripts made during the second phase of the isothermal amplification process may be detected during the reaction (i.e., in real time) or at a designated end point of the reaction (e.g., a specific time after beginning the amplification reaction or when amplification substantially terminates due to exhaustion of substrates present in the reaction).

The RNA amplicons may be detected by using well-known detection methods which may detect simply an increase in nucleic acid concentration or may detect selected amplified sequences. For example, detection may specifically detect one or more of the universal sequence(s) or subsequence(s) thereof, or a target specific sequence(s) or a subsequence thereof, or a contiguous sequence that combines portions of universal and target specific sequences. Preferably, a detection step that uses a probe for detection of amplicons allows homogeneous detection, i.e., detection of the hybridized probe without removal of unhybridized probe from the mixture (e.g., U.S. Pat. Nos. 5,639,604 and 5,283,174,). In preferred embodiments that detect the amplified product near or at the end of the second phase of amplification, a linear probe is used to provide a detectable signal that indicates hybridization of the probe to the amplified product. In preferred embodiments that detect the amplified product in real time, the probe is preferably a probe in which signal production is linked to the presence of the target sequence, such as a molecular beacon, molecular torch, or hybridization switch probe, that is labeled with a reporter moiety that is detected when the probe binds to amplified product. Such a probe may include a label, e.g., a fluorophore attached to one end of the probe and an interacting compound, e.g., a quencher attached to another location of the probe to inhibit signal production from the label when the probe is in a "closed" conformation that indicates it is not hybridized to the amplified product, whereas detectable signal is produced when the probe is in "open" conformation that indicates it is hybridized to the amplified product. Various probe structures and methods of using them have been described previously (e.g., U.S. Pat. Nos. 5,118,801, 5,312,728, 5,925,517, 6,150,097, 6,849,412, 6,835,542, 6,534,274, and 6,361,945, US App. 2006-0068417 and PCT App WO 2006/093892).

The methods of target capture and amplification that use at least one universal sequence described herein may be performed in a variety of different ways. In some preferred embodiments, all of the steps are performed substantially in a liquid phase, i.e., one in which most or all of the steps occur with the components in the reactions being present in substantially aqueous media. For example, the steps of target capture may be performed in a substantially liquid aqueous mixture that allows hybridization of the capture probe to the target nucleic acid and the capture probe to an immobilized probe in solution phase by using immobilize probes attached to small particles or beads that are mixed or suspended in the solution phase. Similarly, in some preferred embodiments, all of the amplification steps are performed by having all of the amplification components (e.g., substrates, templates, enzymes and cofactors) in a solution phase for the entire reaction. The detection step that detects a signal resulting from the presence of amplified products may also be performed in a substantially aqueous solution phase (e.g., as described in U.S. Pat. Nos. 5,639,604 and 5,283,174). In other preferred embodiments, one or more of the steps in an assay that includes target capture, amplification and detection steps may be performed substantially attached to a solid phase, such as a support matrix or particle, to compartmentalize or localize detection of a particular analyte of interest. Such embodiments are advantageous because amplification products may be localized, e.g., temporally or spatially, for separate detection of signals resulting from the presence of one or more selected analytes present in a sample. This is particularly useful when a sample may contain multiple different analytes that are all treated in substantially the same reagent mixtures during target capture, amplification and/or detection steps, but for which separate detection of signals resulting from the presence of amplified products for each analyte is desired.

Figure 11:
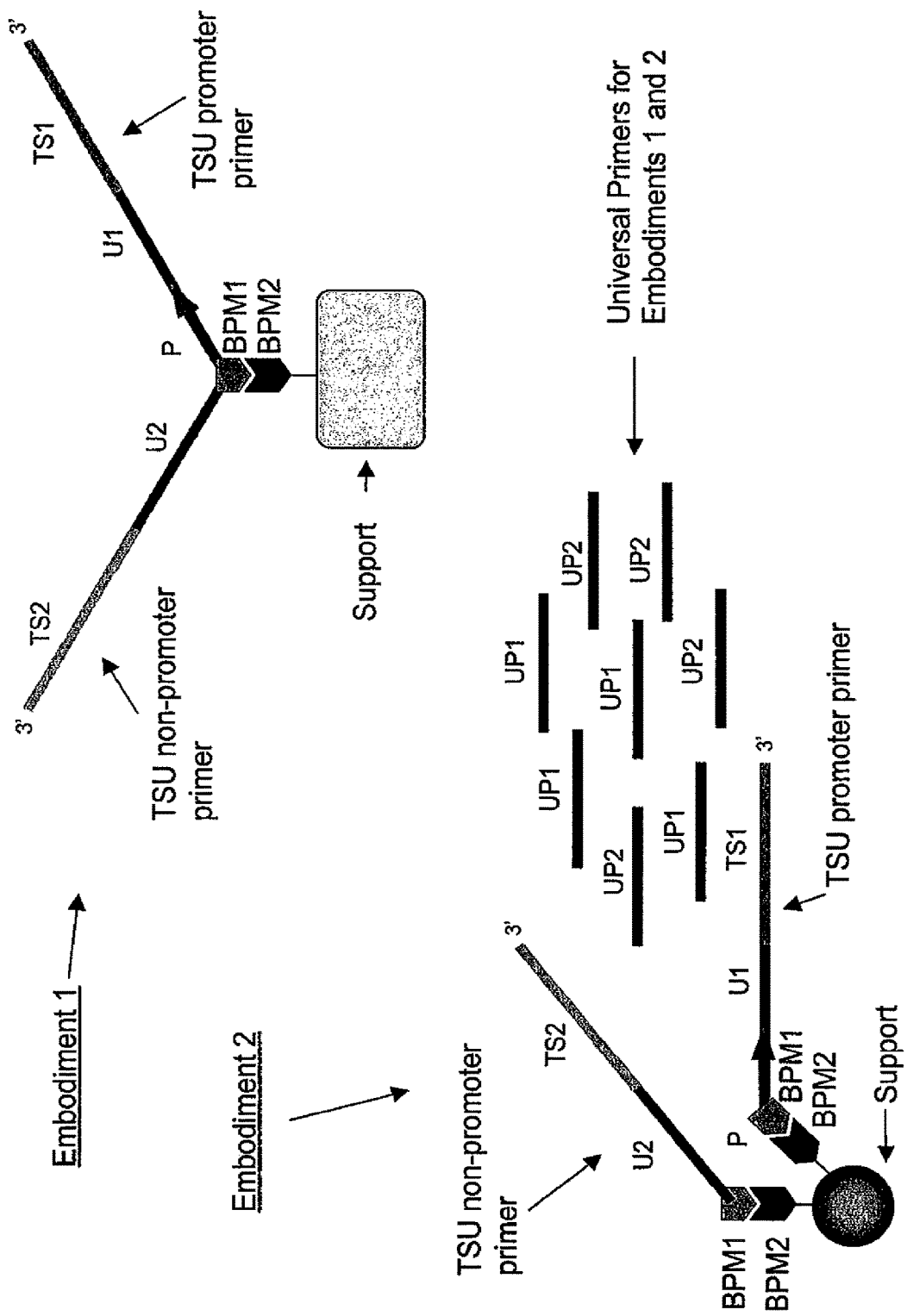
FIG. 11 is a schematic drawing of two embodiments of TSU primers that do not include an S-oligonucleotide but which may be used in the first phase of isothermal amplification which is performed using TSU primers attached to a support, followed by the second phase of isothermal amplification performed in solution phase by using the universal primers (UP1 and UP2). In Embodiment 1, a TSU non-promoter primer and a TSU promoter primer are linked together, covalently or non-covalently, and attached to a support via a first binding pair member (shaded arrow labeled BPM1) which binds specifically to a second binding pair member (dark chevron labeled BPM2) attached to the support (shaded rectangle). In Embodiment 2, the TSU non-promoter primer and TSU promoter primer are separate oligonucleotides which are separately attached to the same support via a BPM1 attached to each oligomer, which binds specifically to a separate binding pair member, BPM2, attached to the support (shaded circle). For both Embodiment 1 and 2, universal primers (UP1 and UP2) are provided in solution phase and are unattached to a support.

Referring to FIG. 11, two preferred embodiments are illustrated that allow assay steps to be performed attached to a support. Both embodiments use a combination of TSU primers (TSU promoter primer and TSU non-promoter primer sequences) that are attached via members of a specific binding pair to a support. The TSU primers in both embodiments provide target specific sequences (TS1 and TS2) and universal sequences (U1 and U2) as described earlier in this disclosure. And both embodiments use universal primers (UP1 and UP2) in the second phase of amplification as described earlier in this disclosure. In contrast to the embodiments that use a TSU primer complex that includes an S-oligonucleotide (e.g., as shown in FIG. 3), the TSU primers of these two embodiments are physically linked by being attached to a support. In FIG. 11, embodiment 1, the TSU promoter primer and TSU non-promoter primer sequences are linked to a support via a first binding pair member (BPM1) that binds specifically with a second binding pair member (BPM2) attached to the support. This may be accomplished by synthesizing a single oligonucleotide that contains all of the structural elements of the TSU promoter primer and TSU non-promoter primer sequences in the appropriate order (e.g., 3'-TS2-U2-5'-5'-P-U1-TS1-3') with a BPM1 element associated with the synthetic oligonucleotide, or by synthesizing two oligonucleotides (TSU promoter primer sequence and TSU non-promoter primer sequence) which are then attached to the same BPM2 moiety via a BPM1 moiety associated with the primers. In FIG. 11, Embodiment 2, the TSU promoter primer oligonucleotide and TSU non-promoter primer oligonucleotide are linked to the same support via a first binding pair member (BPM1) associated with each primer that binds specifically but independently with a second binding pair member (BPM2) attached to the support. In both embodiments, the TSU primers are maintained in close proximity by being bound to the same support. Because the TS1 sequence of the TSU promoter primer binds with a complementary sequence in the target nucleic acid strand (TS1'), the TSU primer may function as a capture probe to selectively bind and separate the intended target nucleic acid from a sample mixture, by using the support to separate the TSU primer-target complex from other sample components. Then, the TSU primer-target complex attached to the support and mixed with amplification reaction components (e.g., substrates, enzymes, cofactors) serves as a primer-template complex in the initial phase of amplification substantially as described earlier in this disclosure except that the support substitutes for the S-oligonucleotide in providing the TSU non-promoter primer in close proximity to the cDNA synthesized from the initial TSU primer-target complex. The RNA transcripts from the first phase of amplification then serve as templates for the second phase of amplification by using the UP1 and UP2 universal primers substantially as described in this disclosure (referring to FIG. 10).

The supports in both embodiments shown in FIG. 11 may be used to localize the amplification and detection steps, temporally or spatially or both for specific analytes of interest. For example, if three different analytes (A1, A2, A3) are present in a sample, the three different target nucleic acids (T-A1, T-A2, T-A3) may be captured in a single target capture step by using three different TSU primers attached to different supports or different locations of one support, each TSU primer specific for its respective analyte by use of different TS1 sequences (TS-A1, TS-A2, TS-A3), each specific for one of the targets. Spatial separation of may result, e.g., when a single support is used to which the TSU primer complexes are attached at different predetermined loci, such as in an array. Other embodiments that achieve spatial separation include different wells or containers of a multi-chambered device which contain TSU primer complexes in a predetermined pattern or a random pattern, such as achieved by dispensing a known amount of solution in which one or more support particles are suspended at a predetermined probability, e.g., a dilution at which an average of one or fewer individual supports are deposited at a locus on or in a well or chamber. Spatial separation may also be achieved by selectively separating each of the supports into separate chambers or sections of a device before performing the amplification step by using a physical characteristic of the support to which each of the different TSU primers is attached. For example, TSU primers having different TS1 sequences (TS-A1, TS-A2, TS-A3) may be attached to different particular supports that are separable based on size, density, ligand binding capabilities, magnetic properties and the like, so that the different supports with their attached TSU primer-target complexes may be spatially separated before performing amplification steps that all use the same reagents, including the same universal primers. The amplified product detected at a particular spatial location in the detecting step indicates whether a particular analyte was present in the sample, and the cumulative detection results of all of the locations may indicate that more than one analyte was present in the sample, and may provide a quantitative or proportional measurement of each analyte present in the sample. For example, if an array of 100 chambers is used in which three different TSU primer-target complexes (i.e., TS-A1, TS-A2, TS-A3 primers) are spatially separated to produce an average of one TSU primer-target complex per locus before performing amplification steps, and the detection step results in 10 chambers positive for the TS-A1 primer, 30 chambers positive for the TS-A2 primer, and 50 chambers positive for the TS-A3 primer, then the results indicate that the sample contained all three analytes A1, A2 and A3, in a ratio for A1:A2:A3 of 1:3:5.

Similarly, temporal separation may be used to amplify products from different target nucleic acids and detect the amplified products. For either embodiment of FIG. 11, using the model system of three different analytes (A1, A2, A3) present in a sample, the three different target nucleic acids (T-A1, T-A2, T-A3) may be captured in a single target capture step by using three different TSU primer complexes attached to supports, each TSU primer complex specific for its respective analyte by use of different TS1 sequences (TS-A1, TS-A2, TS-A3). Amplification in the first and second phases is performed substantially as described previously herein, except that at different times during the amplification a detection measurement is made for each of the amplified products, e.g., at a first time (T1) for the A1 product, at a second time (T2) for the A2 product, and at a third time (T3) for the A3 product, which each product results in a different detectable signal such as fluorescence at a different wavelength. Thus, positive signals detected only at T1 and T3 indicate that the sample contained only analytes A1 and A3, and did not contain A2. In other embodiments, temporal detections may be made at sequential times over an extended time range during the amplification reaction, e.g., at T1, T4 and T7 for A1, at T2, T5 and T8 for A2, and at T3, T6 and T9 for A3, and the cumulative results may indicate both the presence and relative amounts of each of the analytes present in a sample. For example if a positive signal is detected at T1, T4 and T7 it indicates for A1 is present in the sample, and a positive signal is detected at T8 it indicates that A2 is present in the sample, and a positive signal is detected at T6 and T9 it indicates that A3 is present in the sample. Amplification for each of the analytes is expected to proceed at approximately the same rate due to use of the same conditions and universal primers in the second phase of amplification. Thus the relative amount of amplified product and the resulting earliest time of signal detection for each amplified product provides an indication of the proportional amount of each of the analytes present in the sample. Based on the model system results above in which signal for A1 is detected before signal for A3, which is detected before signal for A2, the relative of amounts of each of the analytes in the sample are A1 greater than A3 greater than A2.

A combination of spatial and temporal separations may be used in an assay to amplify and selectively detect amplified products from more than one analyte in a reaction, to allow detection of amplified products for an analyte at discrete locations and times. For example, spatial separation may involve use of an array of TSU primer complexes attached to a support at predetermined loci combined with temporal separation by detecting signals at different time points from each or selected groups of loci to detect amplification products resulting from an amplification reaction performed on the array. In another embodiment, TSU primer complexes attached to particulate supports may be suspended in solution phase of an amplification reaction mixture for some portions of the amplification reaction and then sedimented or attracted to a surface in a random or non-random pattern (spatial separation) for detection of signal from the localized amplification products made during other selected times during the amplification reaction (temporal separation) so that the resulting series of cumulative patterns of detectable signals provide information on both the presence and relative amounts of analyte(s) present in the sample. Those skilled in the art will appreciate that a wide variety of spatial, temporal, and combined spatial and temporal separations may be used to selectively detect amplification products resulting from amplification reactions that include multiple analytes (i.e., multiplex reactions).

Those skilled in the art will also appreciate that other embodiments are encompassed by the general principles of the assays disclosed herein. That is, assays that include a target capture step to separate a target nucleic acid from a sample and attach an initial TSU primer to the selected target nucleic acid, followed by an isothermal amplification reaction that is characterized by two phases, in which the first phase introduces universal sequences into products made from the target nucleic acid, and the second phase uses those universal sequences for further production of amplification products, which are detected in the final stage of the assay. The target capture step includes attachment of an initial TSU primer that contains a first universal sequence attaches to the target nucleic acid. The target capture step is followed by an initial phase of isothermal amplification that uses the initial TSU primer and a second TSU primer, which contains a second universal sequence, to produce RNA transcripts that contain the first universal sequence and the complementary sequence of the second universal sequence, which flank a target specific sequence. This is followed by a second phase of isothermal amplification in which the RNA transcripts made in the first phase are amplified by using a continuous process of making additional RNA transcripts by using universal primers that bind specifically to the universal sequences (or their complements) introduced by using the initial TSU and second TSU primers. The final detection step detects a signal resulting from the amplified products made during the second phase of isothermal amplification to indicate that the target nucleic acid selected in the target capture step was present in the tested sample. These general assay steps may be used with a variety of different primers of different sequences which can be readily designed by those skilled in the art of molecular biology in view of the general structural features of the primers described herein.

Figure 12:
FIG. 12 is a schematic drawing showing structures used in a target capture (TC) step with initial primer attachment (left side, labeled A.) and primers used in the second phase of isothermal amplification (right side, labeled B.), for Embodiment 1 (upper half above the line) and Embodiment 2 (lower half below the line). In Embodiment 1, the TC step (left side, upper half) includes a capture complex made up of the target nucleic acid attached to a support, via a target specific capture probe that hybridizes to the target strand (shown by vertical lines between a short horizontal line and the longer horizontal line representing the target strand) and also hybridizes via a poly-A sequence to an immobilize poly-T sequence attached to the support (shaded circle). The target nucleic acid is attached at another location to a TSU primer complex that includes the TSU promoter primer hybridized specifically to a sequence in the target strand and to an S-oligonucleotide that is hybridized to a TSU non-promoter primer (substantially as shown in FIG. 3). In Embodiment 1, the second phase of amplification (right side, upper half) uses two universal primers: a universal promoter primer (UP1) and a universal non-promoter primer (UP2) that hybridizes to a complementary sequence introduced in the RNA transcript by use of the TSU primer complex. In embodiment 2, the TC step (left side, lower half) includes the capture complex as shown for embodiment 1 and only the TSU promoter primer hybridized via a target-specific sequence at another location on the target strand, and the second phase of amplification (right side, lower half) uses one universal promoter primer (UP1) and one target specific primer (TSP).
Figure 12:
Figure 12:
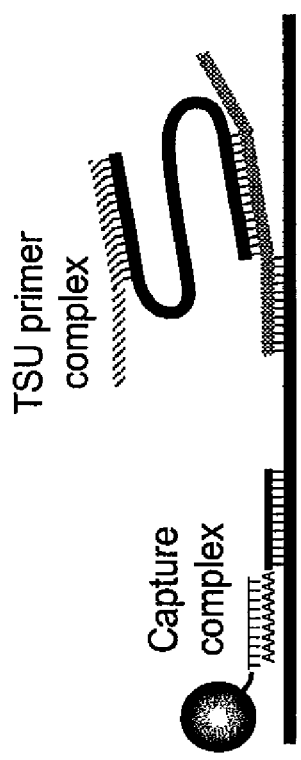
Figure 12:
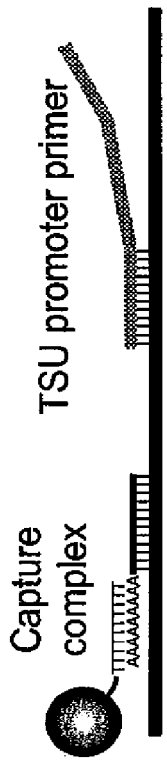
Figure 13:
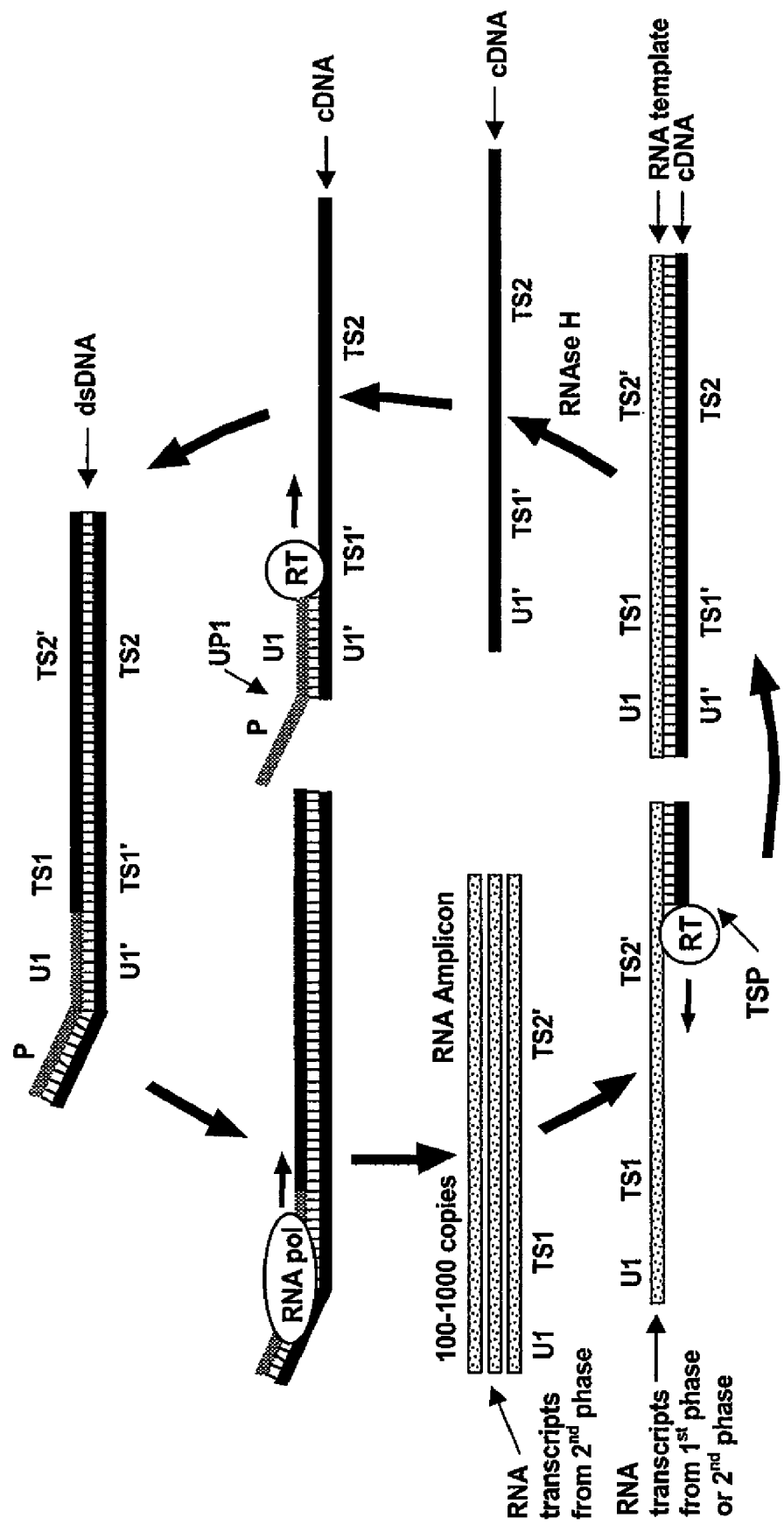
FIG. 13 is a schematic drawing showing the steps in the second phase of isothermal amplification substantially as shown in FIG. 10, except that RNA transcripts from the first and/or second phases (lower left) are hybridized to a target specific primer (TSP) that is extended by RT to synthesize the cDNA strand (lower right) using the RNA transcripts as templates, and no U2 or U2' universal sequences are present.

Other embodiments of isothermal amplification methods that use universal sequences may use fewer TSU primers and universal primers compared to the embodiments described above, while retaining features characteristic of the method such as attachment of a TSU primer to the target nucleic acid during the target capture step and but performing isothermal amplification steps by using a combination of universal and target specific primers. For example, an embodiment may using only one initial TSU promoter primer which hybridizes to the target nucleic acid during the target capture step and is extended synthetically to introduce a single universal sequence into the cDNA and later into the RNA transcripts made during the first phase of isothermal amplification, so that the second phase of amplification uses only a single universal primer combined with one or more target specific primers to make the amplification products that are detected to indicate the presence of the analyte(s) in the tested sample. FIG. 12 illustrates two embodiments (Embodiment 1, upper, and Embodiment 2, lower) to compare difference in the (A.) target capture (TC) step with initial primer attachment and (B.) primers used in the second phase of amplification. Referring to FIG. 12, Embodiment 1 in the TC step attaches to the target strand a TSU primer complex that includes both a TSU promoter primer and a TSU non-promoter primer linked by an S-oligonucleotide as described earlier herein, where the target specific portion of the TSU promoter primer binds to a complementary sequence in the target strand to link a universal sequence (U1) to the cDNA that will be made by extending the 3' end of the TSU promoter primer in the first phase of isothermal amplification, as described earlier herein. In contrast, Embodiment 2 in the TC step attaches to the target strand only a TSU promoter primer which is hybridized to via its target specific portion to a complementary sequence in the target strand to link a U1 sequence to the cDNA that will be made by extending the 3' end of the TSU promoter primer, as described above. In Embodiment 1, the first phase of amplification will continue as described earlier with reference to FIGS. 5 to 8, in which the TSU non-promoter primer with its universal sequence will be used to make the second DNA strand, so that the RNA transcripts made in the first phase of amplification will contain two universal sequences. In Embodiment 2, instead of using a TSU non-promoter primer, a target specific non-promoter primer is hybridized to a complementary sequence in the cDNA and extended synthetically to make the second strand DNA, so that the RNA transcripts made in the first phase of amplification contain only one universal sequence. Referring to FIG. 12, B., in the second phase of isothermal amplification for Embodiment 1 (upper portion), two universal primers, a universal promoter primer (UP1) and universal non-promoter primer (UP2), are used to make RNA amplicons as described earlier with reference to FIG. 10. In contrast, in Embodiment 2, of FIG. 12, B., the second phase of isothermal amplification uses only one universal promoter primer (UP1) combined with a target specific primer (TSP). Referring to FIG. 13, in the second phase of isothermal amplification, RNA amplicons are made by using synthetic steps similar to those described above, but by using the TSP (instead of UP2) to initiate synthesis of the cDNA using the RNA transcripts as templates (starting at lower left in FIG. 13.). That is, in this embodiment, no U2 or U2' universal sequences are present in the reaction.

Figure 14:
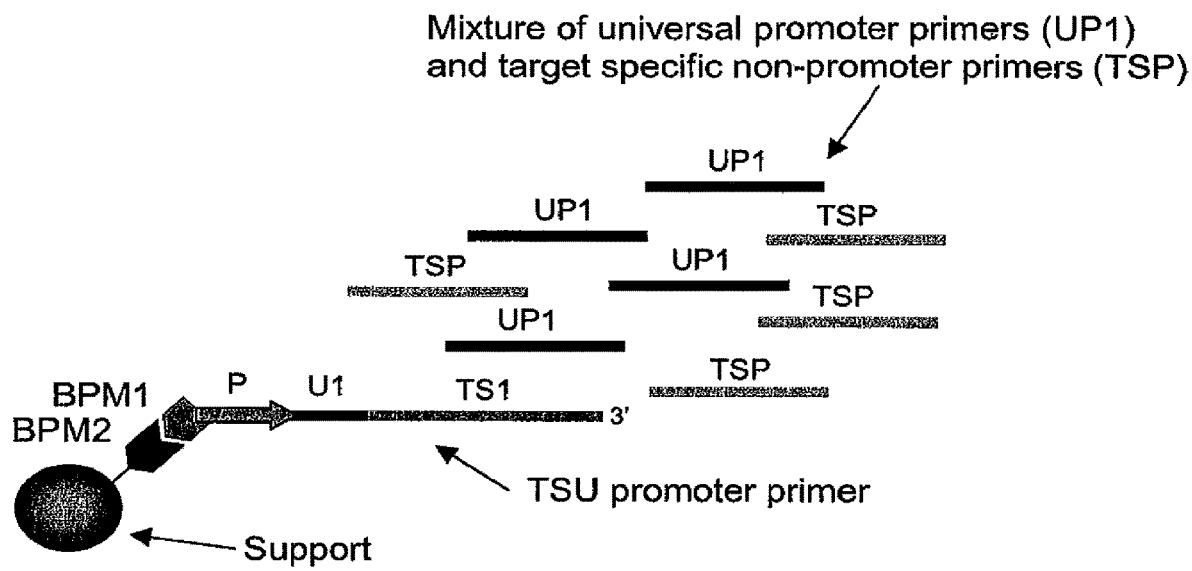
FIG. 14 is a schematic drawing showing an embodiment in which (lower left) a TSU promoter primer used in a first phase of amplification is attached to a support via a first binding pair member (BPM1) that binds specifically to a second binding pair member (BPM2) attached to the support (shaded circle), and a mixture of universal promoter primers (UP1) and target specific primers (TSP) in solution phase are used in the second phase of amplification.

An embodiment that uses a single TSU primer and a target specific primer may be used in assays that make use of the TSU primer attached to a support, similar to those embodiments described above with reference to FIG. 11. FIG. 14 schematically depicts a TSU promoter primer oligonucleotide made up of a promoter sequence (P), a universal sequence (U1) and a target specific sequence (TS1) which is attached to a support via a first binding pair member (BPM1) which binds specifically to a second binding pair member (BPM2) attached to the support. The TSU promoter primer is used in the first phase of amplification substantially as described above with reference to FIG. 12 (Embodiment 2). For the second phase of amplification, a mixture containing a universal promoter primer (UP1) and a target specific primer (TSP) is used, as shown in FIG. 14, using the steps as described above and diagramed in FIG. 13, to amplify the RNA transcripts. In one preferred embodiment, a TSU promoter primer attached to a support (as in FIG. 14) may be used to capture the target nucleic acid strand to which it hybridizes by using its TS1 sequence that is complementary to a sequence (TS1') in the target strand. Alternatively, an embodiment that uses a single TSU primer attached to a support may be used in combination with a TC step that uses a capture complex (as in FIG. 12, A.) that includes a support, an immobilized probe and a target specific capture probe, as described in detail previously. In an embodiment that uses a TSU promoter primer attached to a support as the means for separating the target nucleic acid from other sample components, then the TSU promoter primer serves essentially as the capture probe and as the primer for initiation of cDNA synthesis when the complex that includes the support and the TSU promoter primer hybridized to the target strand is mixed with other amplification reagents. In an embodiment that performs a TC step that uses a capture complex made up of a capture probe hybridized to the target strand and bound to the immobilized probe attached to the support, then the TSU promoter primer hybridized to the target strand and attached to another support acts as the primer for initiation of cDNA synthesis when the complex is mixed with other amplification reagents. In both embodiments, the TSU primer attached to a support may be used to separate amplification products spatially, temporally, or as a combination of spatial and temporal separation as described above with reference to FIG. 11, except that the second phase of isothermal amplification relies on using a TSP instead of a universal primer (UP2).

Embodiments such as those described with reference to FIGS. 12 (embodiment 2), 13 and 14, that use a TSU promoter primer in combination with a target specific primer (TSP) are advantageous in a number of applications. For example, in assays for detection of one or more species or isolates that share a common target sequence (TS1') that is conserved among the different targets, a TSP may be included for each of the different targets by making the TSP sequence specific for each target. For example, a TS1' sequence that occurs in 16S or 23S rRNA sequence of many members of a genus (e.g., *Mycobacterium*) may be used to design a TSU promoter primer that contains a TS1 sequence that will bind to the target 16S or 23S rRNA from all of the intended targets in the genus. Then, for each of the intended target species included in the genus targets (e.g., *M. tuberculosis, M. avium, M. abscessus, M. africanum, M. asiaticum, M. avium, M. bovis, M. celatum, M. chelonae, M. flavescens, M. fortuitum, M. gastri, M. gordonae, M. haemophilum, M. intracellulare, M. interjectum, M. intermedium, M. kansasii, M. malmoense, M. marinum, M. nonchromogenicum, M. paratuberculosis, M. phlei, M. scrofulaceum, M. shimodei, M. simiae, M. smegmatis, M. szulgai, M. terrae, M. triviale, M. tuberculosis, M. ulcerans* or *M. xenopi*) a TSP specific for each member is designed and used in the isothermal amplification reaction to make amplified products specific for each target species, which may be individually detected by using standard probe hybridization or size separation methods. In another example, related viral targets, such different human papillomavirus (HPV) types may be detected in a single reaction mixture designing a TSU promoter primer that binds via its TS1 sequence to a common sequence (TS1') present in all of the desired HPV types to be detected (e.g., HPV types 16, 18, 31, 33, 35, 45, 51, 56, 58, 59 and 68). Thus, the initial cDNA made from the TSU promoter primer will be synthesized for each of the intended target HPV types present in the sample using HPV mRNA in the E6/E7 gene target sequence. Then, for amplification and detection of individual HPV types of interest, a TSP is designed for each target (e.g., one each for HPV16 and HPV18) or for a combination of related targets (e.g. one specific for both HPV 16 and HPV18), i.e., each TSP binds specifically to a sequence of its intended HPV type(s) only. Each TSP specific for its target type is used in the isothermal amplification reaction to make amplified products specific for the selected target types and the amplified products are individually detected by using standard methods (hybridization, size separation, sequencing) to identify the HPV type(s) present in the tested sample. Embodiments such as these are particularly useful for multiplex reactions, in which more than one selected target is present in a sample and is amplified to produce a detectable amplified product that is distinguishable from other amplified products, so that a signal from each amplified product present in the reaction mixture indicates the target analytes that were present in the tested sample.

Another application for which embodiments that use a single universal sequence provided by a TSU primer combined with multiple target specific primers (TSP) are useful is for detecting different forms of related genetic sequences or products. For example, cancers may be correlated with the presence of certain genetic translocations or translocation breakpoints (e.g., chronic myelogenous leukemia (CML) associated with translocations between human chromosomes 9 and 22 in the abl gene of chromosome 9 and the "breakpoint cluster region" or bcr gene of chromosome 22). To detect different types of translocations, an embodiment of the methods described herein uses a TSU primer in which the TS1 sequence is specific for a target sequence in a genetic sequence or mRNA of one of the translocation members (e.g., abl gene) that is common to many different cancer-associated translocations, and therefore can amplify sequences from many different translocations independent of the breakpoint. To amplify and detect specific translocations that are associated with cancers or have particular prognostic value, a variety of different TSPs are designed (e.g., different bcr sequences), each one specific for amplifying a particular sequence associated with a cancer-associated translocation, where the amplified sequence may be detected specifically using standard methods (e.g., probe hybridization, sequencing, or size of amplicon). A sample suspected of containing nucleic acid (DNA or RNA) that has a diagnostic translocation sequence is then amplified using the TSU promoter primer that amplifies many translocations in the target and with the many different TSPs, preferably in a single or a few multiplex reactions, and the amplified products are detected specifically to provide diagnostic or prognostic information based on the particular translocation sequences that are amplified and detected.

Similarly, embodiments that use a single universal sequence provided by a TSU primer and multiple target specific primers (TPS) are useful for detecting different forms of related genetic sequences that occur in different expression products of a gene (e.g., PCA3 gene associated with prostate cancer; see U.S. Pat. No. 7,008,765). Such different expression products may result from different splicing events in RNA transcripts, where some spiced RNAs are diagnostic of a disease or provide prognostic value, such as whether a cancer tissue is benign or malignant. In such embodiments, a TSU promoter primer is designed to contain a TS1 sequence that is specific for a TS1' sequence contained in all or many forms of the differentially spliced RNA, and the multiple TSPs are designed to each amplify only one form of the differentially spliced RNAs. Following amplification using the TSU promoter primer and the TSPs, preferably in a single multiplex reaction mixture, the amplified products are detected in a way that distinguishes them to provide information on the particular form(s) of spliced RNA present in the tested sample.

Other embodiments that use a single universal sequence provided by a TSU primer and multiple target specific primers (TPS) are useful for detecting mutations in genetic sequences that provide diagnostic or prognostic information, such as by detecting the presence of one or more sequences that result in drug resistance. For example, a number of HIV-1 mutations are associated with the viral infection being resistant to treatment with particular drugs (e.g., see U.S. Pat. No. 6,582,920, Yang et al.). To detect one or more drug resistance mutations in a single reaction, the TSU primer is designed to contain a TS1 sequence that is complementary to HIV-1 mRNA that is common to HIV-1 strains and isolates, independent of whether the strain or isolate contains a drug resistance mutation. The multiple TSPs are designed to amplify a particular sequence that contains a mutation associated with drug resistance. In some embodiments the TSPs are specific for the drug resistance mutations themselves, whereas in other embodiments, the TSPs are specific for a sequence that does not contain the drug resistance mutation per se, but which amplifies a product that contains the drug resistance mutation. The TSU promoter primer is used with the multiple TSPs, preferably in a single multiplex reaction, to amplify products that provide information on whether a drug resistance mutation was present in the nucleic acid of the tested sample. For example, for embodiments in which the TSPs are specific for each of the drug resistance mutations to be detected, the presence or absence of the distinguishable amplified products indicates which mutations are present in the tested sample. In other embodiments in which the TSPs are specific for a sequence that does not contain the drug resistance mutation per se, but which amplifies a product that contains the drug resistance mutation(s), then standard methods of detecting the mutation(s) are used, e.g., probe hybridization including on an array, sequencing, or size separation, including mass spectrometry.

Testing of embodiments that use TSU primers, TSU primer complexes and universal primers, in the isothermal amplification methods as described herein has been performed and amplified products have been successfully detected for viral targets and genetic sequences associated with cancer markers, such as prostate specific antigen (PSA; e.g., U.S. Pat. No. 6,551,778) and PCA3 sequences.

Those skilled in the art of molecular biology will appreciate that TSU oligonucleotides as described herein do not require any specific sequences to function, so long as the chosen sequences fulfill the functional requirements of the TSU oligonucleotides. That is, no single sequence is required for any functional portion of a TSU oligonucleotide, e.g., no particular primer is required for a TSU promoter primer or promoter provider, so long as the TSU oligonucleotide contains sequences for all of the functional portions needed for its function for the embodiment for which it is intended as disclosed herein. Similarly, a TSU primer that does not contain a promoter sequence does not require any particular sequence so long as it contains a U sequence and a TS sequence that allows it to function for the embodiment for which it is intended as disclosed herein. Similarly, no particular sequence is required for an S-oligonucleotide, a covalently linked oligonucleotide made up of two TSU oligonucleotide sequences, or for two TSU oligonucleotides that are directly hybridized to each other via complementary sequences, so long as the appropriate sequences for each functional portion are included as described for the embodiments disclosed herein. Universal primers similarly do not require a particular sequence but instead are chosen to contain sequences that perform with the U sequence(s) chosen for the TSU oligonucleotides as described herein. For example, a universal promoter primer or promoter provider oligonucleotide contains a promoter sequence and a U sequence that functions in the methods described herein, where the U sequence of the universal primer and the U sequence of the TSU promoter oligonucleotide are substantially identical. A U sequence in the universal primer may vary from the U sequence of the TSU oligonucleotide, so long at these sequences share enough identity to allow specific hybridization of the universal primer to a universal sequence once incorporated into an initial or subsequent amplification product, forperforming in the methods disclosed herein. Similarly, the universal primer does not rely on any particular sequence but is selected to be substantially identical to the universal sequence of the TSU non-promoter primer with which it is used. Promoter sequences are preferably, but not necessarily, the same in all TSU promoter primers or promoter providers used in an assay for multiple targets because that simplifies other reaction components (i.e., a single RNA polymerase is used), but different promoter sequences that function with the same or different RNA polymerases may be used. Those skilled in the art will appreciate that many different sequences may be incorporated into TSU oligonucleotides, S-oligonucleotides, and universal primers that fall within the scope of the compositions described herein, which those skilled in the art of nucleic acid amplification are capable of selecting based on the descriptions of the structural and functional features of the oligonucleotides as described herein, where functionality may be demonstrated by using routine testing methods.

Embodiments of the compositions and methods described herein may be further understood by the examples that follow. Method steps used in the examples have been described herein and the following information describes typical reagents and conditions used in the methods with more particularity. Those skilled in the art of nucleic acid amplification will appreciate that other reagents and conditions may be used that will not substantially affecting the process or results so long as guidance provided in the description above is followed. For example, although transcription mediated amplification (TMA) methods are described that use a promoter primer or promoter provider oligonucleotide and a non-promoter primer in an initial phase of amplification, other methods of transcription associated nucleic acid amplification in vitro that rely on primer extension could be modified to use the TSU oligonucleotides as described herein to make amplified products by using universal primers, i.e., the methods are not limited to TMA-based embodiments. Those skilled in the art of molecular biology will also understand that the disclosed methods and compositions may be performed manually or in a system that performs one or more steps (e.g., pipetting, mixing, incubation, and the like) in an automated device or used in any type of known device (e.g., test tubes, multi-tube unit devices, multi-well devices such as 96-well microtitre plates, and the like).

Exemplary reagents used in the methods described in the examples include the following. Sample Transport Medium ("STM") contained 15 mM sodium phosphate monobasic, 15 mM sodium phosphate dibasic, 1 mM EDTA, 1 mM EGTA, and 3% (w/v) lithium lauryl sulfate (LLS), at pH 6.7. Specimen Dilution Buffer contained 300 mM HEPES, 3% (w/v) LLS, 44 mM LiCl, 120 mM LiOH, 40 mM EDTA, at pH 7.4. Target Capture Reagent (TCR) contained 250 mM HEPES, 310 mM lithium hydroxide, 1.88 M lithium chloride, 100 mM EDTA, at pH 6.4, and 250.micro.g/ml of magnetic particles (1 micron SERA-MAG.sup.™ MG-CM particles, Seradyn, Inc. Indianapolis, Ind.) with $(dT)_{14}$ oligomers covalently bound thereto. TC Wash Solution contained 10 mM HEPES, 150 mM sodium chloride, 6.5 mM sodium hydroxide, 1 mM EDTA, 0.3% (v/v) ethanol, 0.02% (w/v) methyl paraben, 0.01% (w/v) propyl paraben, and 0.1% (w/v) sodium lauryl sulfate, at pH 7.5. Probe Reagent contained one or more labeled detection probes in a solution made up of either (1) 100 mM lithium succinate, 3% (w/v) LLS, 10 mM mercaptoethanesulfonate, and 3% (w/v) polyvinylpyrrolidon, or (2) 100 mM lithium succinate, 0.1% (w/v) LLS, and 10 mM mercaptoethanesulfonate. Hybridization Reagent was either (1) 190 mM succinic acid, 17% (w/v) LLS, 100 mM lithium hydroxide, 3 mM EDTA, and 3 mM EGTA, at pH 5.1, or (2) 100 mM succinic acid, 2% (w/v) LLS, 100 mM lithium hydroxide, 15 mM aldrithiol-2, 1.2 M lithium chloride, 20 mM EDTA, and 3.0% (v/v) ethanol, at pH 4.7. Selection Reagent used to treat mixtures that use AE-labeled detection probes contained 600 mM boric acid, 182.5 mM sodium hydroxide, 1% (v/v) octoxynol (TRITON.sup.® X-100), at pH 8.5, and Detection Reagents used to elicit a chemiluminsecent signal from AE-labeled probes included (1) Detect Reagent I made of 1 mM nitric acid and 32 mM hydrogen peroxide, and (2) Detect Reagent II (to neutralize pH) which was 1.5 M NaOH. An exemplary Amplification reagent or pre-amplification reagent, as used herein, can include a mixture at about pH=7.5 to 8.0 and containing about 25 to 27 mM Tris; about 17 to 23 mM $MgCl_2$; about 23 to 30 mM KCl; about 3 to 7.5% v/v glycerol; about 0.04 to 0.05 mM Zn Acetate; about 0.5 to 0.7 mM of each of dATP, dCTP, dGTP, dTTP; about 3.9 to 5.4 mM of each of rATP, rCTP, rGTP, rUTP; and about 0.015 to 0.02% v/v ProClin 300 preservative (Sigma Aldrich, St. Louis, Mo.). Primers and/or probes may be added to the reaction mixture in the amplification reagent or are separate from the reagent (primerless amplification reagent or primerless pre-amplification reagent). Exemplary Enzyme reagents, as used in amplification or pre-amplification reaction mixtures, can include a mixture at about pH=7.0 and containing about 56 to 224 U/$\mu$l of MMLV reverse transcriptase (RT); about 35 to 40 U/$\mu$l of T7 RNA polymerase per reaction (where 1 U of RT incorporates 1 nmol of dTTP in 10 min at 37° C. using 200-400 micromolar oligo dT-primed polyA template, and 1 U of T7 RNA polymerase incorporates 1 nmol of ATP into RNA in 1 hr at 37° C. using a T7 promoter in a DNA template); about 4 to 16 mM HEPES; about 17 to 70 mM N-Acetyl-L-Cysteine; about 0.75 to 3.0 mM EDTA; about 0.01 to 0.05% w/v Sodium Azide; about 20 to 25 mM Trizma; about 30 to 50 mM KCl; about 7.5 to 20% v/v glycerol anhydrous; about 2.5 to 10% v/v Triton-X 102 and 0 to about 150 mM trehalose.

An exemplary protocol for TMA reactions that detect results by using labeled probes at the end of the amplification reaction follows. The TMA reaction uses substantially the procedures described previously in detail (U.S. Pat. Nos. 5,399,491 and 5,554,516). Briefly, a reaction mixture (e.g., 0.08 ml) containing amplification reagent, target nucleic acid, and amplification oligomers (e.g., 15 pmol of each oligomer per reaction) was mixed, covered with silicon oil (0.2 ml) to prevent evaporation, and incubated for 10 min at 62° C. and then for 5 min at 42° C., and then the enzyme reagent (0.025 ml containing reverse transcriptase and T7 RNA polymerase) was added, and reaction mixtures were incubated for 60 min at 42° C. Following amplification, detection of the amplified products involved mixing the amplification mixture with an acridinium ester (AE) labeled detection probe oligomer specific for the amplification product (e.g., 0.1 pmol per reaction in 0.1 ml of probe reagent, or an amount previously determined to produce a maximum detectable signal in an acceptable range, such as up to 2,000,000 relative light units ("RLU") from hybridized labeled probe). Mixtures of probe and amplified sequences were incubated to bind the probe to the amplified product and then treated to produce chemiluminescent signal from hybridized probes substantially as described (U.S. Pat. Nos. 5,283,174 and 5,639,604). Briefly, the probe and amplified product mixtures were incubated for 20 min at 62° C., then cooled at room temperature about 5 min and selection reagent (0.25 ml) was added, mixed, incubated 10 min at 62° C. and then at room temperature for 15 min to hydrolyze the AE label on unbound probes. Chemiluminescence from AE on bound probes was produced by adding detect reagent I, incubating, adding detect reagent II, and measuring chemiluminescence in a luminometer (e.g., LEADER.sup.®, Gen-Probe Inc., San Diego, Calif.).

An exemplary protocol for TMA reactions that detect results in real time follows. The assay includes purification of target nucleic acids before amplification, amplification, and detection of the amplified products during amplification. Target capture is performed substantially as previously described in detail (U.S. Pat. Nos. 6,110,678, 6,280,952, and 6,534,273). Briefly, samples were prepared to contain known amounts of target RNA (in vitro transcripts ("IVT") present at a predetermined copy level per sample in a total volume of 0.2 ml of a 1:1 (v:v) mixture of water and sample transport medium). Each sample was mixed with 0.05 ml of TCR that typically contained 5 to 15 pmol of target capture oligomer (TCO) specific for the analyte nucleic acid to be captured (i.e., 3' target-specific binding region) and a 5' tail region (e.g., dT.sub.3A.sub.30 sequence) for binding to the immobilized probe (e.g., poly-T oligomers attached to paramagnetic particles; 12.5.micro.g of particles with attached oligomers per reaction), 5 to 15 pmol of TSU primer and/or complex that includes TSU primer and TSU promoter primer or provider sequence for each analyte (for initial phase of amplification), and optionally 2 to 5 pmol of blocker oligomer (for rTMA amplification reactions). The mixtures were incubated for 25 to 30 min at 60±1° C. and then for 25 to 30 min at room temperature (20 to 25° C.) to form hybridization complexes through which target nucleic acids were bound to the paramagnetic particles which were the isolated by using magnetic separation (e.g., KingFisher96.sup.™ magnetic particle processor, Thermo Fisher Scientific, Inc., Waltham, Mass.) and washed one time using TC wash solution. Particles were resuspended in 0.06 to 0.1 ml of amplification reagent and with amplification oligonucleotides used in the second phase of amplification (e.g., TS primer, universal primer(s), 3' blocked universal promoter provider). Detection probes (e.g., molecular beacon or molecular torch probes labeled with a fluorescent label compound) may be added with amplification oligonucleotides, or with addition of enzymes, or following addition of enzymes. Reaction mixtures were covered to prevent evaporation and incubated for 1 to 2 minutes at 42±0.5° C. While keeping them at 42±0.5° C., the mixtures were uncovered and mixed with 0.02 ml of enzyme reagent per mixture, covered again, and incubated for 30 to 90 minutes at 42±0.5° C., during which time fluorescence is measured at regular time intervals (e.g., every minute) which are referred to as "cycles" for data collection and display, which is typically a graph of detected fluorescence units versus time (cycles), from which a time of emergence of signal was determined (i.e., time at which fluorescence signal for a sample becomes positive over a background level, which is usually predetermined for the assay).

Example 1: Universal TMA (uTMA) System for Detection of Multiple HPV Types

This example shows the performance of an embodiment of universal isothermal amplification referred to as "half uTMA", in a system to detect at least 12 human papillomavirus (HPV) types associated with a high risk of developing cervical cancer (high-risk HPV types). The target was either 200 or 1,000 copies/reaction (c/rxn) of a single in vitro transcript of the specified HPV type. Target capture, amplification and probe detection by using hybridization protection assay (HPA) which were all performed substantially as described earlier (U.S. Pat. Nos. 6,110,678 and 6,534,273 for target capture, U.S. Pat. Nos. 5,399,491 and 5,554,516 for TMA, and U.S. Pat. Nos. 5,283,174 and 5,639,604 for HPV). The target capture mixture contained in the TC reagent 2 pmol each of target capture oligonucleotides of SEQ ID Nos. 28-32. The target capture mixture additionally contained 5 pmol each of HPV TSU T7 promoter primers of SEQ ID Nos. 1-9. Each of these primers contained the target-specific region, the sequence of the universal T7 primer, and a T7 promoter region. Amplification buffer contained reagents for performing TMA plus 15 pmol each of universal T7 primer of SEQ ID NO:33 and the TS (target-specific) non-T7 primers of SEQ ID Nos. 10-13.

During the target capture step, which includes hybridization at 62° C., the capture oligonucleotides and TSU T7 promoter primers hybridized to their specific in vitro transcripts; and all unhybridized primers were removed during the wash steps. After target capture, the magnetic beads with bound complex that includes the target strand and hybridized TSU primer were mixed with amplification reagent containing primers, RNA polymerase, reverse-transcriptase, dNTPs and NTPs, and then incubated at 42° C. for 60 minutes. In the first step of the reaction (initial amplification phase), a cDNA transcription template is created which incorporates the universal T7 primer region and a HPV target-specific binding region. Amplification proceeds (in the second phase of amplification) by using the universal T7 promoter primer and a non-T7 primer specific for the target in the reaction. RNA amplicons were detected by HPA by using a mixture of target-specific acridinium ester (AE)-labeled probes of SEQ ID Nos. 20-27. All probes not hybridized to an amplicon target were hydrolyzed by using the selection reagent during the HPA procedure and rendered non-chemiluminescent. Probes that were bound to amplicon target and remained protected from hydrolysis. HPA detection was performed by using the detection reagents, and the resulting chemiluminescent signals were measured and expressed in relative light units (RLU).

Table 1 shows RLU signals (average of 3 replicates) obtained for 12 high-risk HPV types, 4 low-risk HPV types, and negative reactions in which no target was added. A positive reaction was scored for RLU greater than 20,000. In this example, all high-risk HPV types were detected successfully at 200 c/rxn, except HPV 45, which was positive at 1,000 c/rxn. None of the low-risk HPV types tested gave a positive signal.

TABLE 1

| Group | Target | Avg RLU 200 c/rxn | Avg RLU 1,000 c/rxn |
|---|---|---|---|
| A1 | HPV 16 | 3,125,124 | 3,335,360 |
|  | HPV 31 | 345,676 | 1,524,821 |
|  | HPV 35 | 2,948,726 | 3,207,962 |
| A2 | HPV 33 | 2,571,697 | 3,924,319 |
|  | HPV 58 | 922,123 | 4,270,230 |
| C1 | HPV 18 | 997,356 | 1,438,953 |
|  | HPV 45 | 12,839 | 579,850 |
|  | HPV 59 | 1,950,796 | 2,521,835 |
| C2 | HPV 39 | 2,466,025 | 2,452,492 |
|  | HPV 68 | 689,548 | 1,845,594 |
| D | HPV 51 | 1,571,834 | 1,604,492 |
|  | HPV 56 | 1,015,787 | 775,501 |
|  |  | Avg 1 mil c/rxn | Avg 10 mil c/rxn |
| Low-risk types | HPV 6 | 9,431 | 9,790 |
|  | HPV 11 | 9,839 | 9,644 |
|  | HPV 42 | 9,805 | 9,628 |
|  | HPV 43 | 9,683 | 9,714 |
|  | Negative | 7,612 |  |

Example 2: Sensitivity of Universal TMA System for Detection of High-Risk HPV Types This example shows the performance of an embodiment of universal isothermal amplification referred to as a "full uTMA" in a system that includes two universal sequences to detect 12 high-risk HPV virus types. The target was either 200 or 2,000 copies/reaction of a single in vitro transcript of the specified HPV type. Target capture, amplification and HPA detection steps were all performed substantially as described in Example 1 except that different TSU primer combinations were used. The target capture mixture contained 2 pmol each of TC oligonucleotides of SEQ ID NOs. 28, 29, 30, 31 and 32. The target capture mixture additionally contained S-oligonucleotide TSU primer complexes designed to detect the 12 high-risk HPV types. The TSU primer complexes were formed by hybridizing 5 pmol of TSU T7 promoter primer with 10 pmol of S-oligonucleotide of SEQ ID NO:35 and 15 pmol of the corresponding TSU non-T7 primer. The S-oligonucleotide primer complexes consisted of the S-oligonucleotide of SEQ ID NO:35 in hybridization complexes with the following combinations of TSU T7 promoter primer plus TSU non-T7 primer: SEQ ID Nos. 1 plus 14, SEQ ID Nos. 2 plus 14, SEQ ID Nos. 3 plus 14 (the same TSU non-T7 primer was used for 3 TSU T7 primers directed to a related group of HPV types), SEQ ID Nos. 4 plus 15, SEQ ID Nos. 5 plus 16, SEQ ID Nos. 6 plus 17, SEQ ID Nos. 7 plus 18, SEQ ID Nos. 8 plus 15, and SEQ ID Nos. 9 plus 15 (the same TSU non-T7 primer was used for both TSU T7 primers directed to a related group of HPV types). Each TSU T7 promoter primer contained the target-specific region, the sequence of the universal T7 primer, and a T7 promoter region. Each TSU non-T7 primer contained the target-specific region and the sequence of the universal non-T7 primer. After each S-oligonucleotide primer complex was formed separately, they were combined in the target capture mix. Amplification buffer contained 15 pmol of universal T7 promoter primer of SEQ ID NO:33 and universal non-T7 primer of SEQ ID NO:34.

During target capture hybridization at 62° C., the capture oligonucleotides and TSU T7 promoter primers of the S-oligonucleotide primer complexes hybridized to their specific in vitro transcripts; and all unhybridized primers and S-oligonucleotide primer complexes were removed during the wash steps. After target capture, the magnetic beads with bound target/primer complexes were mixed with amplification reagent containing universal primers, RNA polymerase, reverse-transcriptase, dNTPs and NTPs, and then incubated at 42° C. for 60 minutes. In the first step of the amplification reaction a cDNA transcription template was created which incorporates the universal T7 primer region and a universal non-T7 primer binding region and then amplification proceeded by using the universal T7 and non-T7 primers. RNA amplicons were detected by HPA as described above using a mixture of target-specific AE-labeled probes of SEQ ID Nos. 20 to 27. All probes not hybridized to an amplicon target were hydrolyzed during the HPA procedure and rendered non-chemiluminescent. Probes that were bound to amplicon target and remained protected. HPA detection was performed as described above, and the resulting chemiluminescent signal was measured and expressed in relative light units (RLU).

Table 2 shows signals (average of 3 replicates) obtained for 12 high-risk HPV types, and negative reactions with no target added. A positive reaction was scored for RLU greater than 20,000. In this example, all high-risk HPV types were detected successfully at 200 c/rxn, except HPV 31, which was positive at 2,000 copies per reaction. In other experiments (data not shown), low-risk HPV types were not detected.

TABLE 2

| Group | Target | Avg RLU 200 c/rxn | Avg RLU 2,000 c/rxn |
|---|---|---|---|
| A1 | HPV 16 | 32,620 | 209,397 |
|  | HPV 31 | 17,123 | 84,653 |
|  | HPV 35 | 28,542 | 217,063 |
| A2 | HPV 33 | 22,276 | 797,309 |
|  | HPV 58 | 236,932 | 1,383,602 |

TABLE 2-continued

| Group | Target | Avg RLU 200 c/rxn | Avg RLU 2,000 c/rxn |
|---|---|---|---|
| C1 | HPV 18 | 103,672 | 964,766 |
|  | HPV 45 | 324,981 | 1,329,859 |
|  | HPV 59 | 29,254 | 202,631 |
| C2 | HPV 39 | 100,941 | 1,376,088 |
|  | HPV 68 | 162,030 | 943,088 |
| D | HPV 51 | 241,543 | 1,132,808 |
|  | HPV 56 | 447,408 | 483,658 |
|  | Negative | 10,312 |  |

Example 3 Detection of HPV RNA from Clinical Samples Using a uTMA System

This example shows that the "full uTMA" system as described in example 2 is capable of detecting HPV RNA from cervical swab or scraping samples preserved in alcohol-based liquid media (CYTYC™). The procedure was performed as described in Example 2, except that 100.micro.l of the liquid media sample was added to 500 µl of target capture mixture in the target capture reaction.

The presence of both high- and low-risk HPV was determined by HPV DNA PCR and visualized as bands following separation by agarose gel electrophoresis. Identity of any HPV viral RNA present in the samples was confirmed by DNA sequencing. Samples that produced greater than 20,000 RLU using the full uTMA system, were scored as positive. Table 3 shows the correlation between HPV type and full uTMA amplification results. Positive PCR that resulted in highly visible bands were scored as "+", weak bands as "+/−", and negative results (no visible band) as "−" (and "nd" means not determined). The full uTMA HPV system used in this example was not optimized for sensitivity or specificity, but correctly scored 29 of 34 cervical samples in this study. Samples 6 and 26 were probably not detected because of low amounts of HPV RNA.

TABLE 3

| Sample # | PCR Result | HPV type by sequencing | Targeted high-risk HPV | uTMA result |
|---|---|---|---|---|
| 1 | + | HPV 59 | yes | + |
| 2 | + | HPV 16 | yes | + |
| 3 | +/− | HPV 66 | no | − |
| 4 | + | HPV 61 | no | − |
| 5 | + | HPV 18 | yes | + |
| 6 | +/− | HPV 18 | yes | − |
| 7 | + | HPV 16 | yes | + |
| 8 | + | mixed | yes | + |
| 9 | + | 70 | no | − |
| 10 | + | HPV 81 | no | − |
| 11 | + | mixed | yes | + |
| 12 | + | HPV 16 | yes | + |
| 13 | + | HPV 33 | yes | + |
| 14 | + | HPV 58 | yes | + |
| 15 | + | HPV 31 | yes | + |
| 16 | + | HPV 18 | yes | + |
| 17 | − | nd | nd | − |
| 18 | − | nd | no | − |
| 19 | + | HPV 54 | no | − |
| 20 | − | nd | no | − |
| 21 | − | nd | no | − |
| 22 | − | nd | no | − |
| 23 | + | HPV 59 | yes | + |
| 24 | + | HPV 16 | yes | + |
| 25 | + | HPV 81 | no | − |
| 26 | +/− | HPV 68 | yes | − |
| 27 | + | HPV 68 | yes | + |
| 28 | +/− | HPV 53 | no | − |
| 29 | + | HPV 16 | yes | + |
| 30 | + | HPV 62 | no | ++++ |
| 31 | + | HPV 58 | yes | + |
| 32 | + | HPV 16 | yes | + |
| 33 | + | HPV 58 | yes | + |
| 34 | + | HPV 16 | yes | − |

Example 4: Detection of PCA3 RNA in Uniplex and Multiplex Modes Using Reverse Standard TMA In this example, reverse TMA was performed in a standard, i.e., non-universal, format (RS-TMA). The assay was performed in either the uniplex mode, where the only oligonucleotides required for target capture, amplification and detection of PCA3 were included, or the multiplex mode, where oligonucleotides required for target capture, amplification and detection of both PCA3 and PSA were included. The assay was performed substantially equivalently to the general protocol described above. Specifically, PCA3 in vitro transcript (IVT; SEQ ID NO:62) was spiked into water/STM (1:1) at $10^6$, $10^4$ or $10^2$ copies per reaction. For samples run in the uniplex mode, 5 pmol PCA3 TC probe (SEQ ID NO:53), 2 pmol PCA3 blocker (SEQ ID NO:51), and 5 pmol of PCA3 Non-T7 (NT7) primer (SEQ ID NO:49) were spiked into TCR, and 15 pmol of PCA3 Non-T7 (NT7) primer (SEQ ID NO:49), 10 pmol of PCA3 T7 promoter provider (SEQ ID NO:50) and 12 pmol PCA3 molecular torch (SEQ ID NO:52) were spiked into amplification reagent (amounts given here and later in this and other examples are per reaction, unless indicated otherwise). For samples run in the multiplex mode, in addition to the PCA3 oligomers listed above, 5 pmol PSA TC probe (SEQ ID NO:60), 2 pmol PSA blocker (SEQ ID NO:58) and 5 pmol of PSA NT7 primer (SEQ ID NO:56) were also spiked into TCR, and 15 pmol of PSA NT7 primer (SEQ ID NO:56), 10 pmol of PSA T7 promoter provider (SEQ ID NO:57) and 12 pmol PSA molecular torch (SEQ ID NO:59) were spiked into amplification reagent. For each sample, either 3 or 4 replicates were performed.

After the assay was completed, plots of fluorescence versus time were prepared for each condition (FIG. 19) and average emergence times were determined (Table 4).

TABLE 4

|  | Emergence time (min) | |
|---|---|---|
| PCA3 amount | Uniplex | Multiplex |
| $10^6$ | 8.5 | 12.5 |
| $10^4$ | 11.5 | >80 |
| $10^2$ | 14.5 | >80 |

These results demonstrate that the RS-TMA readily detected PCA3 RNA in a uniplex mode. However, in a multiplex mode (PSA specific oligonucleotides present in addition to the PCA3 specific oligonucleotides present in the uniplex mode), detection of PCA3 was severely hampered. In fact, $10^2$ and $10^2$ copies of PCA3 were undetectable under the conditions of the assay. This illustrates the problem that exists with multiplex amplification reactions known in the art.

These results further demonstrate the ability of RS-TMA to quantitate target level, as amount of PCA3 was directly related to the emergence time. One drawback of the RS-TMA method is the small difference in emergence times between relatively large copy level differences of PCA3 (i.e., 3 minutes difference in emergence time between 100-fold differences in PCA3 copy level). This diminishes the ability of the RS-TMA method to accurately discriminate between small differences (e.g., 3-fold) in copy levels.

Figure 15:
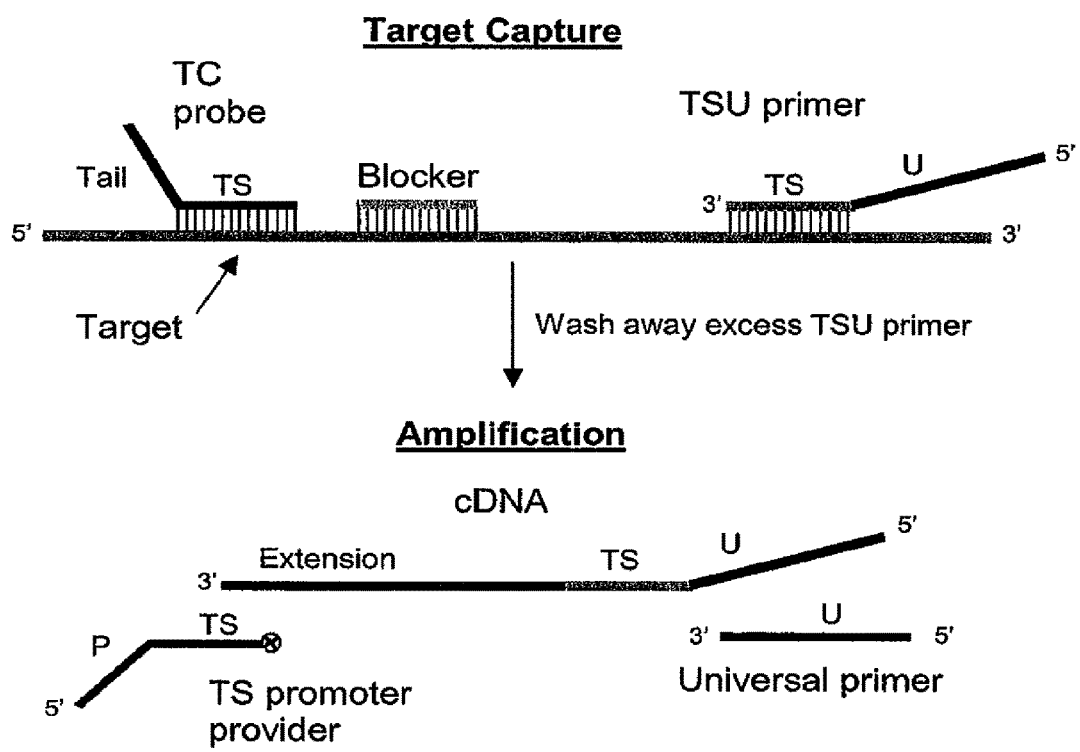
FIG. 15 is a schematic drawing showing components in an embodiment in which the top portion of the diagram shows a hybridization complex made in the Target Capture step, made up of the Target nucleic acid strand hybridized to a target capture (TC) probe that has an unbound poly-A tail and a TS sequence hybridized to a 5' portion of the target strand, a Blocker oligonucleotide hybridized to the target strand downstream from the position hybridized to the TC probe, and a TSU primer hybridized to a 3' portion of the target strand via a TS sequence with an unhybridized universal (U) sequence; and the lower portion of the diagram shows that the nucleic acids present in single-primer isothermal amplification which include (1) the target amplicon consisting of a 5' U sequence, an internal TS sequence, and a 3' sequence copied from the target strand by extension of the TSU primer, (2) a TS promoter provider that includes a 5' promoter (P) sequence, a 3' TS sequence, and a blocked 3' end (⊗), and (3) a universal primer consisting of a universal sequence (U') complementary to the universal sequence of the target amplicon.

Example 5: Detection of PCA3 RNA in Uniplex and Multiplex Modes Using Reverse Universal (Half) TMA In this example, reverse TMA was performed in a universal (half) TMA format (RUh-TMA). In this format, a target-specific universal NT7 primer (TSU NT7) containing a specific target binding region and a universal region at the 5' end of the oligonucleotide is bound to target in the target capture step. Excess TSU-NT7 is washed away. A TSU-NT7 is included in the target capture step for each analyte to be detected in a multiplex assay. In the amplification reaction, a universal NT7 primer (same sequence as the universal sequence of all the TSU-NT7 primers) is added and is used as the NT7 primer in the amplification of all the analytes to be detected in a multiplex reaction. Also in the amplification reaction, a target specific T7 promoter provider (TS-T7) is added for each target to be detected in a multiplex assay. A schematic representation of this format is given in FIG. 15.

The assay was performed substantially equivalently to the protocol described in Example 4 above, with the exceptions described below. Specifically, a PCA3 TSU-NT7 primer (5 pmol; SEQ ID NO:48) and PSA TSU-NT7 primer (5 pmol: SEQ ID NO:55) were spiked into TCR instead of the PCA3 and PSA TS-NT7 primers, respectively, cited in Example 4. Further, a universal NT7 primer (15 pmol; SEQ ID NO:64) was spiked into the amplification reaction instead of the PCA3 TS-NT7 primer in the uniplex mode and instead of both the PCA3 and PSA TS-NT7 primers in the multiplex mode. All other conditions were the same as those given in Example 5. After the assay was completed, average emergence times were determined (Table 5).

TABLE 5

|  | Emergence time (min) | | | |
| --- | --- | --- | --- | --- |
|  | Uniplex | | Multiplex | |
| PCA3 amount | RS-TMA | RUh-TMA | RS-TMA | RUh-TMA |
| $10^6$ | 7.0 | 8.0 | 11.5 | 9.5 |
| $10^4$ | 10.0 | 12.0 | >80 | 11.5 |
| $10^2$ | 14.0 | 17.5 | >80 | 24.0 |

These results demonstrate that the RUh-TMA format readily detected PCA3 RNA. In the uniplex mode, emergence times are somewhat later than the corresponding emergence times obtained with the RS-TMA format. This is favorable in relation to quantitation, and helps to solve the problem with RS-TMA cited in Example 4 (i.e., diminished ability of the RS-TMA method to accurately discriminate between small differences (e.g., 3-fold) in copy levels). In the multiplex mode, the interferences observed in the RS-TMA system are largely overcome, resulting in ready detection of all levels of PCA3 RNA tested.

Example 6: Detection of PCA3 RNA in Uniplex and Multiplex Modes Using Reverse Universal (Full) TMA (RUf-TMA) in the S-Oligo Format In this example, reverse TMA was performed in a universal (full) TMA format (RUh-TMA). In universal (full) TMA, amplification is initiated with a TSU-NT7 and a TSU-T7 provider, and a universal NT7 primer and a universal T7 provider drive subsequent rounds of amplification. In order to provide each target with the primer and provider required for initiation, yet include only a universal primer and provider in the amplification reaction, a TSU NT7 primer and a TSU T7 provider are joined together, this complex is bound to target in the target capture step (via hybridization of the target specific region of the TSU-NT7 to the target) and excess complex is washed away. In amplification, the TSU-NT7 primer is extended, and after digestion of the target via RNAse H, the target specific region of the TSU-T7 provider that is joined to the TSU-NT7 primer binds to the cDNA and amplification is initiated. Amplification then continues using the universal NT7 primer and T7 provider that are in the amplification reagent.

Figure 16:
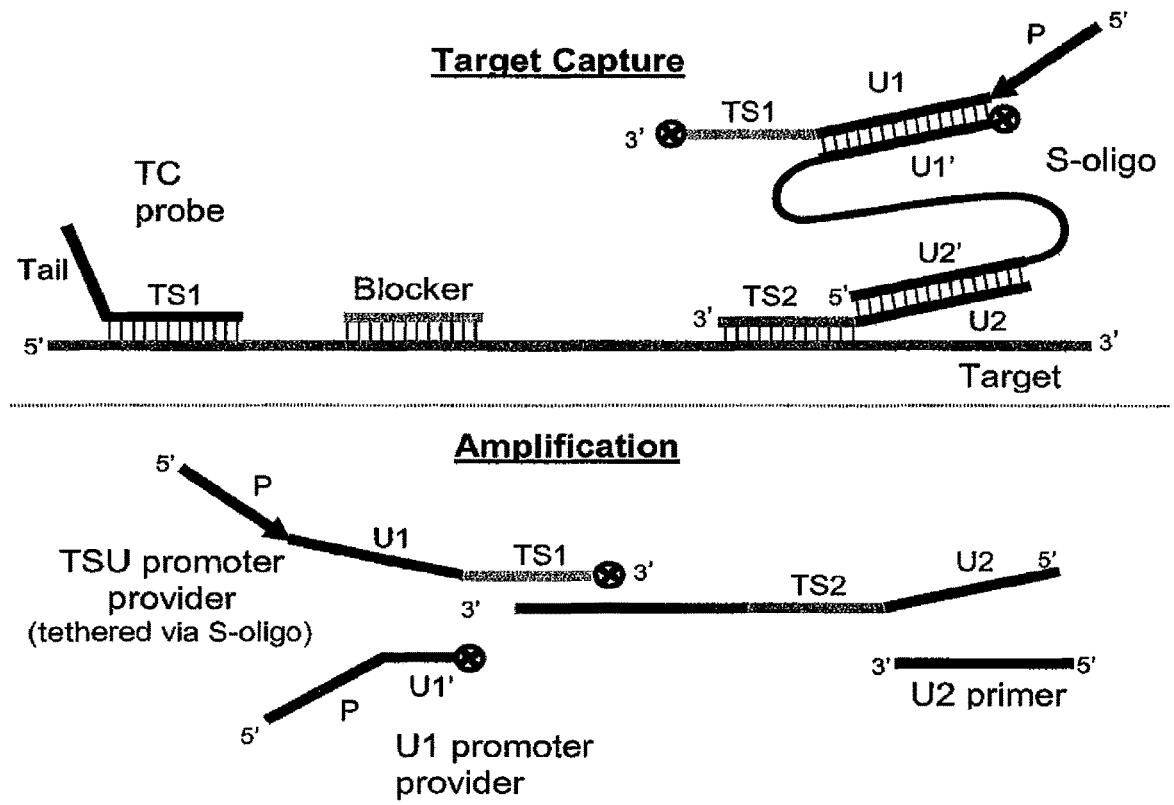
FIG. 16 is a schematic drawing showing components in an embodiment in which the top portion of the diagram shows a hybridization complex made in the Target Capture step, made up of the Target nucleic acid strand hybridized to a target capture (TC) probe that has an unbound poly-A tail and a TS sequence hybridized to a 5' portion of the target strand, a Blocker oligonucleotide hybridized to the target strand downstream from the position hybridized to the TC probe, and a TSU primer complex made up of (top strand) a TSU promoter provider with a 3' blocked end (⊗), an S-oligomer (middle strand, substantially as in FIG. 3), and a TSU primer (lower strand) hybridized to a 3' portion of the target strand via a TS sequence with its universal (U2) sequence hybridized to a complementary (U2') sequence in the S-oligomer; and the lower portion of the diagram shows that nucleic acids present in single-primer isothermal amplification which include (1) the TSU promoter provider hybridized via its TS1 sequence to the extension product made by extension of the TS2 sequence of the TSU primer which includes its U2 universal sequence, (2) a promoter provider oligonucleotide that includes a 5' promoter (P) sequence, a 3' U1' universal sequence, and a blocked 3' end (⊗), and (3) a universal primer consisting of a universal sequence (U2') complementary to the U2 universal sequence.

In the S-oligo mode of RUf-TMA described in this example, the TSU-NT7 primer and TSU-T7 provider are joined via hybridization of both to an intervening "S-oligo" as shown schematically in FIG. 16. This S-oligo complex is pre-formed for each analyte to be included in a multiplex assay, then all are added to TCR in the manner that NT7 primers are added in the RS- and RUh-TMA formats described above.

The assay in this example was performed substantially equivalently to the protocol described in Example 4 above, with the exceptions described below. Specifically, the multiplex portion of the assay contained the oligonucleotides required for target capture, universal amplification and real time detection of not only PCA3 and PSA, but also AMACR. PCA3 S-oligo complex was prepared by mixing 5 pmol of PCA3 TSU-NT7 primer (SEQ ID NO:48), 7.5 pmol S-oligo (SEQ ID NO:66) and 10 pmol PCA3 TSU-T7 provider (SEQ ID NO:50; in this case, the TS- and STM/TCR providers are one and the same in water/STM/TCR (1/1/0.5). Further, PSA S-oligo complex was prepared by mixing 5 pmol of PSA TSU-NT7 primer (SEQ ID NO:55), 7.5 pmol S-oligo (SEQ ID NO:66) and 10 pmol PSA TSU-T7 provider (SEQ ID NO:57). AMACR S-oligo complex was prepared by mixing 5 pmol of AMACR TSU-NT7 primer (SEQ ID NO:36), 7.5 pmol S-oligo (SEQ ID NO:66) and 10 pmol AMACR TSU-T7 provider (SEQ ID NO:37). The mixtures were incubated at room temperature for 30 minutes to allow the complexes to form. PCA3 and PSA TC probes and blockers were spiked into TCR as in Example 5. Additionally, AMACR TC probe (5 pmol; SEQ ID NO:40) and AMACR blocker (2 pmol; SEQ ID NO:38) were also spiked into TCR. PCA3 and PSA S-oligo complexes (5 pmol each) were spiked into TCR instead of PCA3 and PSA TS-NT7 primers, respectively. AMACR S-oligo complex (5 pmol) was also spiked into TCR. PCA3 and PSA molecular torches were spiked into amplification reagent as in Example 5. Additionally, AMACR molecular torch (12 pmol; SEQ ID NO:39) was also spiked into amplification reagent. Universal NT7 primer (15 pmol; SEQ ID NO:64) and universal T7 provider (10 pmol; SEQ ID NO:65) were spiked into the amplification reagent instead of the TS-NT7 primer(s) and TS-T7 provider(s). All other conditions were the same as those given in Example 4.

After the assay was completed, average emergence times were determined (Table 6).

TABLE 6

| | Emergence time (min) | |
|---|---|---|
| PCA3 amount | Uniplex | Multiplex |
| $10^6$ | 18.1 | 20.2 |
| $10^4$ | 23.4 | 25.4 |
| $10^2$ | 34.5 | 36.5 |

These results demonstrate that the RUf-TMA format in the S-oligo mode readily detected PCA3 RNA. In the uniplex mode, emergence times are significantly later and the time between different copy levels is significantly greater than the corresponding values obtained with the RS-TMA format. These features are very favorable in relation to quantitation, and help to solve the problem with RS-TMA cited in Example 5 (i.e., diminished ability of the RS-TMA method to accurately discriminate between small differences (e.g., 3-fold) in copy levels). In the multiplex mode, the interferences observed in the RS-TMA system are largely overcome, resulting in ready detection of all levels of PCA3 RNA tested.

Example 7: Detection of PCA3 RNA in Uniplex and Multiplex Modes

In this example, reverse TMA was performed in a universal (full) TMA format (RUf-TMA) very similar to that described in Example 6. However, instead of via an S-oligo complex, TSU NT7 primer and TSU T7 provider were joined together using a Directly Hybridized-oligo (DH-oligo) complex. In this mode, the TSU NT7 primer and TSU T7 provider are directly hybridized to one another, with no intervening sequence as in the S-oligo complex. FIG. 17 depicts an example of a DH-oligo complex, in this case with binding occurring via the T7 promoter region of the T7 provider.

The assay in this example was performed substantially equivalently to the protocol described in Example 6, with the exceptions described below. Specifically, PCA3 DH-oligo complex was prepared by mixing 5 pmol of PCA3 DH-TSU-NT7 primer (SEQ ID NO:54) and 5 pmol PCA3 TSU-T7 provider (SEQ ID NO:50) in water/STM/TCR (1/1/0.5). Further, PSA DH-oligo complex was prepared by mixing 5 pmol of PSA DH-TSU-NT7 primer (SEQ ID NO:61) and 5 pmol PSA TSU-T7 provider (SEQ ID NO:57). The mixtures were incubated at room temperature for 30 minutes to allow the complexes to form. TC probes and blockers were spiked into TCR as in Example 6, but PCA3 and PSA DH-oligo complexes (5 pmol each) were spiked into TCR instead PCA3 and PSA S-oligo complexes, respectively. All other conditions were the same as those given in Example 6, except that the total amplification volume was 0.04 mL instead of 0.08 mL (0.03 mL amplification reagent and 0.01 mL enzyme reagent). After the assay was completed, average emergence times were determined (Table 7).

TABLE 7

| | Emergence time (min) | |
|---|---|---|
| PCA3 amount | Uniplex | Multiplex |
| $5 \times 10^6$ | 49.5 | 50.5 |
| $5 \times 10^5$ | 43.0 | 44.0 |

TABLE 7-continued

| | Emergence time (min) | |
|---|---|---|
| PCA3 amount | Uniplex | Multiplex |
| $5 \times 10^4$ | 36.5 | 37.5 |
| $5 \times 10^3$ | 30.0 | 31.0 |
| $5 \times 10^2$ | 24.5 | 24.5 |

These results demonstrate that the RUf-TMA format in the DH-oligo mode readily detected PCA3 RNA. In the uniplex mode, emergence times are significantly later and the time between different copy levels is significantly greater than the corresponding values obtained with the RS-TMA format. These features are very favorable in relation to quantitation, and help to solve the problem with RS-TMA cited in Example 4 (i.e., diminished ability of the RS-TMA method to accurately discriminate between small differences (e.g., 3-fold) in copy levels). In the multiplex mode, the interferences observed in the RS-TMA system are largely overcome, resulting in ready detection of all levels of PCA3 RNA tested. Plots of emergence time versus PCA3 copy levels for both the uniplex and multiplex assays yielded excellent correlation factors (uniplex R.sup.2=1.000; duplex R.sup.2=1.000), demonstrating the quantitative nature of these assays.

Example 8: Detection of PCA3 RNA in Uniplex and Multiplex Modes Using Reverse Universal (Full) TMA (RUf-TMA) in the CL-Oligo Format In this example, reverse TMA was performed in a universal (full) TMA format (RUf-TMA) very similar to that described in Example 6. However, instead of via an S-oligo complex, TSU NT7 primer and TSU T7 provider were joined together using a covalently linked-oligo (CL-oligo) complex. In this mode, the TSU NT7 primer and TSU T7 provider are covalently linked to one another at the 5'-ends of each oligomer. A variety of methods can be utilized to achieve such a linking. An example of one possible scheme is shown schematically in FIG. 18. In this case, the NT7 primer and T7 provider are joined 5' to 5' with 2 C9 linkers between the 2 oligomers.

The assay in this example was performed substantially equivalently to the protocol described in Example 6 above, with the exceptions described below. Specifically, the multiplex portion of the assay contained the oligonucleotides required for target capture, universal amplification and real time detection of not only PCA3 and PSA, but also AMACR and CAP2. CL-oligos for each analyte were prepared generally as follows: NT7 primers and T7 providers were synthesized using standard phosphoramidite reagents (Sigma Aldrich), except for those listed below, using an Expedite DNA synthesizer (Applied Biosystems, Foster City, Calif.). The T7 provider was synthesized with a 5'-aldehyde (specialty phosphoramidite from SoluLink, San Diego, Calif.) and a reverse polarity dC (specialty Control Pore Glass (CPG) reagent from Biosearch Technologies). The NT7 primer was synthesized with a 5' C6 amino linker (Glen-Research). Both oligos underwent cleavage and deprotection using standard conditions. A bifunctional spacer was then attached to the NT7 primer via incubation with Hydrazine-NHS ester (SoluLink) at room temperature for 2 hours in 100 mM phosphate buffer (pH 7.40) containing 150 mM NaCl. The reaction mixture was then precipitated with sodium acetate (pH 5.1) and the pellet was dissolved in 100 mM MOPS buffer (pH 4.8) containing a 10% excess of the 5' aldehyde-modified T7 provider. This mixture was left overnight at room temperature and subsequently desalted and purified by PAGE.

SEQ ID numbers of oligonucleotides used to construct the CL-oligo complexes are in Table 8

TABLE 8

| Analyte | Oligo Type | SEQ ID No |
|---|---|---|
| PCA3 | TSU NT7 primer | 48 |
|  | TSU T7 provider | 50 |
| PSA | TSU NT7 primer | 55 |
|  | TSU T7 provider | 57 |
| AMACR | TSU NT7 primer | 36 |
|  | TSU T7 provider | 37 |
| CAP2 | TSU NT7 primer | 42 |
|  | TSU T7 provider | 43 |

PCA3 and PSA TC probes and blockers were spiked into TCR as in Example 7, but PCA3 and PSA DH-oligo complexes were replaced with PCA3 and PSA CL-oligo complexes (5 pmol each), respectively. Additionally, AMACR TC probe (5 pmol; SEQ ID NO:40), AMACR blocker (2 pmol, SEQ ID NO:38), CAP2 TC probe (5 pmol; SEQ ID NO:46) and CAP2 blocker (2 pmol, SEQ ID NO:44) were also spiked into TCR. Further, in addition to the oligonucleotides listed in Example 7, AMACR molecular torch (12 pmol; SEQ ID NO:39) and CAP2 molecular torch (12 pmol; SEQ ID NO:45) were also spiked into the amplification reagent. All other conditions were the same as those given in Example 7. After the assay was completed, average emergence times were determined (Table 9).

TABLE 9

| PCA3 amount | Emergence time (min) | |
|---|---|---|
|  | Uniplex | Multiplex |
| $10^6$ | 35.0 | 35.5 |
| $10^4$ | 49.0 | 48.5 |
| $10^2$ | 59.0 | 59.5 |

These results demonstrate that the RUf-TMA format in the CL-oligo mode readily detected PCA3 RNA. In the uniplex mode, emergence times are significantly later and the time between different copy levels is significantly greater than the corresponding values obtained with the RS-TMA format. These features are very favorable in relation to quantitation, and help to solve the problem with RS-TMA cited in Example 5 (i.e., diminished ability of the RS-TMA method to accurately discriminate between small differences (e.g., 3-fold) in copy levels). In the multiplex mode (quadruplex in this example), the interferences observed in the RS-TMA system are largely overcome, resulting in ready detection of all levels of PCA3 RNA tested.

Example 9: Detection of PCA3, PSA, AMACR and CAP2 in Uniplex and Multiplex Modes Using Reverse Universal (Three-Quarters) TMA (RUt-TMA)

In this example, uniplex samples were made in quadruplicate to contain 2E6, 2E5, 2E4, 2E3 or 2E2 copies of PCA3, PSA, AMACR and/or CAP2 target nucleic acid. No target nucleic acids were added to the negative control. For the uniplex reactions, a series of target capture reagents are prepared as is generally described herein. For the reverse universal three-quarters reactions, each of these target capture reagents comprises a target capture oligomer, about 5 pmoles of a TSU Non-T7 primer and a blocker oligomer as follows: for the PCA3 reaction SEQ ID NOS:48, 53 & 51; for the PSA reaction SEQ ID NOS:60, 58 & 55; for the AMACR reaction SEQ ID NOS:40, 38 & 36 and for the CAP2 reaction SEQ ID NOS:46, 44 & 42. Target capture was performed at 60° C. for about 30 minutes followed by an incubation at room temperature for about 30 minutes. The captured target nucleic acids were washed to remove, amongst other things, unhybridized TSU Non-T7 primers and blocker oligomers. The capture target nucleic acids were isolated and then transferred and resuspended into an amplification reagent comprising about 0.07 pmoles per reaction of a TSU-T7 oligomer, about 15 pmoles per reaction of a universal T7 oligomer and about 15 pmoles per reaction of a universal non-T7 oligomer. The universal primers target the complement of the universal sequences introduced into the amplification product by the TSU Non-T7 and the TSU T7 amplification oligomers. The TSU T7 oligomer targets the cDNA strand generated by the TSU Non-T7. RNA transcripts generated from this promoter provider comprise the universal sequence and the target specific sequence of the TSU T7. Subsequent rounds of amplification use either of the TSU T7 or the universal T7, until the TSU T7 amounts are exhausted. Amplification was performed at 42° C. for 80 minutes. Detection was in real time using a molecular torch (SEQ ID NOS:52, 59, 39, 45 for PCA3, PSA, AMACR and CAP2, respectively). Uniplex Rut-TMA for each of the analytes tested performed exceptionally well. Results are as follows (copy number/average emergence time): for PCA3 at 2E2/54 minutes, 2E3/46 minutes, 2E4/40 minutes, 2E5/36 minutes and 2E6/32 minutes; for PSA at 2E2/63 minutes, 2E3/56 minutes, 2E4/48 minutes, 2E5/43 minutes and 2E6/37 minutes; for AMACR at 2E2/62 minutes, 2E4/42 minutes and 2E6/34 minutes; and CAP2 at 2E2/50 minutes, 2E4/41 minutes and 2E6/34 minutes.

Similarly, an oligomer multiplex reaction was performed, wherein each of the samples contained, in quadruplicate, 2E6, 2E5, 2E4, 2E3 and/or 2E2 copies of one of the following target nucleic acids: PCA3, PSA, AMACR or CAP2, and all of the oligomers required to support target capture, amplification and detection of each of the other analytes listed (quadruplex oligos). Negative control was sample transport medium alone. A target capture reagent was prepared comprising target capture oligomers, blockers and 5 pmoles per reaction of each TSU Non-T7 oligomer for all four of the targets (SEQ ID NOS:53, 51, 48, 60, 58, 55, 40, 38, 36, 46, 44 & 43). Target capture and wash was performed as described directly above, and the captured target nucleic acids were transferred and resuspended into an amplification reagent. Amplification reagent comprised about 0.07 pmoles per reaction of each of the TSU T7 (SEQ ID NOS:48, 55, 36 & 42). The amplification reagent further comprised universal T7 oligomers (SEQ ID NO:65) and universal non-T7 oligomers (SEQ ID NO:64). Amplification was performed at 42° C. for 30 minutes. Detection was in real time using a molecular torch (SEQ ID NOS:52, 59, 39 & 45 for PCA3, PSA, AMACR and CAP2, respectively). The multiplex Rut-TMA format for each of the analytes tested performed well. Emergence times were very similar to those obtained in the uniplex reactions discussed directly above, thereby demonstrating that the Rut-TMA format overcomes the potential adverse reaction between amplification oligomer for different target nucleic acids in a multiplex reaction.

Results are as follows (copy number/average emergence time): for PCA3 at 2E2/58 minutes, 2E3/49 minutes, 2E4/44 minutes, 2E5/40 minutes and 2E6/34 minutes; for PSA at 2E2/66 minutes, 2E3/57 minutes, 2E4/47 minutes, 2E5/42 minutes and 2E6/36 minutes; for AMACR at 2E2/54 minutes, 2E4/44 minutes and 2E6/34 minutes; and CAP2 at 2E2/55 minutes, 2E4/46 minutes and 2E6/36 minutes.

Example 10: Detection of PCA3 and AMACR in Uniplex and Multiplex Modes Using Reverse Universal (Quarter) TMA (RUq-TMA) and Reverse Universal (Two-Quarter) TMA (RUqq-TMA)

In RUq-TMA, the amplification oligomers comprise only one TSU oligomer. Thus, the initial amplification product contains only one universal sequence and subsequent amplification is performed with a universal amplification oligomer and a target specific oligomer. The TSU oligomer can be either the T7 or the Non-T7 amplification oligomer. In RUqq-TMA, two TSU oligomers are used; a TSU T7 and a TSU Non-T7. The RUq and RUqq reactions eliminate the need for a heated target capture step when the TSU oligomers are provided as part of the amplification reagent. Target capture can be performed using a wobble probe, which does not require heat. By eliminating the high heat requirements of specific target capture and TSU complex binding in the target capture step, this amplification assay becomes useful in situations where a high heat source is either unavailable or undesired.

a. RUqq-TMA Using Specific Target Capture Plus Higher Heat or Non-Specific Target Capture and Lower Heat.

In a first example, a series of reactions were prepared for amplification and detection of PCA3 using either a target capture reagent comprising a wobble target capture oligomer (SEQ ID NO:113) or a target specific target capture oligomer (SEQ ID NO:53). Samples were prepared to contain 1E6, 1E4 or 300 copies of PCA3 target nucleic acid. Negative controls were sample transport media without added sample. Target capture reagents were prepared to comprise either SEQ ID NO:113 or SEQ ID NO:53, which are the wobble oligomer or the target specific oligomer, respectively. Each of the target capture reagents was added to a series of samples in quadruplicate. Target capture for the series of samples using SEQ ID NO:53 was performed as is generally described: incubate at 60° C. for about 30 minutes; incubate at room temperature for about 30 min and wash. Target capture for the series of samples using SEQ ID NO:113 was performed as follows: incubate at room temperature for 20 min and wash (see e.g., WO 2008/016988 for a description of target capture using a wobble target capture oligomer). Captured samples were then resuspended into amplification reaction mixtures.

Amplification reaction mixtures comprised 0.07 pmoles per reaction of a TSU Non-T7 amplification oligomer (SEQ ID NO:48), about 0.07 pmoles per reaction of TSU T7 amplification oligomers (SEQ ID NO:50), about 0.5 pmoles of blocker oligomer (SEQ ID NO:51), about 15 pmoles per reaction of a universal Non-T7 amplification oligomer (SEQ ID NO:64), about 15 pmoles per reaction of a universal T7 amplification oligomer (SEQ ID NO:65) and about 10 pmoles of a molecular torch (SEQ ID NO:52). Amplification was performed at 42° C., and fluorescence was monitored throughout amplification. Overall for this example, both target specific and non-specific target capture performed well, with the target specific oligomer yielding somewhat better performance that did the wobble oligomer. For 1E6 copies of PCA3 target nucleic acid, the target specific capture had an average emergence time of 30.5 minutes, while the wobble oligomer capture had an average emergence time of 32.2 minutes. Similarly for 1E4 and 300 copies of PCA3, target specific capture emergence times were 37.5 minutes and 44.4 minutes, while non-specific wobble oligomer capture was 40.8 minutes and 49.5 minutes. These results show that the RUqq-TMA system works well in amplification and detection systems wherein higher heat is not desired, not feasible or not acceptable.

b. RUq-TMA Using a TSU Non-T7 Amplification Oligomer.

Uniplex amplification assays were run using TSU Non-T7 amplification oligomers. Samples comprised 300 copies of PCA3. Negative controls were sample transport medium without addition of sample nucleic acid. Target capture reagents were prepared to comprise 5 pmoles per reaction of target capture oligomer (SEQ ID NO:53) and, optionally, 2 pmoles per reaction of blocker oligomer (SEQ ID NO:51). A series of amplification reagents were prepared to comprise TSU Non-T7 amplification oligomers (SEQ ID NO:48) at one of 1, 0.5 or 0.05 pmoles per reaction, a universal Non-T7 amplification oligomer (SEQ ID NO:64) at about 15 pmoles per reaction and about 10 pmoles per reaction of target specific T7 amplification oligomer (SEQ ID NO:50). Optionally, blocker oligomers can be provided in the amplification reagent at 0.5 pmoles per reaction. Preferably, blocker oligomer is provided in the reaction. Here, the blocker was present in the amplification reagent. Universal T7 oligomers were not added into the amplification reagent, thus the T7 side of the reaction is target specific. Target capture was performed on the sample preparations as is generally described herein, and captured targets were resuspended into amplification reaction mixtures. Detection was performed throughout these amplifications using a molecular torch targeting PCA3 amplification product (SEQ ID NO:52). In this example, the results showed that PCA3 amplified well at 300 copies using this RUq-TMA format. Average emergence times were 16.5 minutes for the amplification reaction using 1 pmole per reaction of TSU Non-T7 amplification oligomers; 17 minutes when using 0.5 pmoles per reaction and 20 minutes when using 0.05 pmoles per reaction.

c. RUq-TMA Using a TSU T7 Amplification Oligomer.

Uniplex amplification assays were run using TSU T7 amplification oligomers. Samples comprised 1E6, 1E4 or 300 copies of PCA3. Negative controls were sample transport medium without addition of sample nucleic acid. Target capture reagents were prepared to comprise 5 pmoles per reaction of target capture oligomer (SEQ ID NO:53). A series of amplification reagents were prepared to comprise one of 0.2, 0.1 or 0.05 pmoles per reaction of TSU T7 amplification oligomers (SEQ ID NO:50), 5 pmoles per reaction of blocker oligomer (SEQ ID NO:51), 15 pmoles per reaction of universal T7 amplification oligomer (SEQ ID NO:65) and 15 pmoles per reaction of TSU Non-T7 amplification oligomer (SEQ ID NO:48). As above, blocker could optionally be provided in the target capture reagent, though here it was provided in the amplification reagent. Universal Non-T7 amplification oligomers were not added into the amplification reagent, thus the Non-T7 side of this amplification reaction was target specific. Target capture was performed as is generally described herein, and captured targets were resuspended into amplification reaction mixtures. Detection was performed throughout these amplifications using a molecular torch targeting PCA3 amplification product (SEQ ID NO:52). In this example, the results showed that PCA3 amplified well at 300 copies using this RUq-TMA format, with emergence times of 49, 56 and 63 minutes for TSU T7 amounts of 0.2, 0.1 and 0.05 pmoles per reaction, respectively.

d. RUqq-TMA in Duplex Mode.

Samples were prepared as follows: 1E6 copies of PCA3 target nucleic acid and 1E6 copies of AMACR target nucleic acid, 1E4 copies of PCA3 target nucleic acid and 1E4 copies of AMACR target nucleic acid, and 300 copies of PCA3 target nucleic acid and 300 copies of AMACR target nucleic acid. Target capture reagents comprised target capture oligomers (SEQ ID NOS:40 & 53). Samples and target capture reagents were combined and then a target capture/wash procedure was performed generally as is described herein. Captured targets were resuspended into amplification reaction mixture. The amplification reactions mixtures comprised blocker oligomers (SEQ ID NOS:38 & 51, each at 0.3 pmoles per reaction); TSU-Non-T7 amplification oligomer (SEQ ID NOS:48 & 36, each at 0.01 pmoles per reaction), TSU-T7 amplification oligomers (0.15 pmoles per reaction of SEQ ID NO:50 & 0.25 pmoles per reaction of SEQ ID NO:37); universal Non-T7 amplification oligomers (SEQ ID NO:64, at 15 pmoles per reaction) and universal T7 amplification oligomer (SEQ ID NO:65 at 15 pmoles per reaction). Detection was performed throughout these amplifications using molecular torches targeting PCA3 amplification product and AMACR amplification product (SEQ ID NOS: 52 & 39, respectively).

In this example, samples containing both PCA3 and AMACR amplified well, demonstrating that the RUqq-TMA format is effective in multiplex reactions. Results are as follows: for 1E6 PCA3 and 1E6 AMACR, PCA3 emerged at 32 minutes on average and AMACR emerged at 33 minutes on average; for 1E4 PCA3 and 1E4 AMACR, PCA3 emerged at 41 minutes on average and AMACR emerged at 42 minutes on average; and for 300 PCA3 and 300 AMACR, PCA3 emerged at 48 minutes on average and AMACR emerged at 48 minutes on average.

Example 11: Detection of PSA Using Reverse Universal (Half) Switched TMA (RUh-Switched-TMA)

Samples comprised 1E4, 1E3 and 1E2 copies of PSA. Negative controls were sample transport medium without addition of sample nucleic acid. Target capture reagents were prepared to comprise 5 pmoles per reaction of target capture oligomer (SEQ ID NO:60), 5 pmoles per reaction blocker (SEQ ID NO:58), and 5 pmol of a DH complex comprising equal amounts of PSA TS-Non-T7-cPRO (SEQ ID NO:114) and PSA TSU-T7-T15 (SEQ ID NO:115). Amplification reagents were prepared to comprise 10 pmoles per reaction PSA TS-Non-T7 (SEQ ID NO:56) and 5 pmoles per reaction universal T7-T15 (SEQ ID NO:116). Target capture was performed as is generally described herein, and captured targets were resuspended into amplification reaction mixtures. Detection was performed throughout these amplifications using a molecular torch targeting PSA amplification product (SEQ ID NO:59). In this example, the results showed that PSA amplified well at all target levels tested using the RUh-switched-TMA format, with emergence times of 31, 35 and 40 minutes for 1E4, 1E3 and 1E2 copies per reaction of PSA target, respectively.

Example 12: Uniplex Pre-Amplification, Split Secondary Amplification and Detection of PCA3 Using a TSU-Complex with a DH Linkage Examples 12, 13 and 14 show that a linear pre-amplification method using linked forward and reverse primers (such as DH-complexes) is effective in increasing the amount of product from the input target, which can then be further amplified in a secondary exponential amplification reaction. Further, pre-amplification of multiple targets in the same reaction had no adverse effect on accurate quantification of any of the targets in the separated specific exponential amplification reactions. Because the pre-amplification step forms a specific cDNA from each input target, which is then transcribed by an RNA polymerase in the same reaction in a linear manner, interference from other targets and their primers was not observed. In each example the DH-complexes were formed prior to being added to the target capture reagent. The pre-amplification and the amplification steps were then performed substantially as is described In this example, a first linear pre-amplification reaction was performed on a sample containing 1E6, 1E4 or 1E2 copies of PCA3 target nucleic acid. Following pre-amplification, part of the sample was transferred to an amplification reaction comprising target specific amplification oligomers for the PCA3 target nucleic acid. Because the secondary amplification uses target specific oligomers rather than universal amplification oligomers, the TSU-complexes provided in the pre amplification are not used for their universal sequences. Thus, these complexes can also be referred to as DH-complexes, which is the linkage mechanism used in this example. Also notably, this example is not limited to the DH linkage format, as other direct or indirect linkages may be used as well.

A single target capture reagent was prepared to comprise SEQ ID NOS:81, 69, 87 & 75 (5 pmoles each per reaction) as a target capture oligomers, SEQ ID NOS:82, 70, 88 & 16 (5 pmoles each per reaction) as a blocker oligomers and oligomers for four different DH-complexes: SEQ ID NOS: 83 & 84 (5 pmoles: 7.5 pmoles per reaction), SEQ ID NOS: 71 & 72 (5 pmoles: 7.5 pmoles per reaction), SEQ ID NOS: 89 & 90 (5 pmoles: 7.5 pmoles per reaction) and SEQ ID NOS: 77 & 78 (5 pmoles: 7.5 pmoles per reaction). Thus, the target capture reagent provided target capture oligomers, blocker oligomers and DH-complex oligomers for PCA3 and for AMACR, PSA and CAP2. Only PCA3 was present in the samples. Target capture reagent was combined with sample or with sample transport media alone as a negative control. A target capture protocol was performed as is generally described herein. Briefly, target capture proceeded at 60° C. for 30 minutes followed by incubation at room temperature for 20 minutes. Captured target with hybridized DH-complex was then washed twice using a magnetic bead capture system, e.g., a KingFisher magnetic bead capture system. Following capture and wash, the captured target and DH-complexes are transferred and resuspended into a pre-amplification reaction. The pre-amplification reaction comprised a reverse transcriptase and RNA polymerase, and the pre-amplification step was performed at 42° C. for 15 minutes. No primers are added into the pre-amplification reaction, thus only the DH-complex hybridized to target is present in the pre-amplification. Pre-amplification produces RNA transcripts from a cDNA produced by the target and DH-complex.

Following pre-amplification, four separate aliquots of the pre-amplification product each individually added to one of four separate secondary amplification reactions, each comprising a RNA polymerase, a reverse transcriptase, a different set of target specific oligomers and a different molecular torch for real-time detection of secondary amplification product: PCA3 specific secondary amplification reaction comprised SEQ ID NOS:84 (10 pmoles), 85 (15 pmoles) & 86 (12 pmoles); AMACR specific secondary amplification reaction comprised SEQ ID NOS:72 (10 pmoles), 73 (15 pmoles) & 74 (12 pmoles); PSA specific secondary amplification reaction comprised SEQ ID NOS:90 (10 pmoles), 91 (15 pmoles) & 92 (12 pmoles); and CAP2 specific secondary amplification reaction comprised SEQ ID NOS: 78 (10 pmoles), 79 (15 pmoles) & 80 (12 pmoles). The secondary amplification was performed at 42° C. for 80 minutes and the generation of amplification product was monitored throughout using the molecular torches. Results for this experiment showed no false positives in the negative control samples. Also, secondary amplification reactions comprising target specific oligomers for AMACR, PSA or CAP2 were also negative. The secondary amplification reaction for PCA3 showed good sensitivity down to 100 copies of target nucleic acid in the pre-amplification reaction. PCA3 results are as follows (n=4): 1E6 copies in pre-amplification showed a secondary amplification average emergence time of about 23 minutes; 1E4 copies in pre-amplification showed a secondary amplification average emergence time of about 32 minutes; and 1E2 copies in pre-amplification showed a secondary amplification average emergence time of about 47 minutes. Using the DH-complexes in a multiplex amplification reaction provides good amplification results for specific targets. Following the target capture, unhybridized oligomers and others undesired components in the sample, can be washed away, leaving captured target hybridized with a DH-complex. The pre-amplification reaction then performs well because the abundance of interfering oligomers was substantially reduced or eliminated. Primer dimers, spurious product formation, mis-priming at non-target sequences and other common multiplex problems are substantially reduced or eliminated, as well. Pre-amplification is performed using a reverse transcriptase to generate a cDNA, from the DH-complex, then, following binding to the T7 member of the DH-complex to the cDNA, an abundance of RNA transcripts are produced therefrom. Pre-amplified sample is transferred to one or more target specific samples, each of which comprises the oligomers for only a single target.

Example 13: Multiplex Pre-Amplification, Split and Detection of PSA and PCA3 Using a TSU Complex in the Pre-Amplification Reaction and Universal Amplification Oligomers in the Secondary Amplification Reaction or Using a DH-Complex in the Pre-Amplification Reaction and Target Specific Amplification Oligomers in the Secondary Amplification Reaction This example performed target capture and pre-amplification on samples containing PCA3, PSA or PCA3 and PSA target nucleic acids using TSU-complexes and DH-complexes targeting those nucleic acids. Following pre-amplification, the reactions were split into secondary reactions comprising either target specific secondary amplification oligomers or universal amplification oligomers. Secondary amplification reactions were performed in the presence of a molecular torch for real time detection of amplification product. The target specific secondary amplification was superior to the universal secondary amplification. As mentioned above, amplification oligomer-complexes can comprise amplification oligomer members, wherein one or both of the oligomer members contain a universal tag sequence (TSU-complex) or wherein neither oligomer member contains a universal tag sequence (DH-complex). Furthermore, for these examples, if an oligomer member comprises a universal tag sequence, but secondary amplification is performed using amplification oligomer that are target specific, the complex is referred to as a DH-complex because universal amplification oligomers were not used in the secondary amplification.

Samples were prepared to comprise either 0 copies of PCA3 target nucleic acid and 1E3 copies of PSA target nucleic acid; 1E3 copies of PCA3 target nucleic acid and 0 copies of PSA target nucleic acid; 1E5 copies of PCA3 target nucleic acid and 1E3 copies of PSA target nucleic acid; or 1E3 copies of PCA3 target nucleic acid and 1E5 copies of PSA target nucleic acid. Negative controls contained no added target nucleic acid. Target capture reagent was prepared to comprise target capture oligomers, TSU/DH complexes and blocker oligomers for each target nucleic acid, (for PCA3, 5 pmoles/rxn SEQ ID NO:81, 5 pmoles/rxn SEQ ID NO:82, 5 pmoles/rxn SEQ ID NO:83 & 7.5 pmoles/rxn SEQ ID NO:84; and for PSA, 5 pmoles/rxn SEQ ID NO:87, 5 pmoles/rxn SEQ ID NO:88, 5 pmoles/rxn SEQ ID NO:89 & 7.5 pmoles/rxn SEQ ID NO:90). Target capture reagent was added to each sample. Target capture and wash was performed as is generally described herein. Following target capture and wash, the captured samples were transferred and resuspended into a pre-amplification reagent comprising reverse transcriptase and RNA polymerase. Pre-amplification reaction was performed at 42° C. for 15 minutes.

Following pre-amplification, the samples were then split into separate secondary amplification reactions comprising RNA polymerase, reverse transcriptase, and one of the following sets of secondary amplification and detection oligomers: (PCA3 target specific was 10 pmoles SEQ ID NO:84, 15 pmoles SEQ ID NO:85 and 12 pmoles SEQ ID NO:86; PSA target specific was 10 pmoles SEQ ID NO:90, 15 pmoles SEQ ID NO:91 and 12 pmoles SEQ ID NO:92; PCA3 universal was 10 pmoles SEQ ID NO:93, 15 pmoles SEQ ID NO:94 and 12 pmoles SEQ ID NO:86; and PSA universal was 10 pmoles SEQ ID NO:93, 15 pmoles SEQ ID NO:94 and 12 pmoles SEQ ID NO:92). Amplification was performed at 42° C. for 80 minutes. Results for this example showed good amplification of each target using the target specific oligomers in the secondary amplification. Target specific amplification of one target nucleic acid in the presence of an excess of another target nucleic acid, 100-fold excess in this example, also provided good results. Because the TSU-complexes confer universal primer binding regions to the pre-amplified targets, the secondary amplification reaction used universal primers. Thus, in the secondary amplification reaction, all targets competed for the universal primers. However, using the target-specific primers instead, only the specific target in each reaction was amplified. As is seen by the below results, the secondary amplification reactions using target specific amplification oligomers had average emergence times that are much quicker than secondary amplification reactions using universal amplification oligomers. In the linear multiplex pre-amplification methods, it is preferable, then that the secondary amplification reactions use target specific amplification oligomers. Target specific amplification oligomers work well because the secondary reactions are separated from each other, have no amplification oligomer carry over from the pre-amplification reaction, and do not have to contend with primer interaction issues, and other similar problems common to multiplex reactions.

Average emergence times for this example are as follows (n=4): PCA3 at 0 copies/PSA at 1E3 copies average emergence time using target specific amplification oligomers was 18 minutes, average emergence time using universal amplification oligomers was 52 minutes; PCA3 at 1E3 copies/

PSA at 0 copies average emergence time using target specific amplification oligomers was 15 minutes, average emergence time using universal amplification oligomers was 44 minutes; PCA3 at 1E5 copies/PSA at 1E3 copies average emergence time for PSA using target specific amplification oligomers was 18 minutes, average emergence time for PSA using universal amplification oligomers was 66 minutes, average emergence time for PCA3 using target specific amplification oligomers was 12 minutes, average emergence time for PSA using universal amplification oligomers was 32 minutes; and PCA3 at 1E3 copies/PSA at 1E5 copies average emergence time for PSA using target specific amplification oligomers was 14 minutes, average emergence time for PSA using universal amplification oligomers was 40 minutes, average emergence time for PCA3 using target specific amplification oligomers was 15 minutes, average emergence time for PSA using universal amplification oligomers was 44 minutes. Thus, in this example, the average emergence times were not affected by the presence of a 100-fold excess of the other target in pre-amplification. To this point, PSA at 1E3 copies showed an average emergence time of 18 minutes with or without 1E5 copies of competing PCA3 target and, similarly, PCA3 at 1E3 copies showed an average emergence time of 15 minutes with or without 1E5 copies of competing PSA target.

Example 14: Pre-Amplification Multiplex Reaction Using TSU Amplification Oligomers in the DH Format This example is an 11-plex multiplex reaction wherein a target capture reagent comprises target capture, blocker and DH-complex oligomers for all 11 target nucleic acids. Following pre amplification, the pre-amplification product is split into eleven separate secondary amplification reactions, each comprising target specific amplification oligomers for one of the targets. Samples for this reaction comprised varied amounts of PCA3 target nucleic acid either alone (uniplex) or combined with 8.75E5 copies of target nucleic acid from each of AMACR, CAP2, Chickengunyavirus (CHIKV), Erg exon 11, HIV pol, PCGEM1, PSA, PSGR, T2ERGc and West Nile Virus (WNV). Sample transport medium without added target nucleic acids was used as the negative control. The target capture reagent comprised a DH-complex, a target capture oligomer and a blocker oligomer for each of the 11 target nucleic acids. It is notable that CHIKV and WNV are forward TMA reactions, thus the T7 component of the DH-complex hybridizes to the target nucleic acid during the target capture step, whereas the remaining targets are reverse TMA and the non-T7 hybridizes to those target nucleic acids during target capture. The member of the DH oligomer that does not initially hybridize the target nucleic acid during target capture is provided in an excess concentration over the concentration of the member that does hybridize. For these examples, the DH oligomer member amounts are 7.5 pmoles/reaction for the excess concentration and 5 pmoles/reaction for the initially hybridizing member. Target capture was performed at 60° C. for about 30 minutes followed by a room temperature incubation for about 20 minutes. The captured target nucleic acids were then washed and eluted into a pre-amplification reaction mixture. The pre-amplification reaction mixture comprised reverse transcriptase and RNA polymerase. The pre-amplification reaction was then incubated for 15 minutes at 42° C. Following pre-amplification, the pre-amplification reaction is split into aliquots and then amplified in separate secondary amplification reactions for one of 11 different targets, each comprising target specific amplification oligomers and a molecular torch for one of the 11 target nucleic acids. The individual amplification reactions were performed at 42° C. for about 80 minutes and were monitored for detection of amplification product throughout the amp reaction. Results from the PCA3 specific amplification is shown in Table 10. Each of the other target nucleic acids were successfully amplified in their own target specific secondary amplification reactions, data not shown.

TABLE 10

| | PCA3 Target Input | | | |
| | PCA3 Uniplex | | PCA3 + Challenging Targets in 11-plex | |
| Copy # | mean C(t) n = 4 | % CV | mean C(t) n = 4 | % CV |
| --- | --- | --- | --- | --- |
| 100 | 21.5 | 4.07% | 20.9 | 4.84% |
| 300 | 19.1 | 2.85% | 19.6 | 3.03% |
| 900 | 17.8 | 1.64% | 18.0 | 1.32% |
| 2,700 | 16.6 | 1.25% | 17.1 | 1.68% |
| 8,100 | 16.0 | 0.64% | 16.0 | 1.35% |
| 24,300 | 15.0 | 0.44% | 15.1 | 0.92% |
| 72,900 | 14.1 | 0.46% | 14.2 | 2.01% |
| 218,700 | 13.4 | 1.08% | 13.2 | 0.44% |

These results showed that PCA3 was amplified and detected following a pre-amplification, and also when pre-amplified in the presence of a large excess of 10 other target nucleic acids. Detection results for PCA3 in a uniplex reaction are similar to those for PCA3 in a multiplex reaction as shown in the table above. Amplification was also detected for these ten other target nucleic acids in this 11-plex reaction, with emergence times for 8.75E5 copies ranging from about 6 to about 15 minutes of the amplification reaction.

In another part of this example, a calibration curve was constructed using 10 fold dilutions of a calibrator nucleic acid (here, PCA3 calibrator nucleic acid). The mean calculated log [copies] for each target level were compared to known input log [copies]. The dependence of these two values would ideally be expressed by equation $y=x$, where x is input log [copies] and y is calculated log [copies]. In this example the dependence was determined as: $y=1.065x-0.090$ with $R2=0.9592$ for PCA3 alone, and $y=1.0526x-0.084$ with $R2=0.99$ for PCA3 in the presence of challenging targets. This shows a lack of interference of the PCA3 pre-amplification and amplification reactions from other targets present in the multiplex reaction.

Example 15: Alternate Designs for DH Linked TSU-Complexes

The DH linked amplification oligomer-complexes operate by hybridizing together the two oligomer members of the complex (e.g., the non-T7 to T7 or the forward primer to reverse primer, etc). A plurality of variant amplification oligomer-complex oligomers members was prepared to comprise a variety of complementary sequences for joining the T7 and Non-T7 members. These complementary sequences comprised all or part of the promoter sequence of the T7 member, and/or all or part of the universal tag sequence of the T7 member, and/or all or part of the target specific sequence of the T7 member. Amplification oligomer-complex oligomer members targeting PSA, PCA3 and CAP2 were prepared and all tested amplification oligomer-complex variants produced amplification products, though some were less robust than others, showing late emergence times and/or varied results for duplicate reactions. Nevertheless, these variant amplification oligomer-complexes are useful for amplification reactions. In addition to identifying that the variant amplification oligomer-complex oligomers worked in amplification reactions, a further discovery was made. Some of these amplification oligomer-complex variants were resilient to unfavorable conditions such as temperature spikes, which cause the amplification oligomer-complex members to dissociate.

In reactions wherein two or more DH-complexes are used, such as a multiplex reaction, dissociation of the oligomer members followed by reassociation at a lower temperature can result in mis-pairing. This means that for a sample reaction system. Thus, when the dissociated members of amplification oligomer-complex A and the dissociated members of amplification oligomer-complex B reassociate, then the members of A are more strongly driven together, and likewise, the members of B are more strongly driven together. The following oligomers were designed to identify unique pairing sequences for members of a TSU-complex targeting PCA3 target nucleic acid. Table 11. Though TSU-complexes are illustrated, these designs can also be applied to amplification oligomer complexes lacking a universal tag sequence, wherein the complementary portions of the oligomer members can include all or part of the promoter sequence and all or part of the target specific sequence.

TABLE 11

| SEQ ID NO: | Sequence 5'→3' | Member Type |
|---|---|---|
| 95 | aatttaatacgactcactatagggagaccacaacggttttaatgtctaagtagtgac | T7 |
| 96 | tctccctatagtgagtcgtattaaattGTCATATGCGACGATCTCAGGGCTCATCGATGACCCAAGATGGCGGC | Non-T7 |
| 97 | TCTCCCTATAGTGAGTCGGTCATATGCGACGATCTCAGGGCTCATCGATGACCCAAGATGGCGGC | Non-T7 |
| 98 | TCTCCCTATAGTGAGTCGGTCATATGCGACGATCTCAGGGCTCATCGATGACCCAAGATGGCGGC | Non-T7 |
| 99 | TGGTCTCCCTATAGTGAGTCGGTCATATGCGACGATCTCAGGGCTCATCGATGACCAAGATGGCGGC | Non-T7 |
| 100 | gtggtctccctatagtgagtcgGTCATATGCGACGATCTCAGGGCTCATCGATGACCCAAGATGGCGGC | Non-T7 |
| 101 | CCGTTGTGGTCTCCCTATAGTCATATGCGACGATCTCAGGGCTCATCGATGACCCAAGATGGCGGC | Non-T7 |
| 102 | CTTAGACGTGGTCTCCCTATAGTCATATGCGACGATCTCAGGGCTCATCGATGACCAAGATGGCGGC | Non-T7 |
| 103 | CTTAGACATTTGTGGTCTCCCGTCATATGCGACGATCTCAGGGCTCATCGATGACCCAAGATGGCGGC | Non-T7 |
| 104 | cttagaccgttgtggtctcccGTCATATGCGACGATCTCAGGGCTCATCGATGACCAAGATGGCGGC | Non-T7 |
| 105 | ctacttagacatgtggtctcccGTCATATGCGACGATCTCAGGGCTCATCGATGACCCAAGATGGCGGC | Non-T7 |
| 106 | CACTACTTAGACAGGTCTCCCGTCATATGCGACGATCTCAGGGCTCATCGATGACCAAGATGGCGGC | Non-T7 |
| 107 | CTTAGACATTAAAACCGTTGTGGGTCATATGCGACGATCTCAGGGCTCATCGATGACCCAAGATGGCGGC | Non-T7 |
| 108 | GTGGTCTCCCTATAGTGAGTCATATGCGACGATCTCAGGGCTCATCGATGACCCAAGATGGCGGC | Non-T7 | comprising amplification oligomer-complex A and amplification oligomer-complex B, wherein an event leads to a disassociation of the members of TSU complexes A & B, reassociation may result in the following amplification oligomer-complex species: amplification oligomer-complex A, amplification oligomer-complex B, amplification oligomer-complex AB & amplification oligomer-complex BA. Amplification oligomer-complexes AB & BA are mis-paired, and their use in an amplification reaction leads to inefficiencies in that reaction. One solution for preventing mis-pairing is the use of complementary pairing sequences that are unique to each species of amplification oligomer-complex in the SEQ ID NO:95 is the T7 member of the TSU-complexes and comprises a promoter sequence from residues 1-27, an universal sequence from residues 28-47 for subsequent amplification using an universal amplification oligomer and a target specific sequence. SEQ ID NOS:96-108 are various non-T7 members of the TSU complexes and each comprise a target specific sequence and an universal tag sequence at their 3' ends (5'-GTCATATGCGACGATCTCAGGGCTCATCGATGAC-CCAAGATGGCGGC-3'). Joined to the 5 prime end thereof are the varied DH complex forming sequences. SEQ ID NO:96 comprises a DH complex forming sequence that is the complement of the promoter sequence on the T7 member (cPRO). Thus, in a multiplex reaction all TSU complexes using the PRO-cPRO DH sequences would have the same linking sequences, and could encounter the dissociation/reassociation problem mentioned above. Similarly, SEQ ID NOS:97-98 comprise a DH linking sequence that is complementary to a portion of the T7 promoter region, and could encounter the same problems. SEQ ID NOS:99-101 & 108 each comprise a DH linking sequence that is complementary to a portion of the T7 promoter region and a portion of the universal tag sequence region. Because typically a universal tag sequence is provided to allow for subsequent amplification using a single set of universal amplification oligomers, TSU complexes joined by all or part of a PRO-cPRO sequence and/or all or part of a universal tag-complement of universal tag sequence could encounter the association/dissociation problems discussed above. SEQ ID NOS:102-107 comprise DH linking sequences that are complementary a portion of the PRO sequence and/or all or a part of the universal sequence, but also are partially complementary to the target specific portion of the T7 member. Thus, each different TSU complex present in a multiplex reaction could have unique DH linking sequences, thereby driving reassociation between the proper TSU complex members.

Each of the following combinations of TSU complexes were prepared (SEQ ID NOS:96 & 97; SEQ ID NOS:96 & 98; SEQ ID NOS:96 & 99; SEQ ID NOS:96 & 100; SEQ ID NOS:96 & 101; SEQ ID NOS:96 & 102; SEQ ID NOS:96 & 103; SEQ ID NOS:96 & 104; SEQ ID NOS:96 & 105; SEQ ID NOS:96 & 106; SEQ ID NOS:96 & 107; and SEQ ID NOS:96 & 108) and tested using PCA3 target nucleic acid. PCA3 samples were prepared to contain 2E2, 5E2, 1E3 or 5E3 copies of target nucleic acids. Target capture reagents were prepared to comprise a target capture oligomer, (SEQ ID NO:81), a blocker oligomer (SEQ ID NO:82) and one of the TSU complexes. Target capture was performed as is mentioned above and the captured targets from each of the capture reactions were resuspended into amplification reaction mixtures comprising universal amplification oligomers (SEQ ID NOS:93 & 94) and a detection probe (SEQ ID NO:86). Amplification and detection were performed generally as is discussed herein. TSU complexes comprising SEQ ID NOS:95 & 103; and SEQ ID NOS:95 & 108 showed good overall performance and were selected for additional testing. Average emergence times for these TSU complexes were as follows: for SEQ ID NOS:95 & 103 200 copies was 48.3 minutes, 500 copies was 49.2 minutes, 1000 copies was 46.0 minutes and 5000 copies was 41.9 minutes; and for SEQ ID NOS:95 & 108 200 copies was 49.7 minutes, 500 copies was 47.0 minutes, 1000 copies was 45.6 minutes and 5000 copies was 40.3 minutes. The TSU complexes comprising SEQ ID NOS:95 & 103; and SEQ ID NOS:95 & 108 were then used in uniplex, duplex and triplex reactions wherein each of the TSU-complexes in the reactions were subjected to dissociation and reassociation conditions.

For these uniplex, duplex and multiplex reactions, samples comprised 2E2 copies or PSA, target nucleic acid, 2E2 copies of PCA3 target nucleic acid, 2E2 copies of CAP2 target nucleic acid, 1E3 copies of PSA target nucleic acid, 1E3 copies of PCA3 target nucleic acid, 1E3 copies of CAP2 target nucleic acid or combinations thereof, as is discussed in the results section. Target capture reagents comprised target capture oligomer, blocker and one or more TSU complex, depending on whether the reaction was uniplex or multiplex, see Table 12.

TABLE 12

| Target Nucleic Acid(s) | Target Capture Oligomer(s) | Blocker Oligomer(s) | TSU Complex(s) |
|---|---|---|---|
| 1. PSA Uniplex | SEQ ID NO: 87 | SEQ ID NO: 88 | SEQ ID NOS: 90 & 110 |
| 2. PSA Uniplex | SEQ ID NO: 87 | SEQ ID NO: 88 | SEQ ID NOS: 90 & 109 |
| 3. PCA3 Uniplex | SEQ ID NO: 81 | SEQ ID NO: 82 | SEQ ID NOS: 83 & 84 |
| 4. PSA & PCA3 Duplex | SEQ ID NOS: 81 & 87 | SEQ ID NOS: 82 & 88 | SEQ ID NOS: 89, 90, 83 & 84 |
| 5. PSA & PCA3 Duplex | SEQ ID NOS: 81 & 87 | SEQ ID NOS: 82 & 88 | SEQ ID NOS: 90, 110, 95 & 108 |
| 6. PSA, PCA3 and CAP2 Triplex | SEQ ID NOS: 75, 81 & 87 | SEQ ID NOS: 76, 82 & 88 | SEQ ID NOS: 77, 78, 89, 90, 83 & 84 |
| 7. PSA, PCA3 and CAP2 Triplex | SEQ ID NOS: 75, 81 & 87 | SEQ ID NOS: 76, 82 & 88 | SEQ ID NOS: 90, 110, 95, 108, 78 & 112 |
| 8. PSA, PCA3 and CAP2 Triplex | SEQ ID NOS: 75, 81 & 87 | SEQ ID NOS: 76, 82 & 88 | SEQ ID NOS: 90, 109, 95, 103, 78 & 111 |
| 9. PSA Uniplex | SEQ ID NO: 87 | SEQ ID NO: 88 | SEQ ID NOS: 89 & 90 |
| 10. PCA3 Uniplex | SEQ ID NO: 81 | SEQ ID NO: 82 | SEQ ID NOS: 95 & 103 |
| 11. PSA, PCA3 and CAP2 Triplex | SEQ ID NOS: 75, 81 & 87 | SEQ ID NOS: 76, 82 & 88 | SEQ ID NOS: 90, 109, 78, 111, 95 & 103 |

Each of the target capture reagents in Table 12 were made in duplicate, one member of which was subjected to a 72° C. temperature spike before use, while the other of which was stored at a consistent 25° C. until used. The temperature spike was applied to one of the samples to create a dissociation/reassociation condition. Target capture was then performed generally as is described herein. Samples were resuspended into amplification reactions comprising universal amplification oligomers (SEQ ID NOS:93 & 94) and molecular torches for real time detection of amplification product (for amplifications wherein PSA target nucleic acids were included, SEQ ID NO:92; for amplifications wherein PCA3 target nucleic acids were included, SEQ ID NO:86; for amplifications wherein CAP2 target nucleic acids were included, SEQ ID NO:80). Amplifications and real-time detections were performed generally as is described herein.

The TSU complexes in target capture reagents 3, 4, 6 & 9 from Table 12 comprise DH linkages wherein a complementary promoter sequence on the non-T7 amplification oligomer member hybridizes to the promoter sequence on the T7 oligomer member. The TSU complexes in target capture reagents 1, 5 & 7 from Table 12 comprise DH linkages wherein the Non-T7 linkage sequences are complementary to part of the promoter sequence and part of the universal tag sequence of the T7 member. The TSU complexes in target capture reagents 2, 8, 10 & 11 from Table 12 comprise DH linkages wherein the Non-T7 linkage sequences are complementary to part of the promoter sequence, part of the universal tag sequence and part of the target specific sequence of the T7 member. In a first set of experiments, target capture reagents 4, 6 & 9 were tested for performance following two sets of conditions; the first set of conditions held the TSU complexes at 25° C. until used for a target capture reaction while the second set of conditions provided a 72° temperature spike before use. Results showed that when the TSU complex was held at a about 25° C., the uniplex, duplex and triplex reactions all provided very similar amplification results (Table 13). However, when the TSU oligomers experienced a 72° C. temperature spike before being used in the target capture procedure, the amplification results were not as good. Here, though the uniplex reaction results were similar to those for the consistent temperature reactions (Table 13), the duplex and triplex reactions were delayed and less robust (Table 13). In a second set of experiments, target capture reagents 1, 2, 5, 7 & 8 were tested for performance following a 72° C. temperature spike. The TSU complexes used for this second experiment showed improvement over the above temperature spike results for the duplex and triplex reactions. The triplex reactions using the TSU complexes in target capture reaction mix 7 (triplex oligomer) were slower and less robust than those in target capture reaction mixtures 1 (uniplex) and 5 (duplex) (Table 13). Target capture reaction mixes 2 & 8 showed very good and very consistent results for all reactions (Table 13). TSU-complexes joined by unique DH-linkage sequences, such as using at least a portion of the target sequence of one member of the TSU complex, perform well following a dissociation and reassociation compared to those that are linked using sequences that are common or universal amongst the species of TSU-complex in a mix.

TABLE 13

| | | | Emergence time (minutes) | | |
| | | TCR | 200 copies per reaction | | 1,000 copies per reaction | |
| Plex | | # | Room temp | 72-deg-C. | Room temp | 72-deg-C. |
|---|---|---|---|---|---|---|
| A | Uniplex | 9 | 63 | 65 | 58 | 60 |
| | Duplex | 4 | 63 | 67 | 58 | 64 |
| | Triplex | 6 | 63 | 70 | 58 | 62 |
| B | Uniplex | 1 | — | 63 | — | 57 |
| | Duplex | 5 | — | 63 | — | 58 |
| | Triplex | 7 | — | 63 | — | 63 |
| C | Uniplex | 2 | — | 62 | — | 56 |
| | Triplex | 8 | — | 62 | — | 57 |

Example 16: Alternate Designs for TSU-Complexes

The TSU-complexes can comprise a variety of different amplification oligomer types. In one example, the amplification oligomer members could comprise forward and reverse primer oligomers. These oligomers could be linked using a direct linkage format, such as covalently linking each member to the other. The primer members forming the complex would be oriented to each provide their 3' end for a nucleic acid extension reaction. The primer members could further and optionally comprise universal sequences, which would allow for secondary amplification using universal amplification oligomers. These TSU primer complexes could be hybridized to a target nucleic acid, and a first extension reaction could be performed therefrom to generate a double stranded initial amplification product comprising the sequences of these TSU-complex members. Secondary amplification could take place therefrom using universal amplification oligomers. PCR amplification and other amplification methods are well known in the art.

In one example of using the TSU complex, a multiplex reaction could be performed. In such a reaction, a sample suspected of comprising two or more target nucleic acids of interest could be provided. Exemplary target nucleic acids could include, but are not limited to, those wherein the target nucleic acids are part of a larger nucleic acid, such as different target sequence regions of a mitochondrial DNA, or different target sequences of an HLA nucleic acid; or those that are separate, but jointly interesting target nucleic acids, such as two or more species of *Mycoplasma* from a bioreactor, two or more potentially infectious bacterium from a hospital setting, and the like. TSU complexes configured to hybridize with the target nucleic acids suspected to be in the sample are then added into the sample. A target capture system may be included as well. Exemplary, but non-limiting, target capture systems are discussed herein. A first amplification reaction, e.g., a PCR amplification reaction, is then performed using these TSU complexes in order to integrate the TSU complex member sequences. Subsequent amplification reactions, e.g., PCR, could then be performed using, for example, universal amplification oligomers. Target specific detection could then be performed. One method of target specific amplification product detection is the use of molecular probes. Others include mass spectrometry, nucleic acid sequencing and gel electrophoresis.

The invention claimed is:

1. A method for simultaneously amplifying at least two different target nucleic acid sequences contained in a sample comprising the steps of:
   (a) contacting a sample with at least two different target capture oligomers and with at least two different amplification oligomer complexes;
      (i) wherein each of said target capture oligomers and each of said amplification oligomer complexes hybridize to different target nucleic acid sequences,
      (ii) wherein each of said amplification oligomer complexes comprises a non-promoter primer oligonucleotide having a first 3' target specific sequence and a promoter oligonucleotide having a second 3' target specific sequence and a 5' promoter sequence, wherein the promoter oligonucleotide optionally comprises a blocked 3' terminus, and wherein the non-promoter primer oligonucleotide is directly or indirectly joined to the promoter oligonucleotide;
   (b) contacting said at least two target capture oligomers in step (a) with a solid support and immobilized probe for performing a target capture;
   (c) washing said sample after target capture;
   (d) pre-amplifying said target nucleic acid sequences using said amplification oligomer complexes, under conditions configured to maintain the amplification oligomer complexes, thereby generating first amplification products for each target nucleic acid hybridized by an amplification oligomer complex;

(e) splitting said pre-amplified sample into at least two separate secondary target specific amplification reactions;

(f) amplifying at least two of said pre-amplified samples generated in step (d) using target specific amplification oligomers that are not joined, thereby generating second amplification products.

2. The method of claim 1, wherein the non-promoter primer oligonucleotide is joined to the promoter oligonucleotide via:

a direct hybridization (DH) complex between a first sequence in the non-promoter primer oligonucleotide and a second sequence in the promoter oligonucleotide that is complementary to the first sequence in the non-promoter primer oligonucleotide;

a hybridization complex comprising an S-oligonucleotide, wherein the S-oligonucleotide contains a first sequence complementary to a sequence in the promoter oligonucleotide and a second sequence complementary to a sequence in the non-promoter primer oligonucleotide; or a non-nucleotide linker.

3. The method of claim 2, wherein the non-promoter primer oligonucleotide is joined to the promoter oligonucleotide via the DH complex.

4. The method of claim 3, wherein the first and second sequences of the DH complex are a 5' sequence in the non-promoter primer oligonucleotide that is complementary to all or a portion of the promoter sequence in the promoter oligonucleotide.

5. The method of claim 1, wherein the amplifying reaction at step (f) is a quantitative amplification reaction whereby an amplification product is detected during the amplification reaction.

6. The method of claim 1, wherein the amplifying reaction at step (f) is an exponential amplification reaction.

7. The method of claim 1, wherein the amplification reaction at step (f) is accomplished using a substantially isothermal amplification reaction.

8. The method of claim 1, wherein a first amplification product generated in step (b) for a target nucleic acid hybridized by an amplification oligomer complex is from 100 to 10000 RNA transcripts.

9. The method of claim 1, where the first amplification products generated at step (d) are divided into a number of secondary target specific amplification reactions that equals the number of different amplification oligomer complexes used in step (a).

10. The method of claim 1, wherein the amplification oligomer complexes are formed before being added into the pre-amplifying reaction at step (d).

11. The method of claim 1, wherein the amplification oligomer complexes are formed and then added into a target capture reaction mixture at step (a).

12. The method of claim 1, wherein the amplification oligomer complexes are formed under hybridizing conditions during step (a).

13. The method of claim 1, wherein the pre-amplifying reaction at step (d) further comprises using a blocker oligomer.

14. The method of claim 1, further comprising detecting the second amplification products generated at step (f).

15. The method of claim 14, wherein the second amplification products are detected using a probe-based detection step.

16. The method of claim 15, wherein the probe-based detection step is a real-time detection step.

17. The method of claim 16, wherein the second amplification products are detected using a detection probe oligomer selected from the group consisting of a molecular beacon, a molecular torch, and a hybridization switch probe.

18. The method of claim 14, wherein the second amplification products are detected using a detection probe oligomer, mass spectrometry, nucleic acid sequencing, or gel electrophoresis.

19. The method of claim 1, wherein each of the amplification oligomer complexes hybridizes to a different region on the same target nucleic acid.

20. The method of claim 1, wherein each of the amplification oligomer complexes hybridizes to a different target nucleic acid.

* * * * *

SEQUENCE LISTING

<160> NUMBER OF SEQ ID NOS: 116

<210> SEQ ID NO 1
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 1
aatttaatac gactcactat agggagagtt tgtatgtctg ttgctattat gtctagtcta      60
cgtgtgtgct ttgtacgcac      80

<210> SEQ ID NO 2
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 2
aatttaatac gactcactat agggagagtt tgtatgtctg ttgctattat gtctaatcta     60
cttgtgtgct ctgtacacac                                                80

<210> SEQ ID NO 3
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 3
aatttaatac gactcactat agggagagtt tgtatgtctg ttgctattat gtctacgcct     60
cacatttaca acaggacg                                                  78

<210> SEQ ID NO 4
<211> LENGTH: 77
<212> TYPE: DNA
<213> ORGANISM: Artificial Sequence
<220> FEATURE:
<223> OTHER INFORMATION: Synthetic Oligonucleotide

<400> SEQUENCE: 4
aatttaatac gactcactat agggagagtt tgtatgtctg ttgctattat gtctacaatg     60
tagtaattag ctgtggc                                                   77

<210> SEQ ID NO 5
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 5
aatttaatac gactcactat agggagagtt tgtatgtctg ttgctattat gtctagcaca     60
ccacggacac acaaagga                                                  78

<210> SEQ ID NO 6
<211> LENGTH: 82
<212> TYPE: DNA
<213> ORGANISM: Artificial Sequence
<220> FEATURE:
<223> OTHER INFORMATION: Synthetic Oligonucleotide

<400> SEQUENCE: 6
aatttaatac gactcactat agggagagtt tgtatgtctg ttgctattat gtctaggata     60
gtgtgtccat aaacagctgc tg                                             82

<210> SEQ ID NO 7
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 7
aatttaatac gactcactat agggagagtt tgtatgtctg ttgctattat gtctaccgtc    60
tggctagtag ttgatg                                                    76

<210> SEQ ID NO 8
<211> LENGTH: 78
<212> TYPE: DNA
<213> ORGANISM: Artificial Sequence
<220> FEATURE:
<223> OTHER INFORMATION: Synthetic Oligonucleotide

<400> SEQUENCE: 8
aatttaatac gactcactat agggagagtt tgtatgtctg ttgctattat gtctacggag    60
cttcaattct gtaacacg                                                  78

<210> SEQ ID NO 9
<211> LENGTH: 79
<212> TYPE: DNA
<213> ORGANISM: Artificial Sequence
<220> FEATURE:
<223> OTHER INFORMATION: Synthetic Oligonucleotide

<400> SEQUENCE: 9
aatttaatac gactcactat agggagagtt tgtatgtctg ttgctattat gtctacgtat    60
gttgtttagc ttgtctagc                                                 79

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
gtgacagctc agatgaggat g                                              21

<210> SEQ ID NO 11
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 11
cgacgagccg aaccac                                                    16

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 12
gaccttgtat gtcacgagc                                                 19

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
gacagctcag aggaggagga tg                                              22

<210> SEQ ID NO 14
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 14
acagcagtac aaatggcagg acagctcaga ggaggagg                             38

<210> SEQ ID NO 15
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 15
acagcagtac aaatggcagg tgacagctca gatgaggatg                           40

<210> SEQ ID NO 16
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 16
acagcagtac aaatggcagg acgagccgaa ccaca                                35

<210> SEQ ID NO 17
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 17
acagcagtac aaatggcagg acgagctgaa ccacagcgtc ac                        42

<210> SEQ ID NO 18
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 18
acagcagtac aaatggcagg accttgtatg tcacgagc                             38

<210> SEQ ID NO 19
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 19
acagcagtac aaatggcagg acagctcaga ggaggaggat g                         41

<210> SEQ ID NO 20
<211> LENGTH: 23
<212> TYPE: RNA

```
<213> ORGANISM: Artificial Sequence
<220> FEATURE:
<223> OTHER INFORMATION: Synthetic Oligonucleotide

<400> SEQUENCE: 20
cagcuggaca agcagaaccg gac                                               23

<210> SEQ ID NO 21
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 21
ggccagaugg acaagcacaa c                                                 21

<210> SEQ ID NO 22
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 22
guaguagaaa gcucagcaga cgacc                                             25

<210> SEQ ID NO 23
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 23
gaccuuagaa cacuacagca gc                                                22

<210> SEQ ID NO 24
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 24
gauugcgagc cuuacagcag cug                                               23

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 25
ccgaccatgc agttaatcac c                                                 21

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 26
gcgtgaccag ctaccagaaa g                                                 21
```

<210> SEQ ID NO 27
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 27
gccacagcaa gctagacaag c                                           21

<210> SEQ ID NO 28
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 28
gcucauaaca guggagguca guugccuctt taaaaaaaaa aaaaaaaaa aaaaaaaaa    60 a                                                                  61

<210> SEQ ID NO 29
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 29
acagcgcccu gcccaacgac cctttaaaaa aaaaaaaaaa aaaaaaaaaa aaaaa       55

<210> SEQ ID NO 30
<211> LENGTH: 62
<212> TYPE: DNA
<213> ORGANISM: Artificial Sequence
<220> FEATURE:
<223> OTHER INFORMATION: Synthetic Oligonucleotide

<400> SEQUENCE: 30
gugcacagau cagguagcuu guagggucgt ttaaaaaaaa aaaaaaaaaa aaaaaaaaaa  60
aa                                                                 62

<210> SEQ ID NO 31
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 31
gcacaggucu ggcaauuugu auggccgttt aaaaaaaaaa aaaaaaaaaa aaaaaaaaaa  60

<210> SEQ ID NO 32
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 32
ggucuuugac aucugugaca ccuuauttta aaaaaaaaa aaaaaaaaaa aaaaaaaa     59

<210> SEQ ID NO 33

<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 33
aatttaatac gactcactat agggagagtt tgtatgtctg ttgctattat gtcta    55

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
acagcagtac aaatggcag                                             19

<210> SEQ ID NO 35
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 35
tagacataat agcaacagac atacaaacct gccatttgta ctgctgtc             48

<210> SEQ ID NO 36
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 36
gtcatatgcg acgatctcag ccaggagatt cagcggggca tacggattct cacc      54

<210> SEQ ID NO 37
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 37
aatttaatac gactcactat agggagacca caacggtttt ctgccggtta gctggccacg    60
atatcaacta tttggc                                                    76

<210> SEQ ID NO 38
<211> LENGTH: 35
<212> TYPE: RNA
<213> ORGANISM: Artificial Sequence
<220> FEATURE:
<223> OTHER INFORMATION: Synthetic Oligonucleotide

<400> SEQUENCE: 38
gcagaagcuu ccugacuggc caaauccacu cagcc                           35

<210> SEQ ID NO 39
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 39
cugccaauuu uugagagaac acggcag                                27

<210> SEQ ID NO 40
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 40
gcagcacauc cgaccgcuug cuuuaaaaaa aaaaaaaaa aaaaaaaaaa aaaac    55

<210> SEQ ID NO 41
<211> LENGTH: 81
<212> TYPE: DNA
<213> ORGANISM: Artificial Sequence
<220> FEATURE:
<223> OTHER INFORMATION: Synthetic Oligonucleotide

<400> SEQUENCE: 41
tctccctata gtgagtcgta ttaaattgtc atatgcgacg atctcagcca ggagattcag    60
cggggcatac ggattctcac c                                            81

<210> SEQ ID NO 42
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 42
gtcatatgcg acgatctcag ctttgtctct aattgaccat gtc                    43

<210> SEQ ID NO 43
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 43
aatttaatac gactcactat agggagacca caacggtttc aaggaagtga caatagatta    60
tataggc                                                            67

<210> SEQ ID NO 44
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 44
cuauugucac uuccuugagu auc                                    23

<210> SEQ ID NO 45
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 45

```
ccacuugcga uguuuuaagu gg                                           22
```

<210> SEQ ID NO 46
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 46

```
cguucacuau uggucucugc auucuuuaaa aaaaaaaaaa aaaaaaaaaa aaaaaac     57
```

<210> SEQ ID NO 47
<211> LENGTH: 70
<212> TYPE: DNA
<213> ORGANISM: Artificial Sequence
<220> FEATURE:
<223> OTHER INFORMATION: Synthetic Oligonucleotide

<400> SEQUENCE: 47

```
tctccctata gtgagtcgta ttaaattgtc atatgcgacg atctcagctt tgtctctaat  60
tgaccatgtc                                                         70
```

<210> SEQ ID NO 48
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 48

```
gtcatatgcg acgatctcag ggctcatcga tgacccaaga tggcggc                47
```

<210> SEQ ID NO 49
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 49

```
ggctcatcga tgacccaaga tggcggc                                      27
```

<210> SEQ ID NO 50
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 50

```
aatttaatac gactcactat agggagacca aacggtttt aatgtctaag tagtgacatg   60
tttc                                                               64
```

<210> SEQ ID NO 51
<211> LENGTH: 26
<212> TYPE: RNA
<213> ORGANISM: Artificial Sequence
<220> FEATURE:
<223> OTHER INFORMATION: Synthetic Oligonucleotide

<400> SEQUENCE: 51

```
ugucacuacu uagacauuau auuguc                                       26
```

```
<210> SEQ ID NO 52
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 52
cgcuuccugu gugugggua ugaagcg                                          27

<210> SEQ ID NO 53
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 53
aucuguuuuc cugcccaucc uuuaaguuua aaaaaaaaaa aaaaaaaaaa aaaaaaaa       59

<210> SEQ ID NO 54
<211> LENGTH: 74
<212> TYPE: DNA
<213> ORGANISM: Artificial Sequence
<220> FEATURE:
<223> OTHER INFORMATION: Synthetic Oligonucleotide

<400> SEQUENCE: 54
tctccctata gtgagtcgta ttaaattgtc atatgcgacg atctcagggc tcatcgatga    60
cccaagatgg cggc                                                     74

<210> SEQ ID NO 55
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 55
gtcatatgcg acgatctcag gctgtggctg acctgaaata cc                       42

<210> SEQ ID NO 56
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 56
gctgtggctg acctgaaata cc                                             22

<210> SEQ ID NO 57
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 57
aatttaatac gactcactat agggagacca caacggtttc cactgcatca ggaacaaaag    60
cgtgatcttg c                                                         71

<210> SEQ ID NO 58
<211> LENGTH: 24
<212> TYPE: RNA
```

<213> ORGANISM: Artificial Sequence
<220> FEATURE:
<223> OTHER INFORMATION: Synthetic Oligonucleotide

<400> SEQUENCE: 58
gaugcagugg gcagcuguga ggac                                    24

<210> SEQ ID NO 59
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 59
ugugucuuca ggaugaaaca caca                                    24

<210> SEQ ID NO 60
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 60
cgaacuugcg cacacacguc auuggattta aaaaaaaaaa aaaaaaaaaa aaaaaaaaac    60

<210> SEQ ID NO 61
<211> LENGTH: 69
<212> TYPE: DNA
<213> ORGANISM: Artificial Sequence
<220> FEATURE:
<223> OTHER INFORMATION: Synthetic Oligonucleotide

<400> SEQUENCE: 61
tctccctata gtgagtcgta ttaaattgtc atatgcgacg atctcaggct gtggctgacc    60
tgaaatacc                                                     69

<210> SEQ ID NO 62
<211> LENGTH: 557
<212> TYPE: DNA
<213> ORGANISM: Artificial Sequence
<220> FEATURE:
<223> OTHER INFORMATION: synthetic oligomer

<400> SEQUENCE: 62
tttaccatct gaggccacac atctgctgaa atggagataa ttaacatcac tagaaacagc    60
aagatgacaa tataatgtct aagtagtgac atgttttgc acatttccag cccctttaaa   120
tatccacaca cacaggaagc acaaaaggaa gcacagaggt aagtgcttta taaagcactc   180
aatttctact cagaaatttt tgatggcctt aagttcctct actcgtttct atccttccta   240
ctcactgtcc tcccggaatc cactaccgat tttctatttc ttgcctcgta ttgtctgact   300
ggctcacttg gatttatctc acggagtctg gattttctac ccgggctcac ctccgtccct   360
ccatatttgt cctccacttt cacagatccc tgggagaaat gcccggccgc catcttgggt   420
catcgatgag cctcgccctg tgcctggtcc cgcttgtgag ggaaggacat tagaaaatga   480
attgatgtgt tccttaaagg atgggcagga aaacagatcc tgttgtggat atttatttga   540
acgggattac agatttg                                           557

<210> SEQ ID NO 63
<211> LENGTH: 30

```
<212> TYPE: DNA
<213> ORGANISM: Artificial Sequence
<220> FEATURE:
<223> OTHER INFORMATION: Synthetic Oligonucleotide

<400> SEQUENCE: 63
atgtccaagt gtcatatgcg acgatctcag                                    30

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
gtcatatgcg acgatctcag                                               20

<210> SEQ ID NO 65
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 65
aatttaatac gactcactat agggagacca caacggtttc                         40

<210> SEQ ID NO 66
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 66
ctgagatcgt cgcatatgac aaaccgttgt ggtctcccta tac                     43

<210> SEQ ID NO 67
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 67
aatttaatac gactcactat agggaga                                       27

<210> SEQ ID NO 68
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 68
gaaattaata cgactcacta tagggaga                                      28

<210> SEQ ID NO 69
<211> LENGTH: 54
<212> TYPE: DNA
<213> ORGANISM: Artificial Sequence
<220> FEATURE:
<223> OTHER INFORMATION: Synthetic Oligomer

<400> SEQUENCE: 69
```
gcagcacauc cgaccgcuug cuuuaaaaaa aaaaaaaaaa aaaaaaaaaa aaaa    54

<210> SEQ ID NO 70
<211> LENGTH: 34
<212> TYPE: RNA
<213> ORGANISM: Artificial Sequence
<220> FEATURE:
<223> OTHER INFORMATION: Synthetic oligomer

<400> SEQUENCE: 70
gcagaagcuu ccugacuggc caaauccacu cagc    34

<210> SEQ ID NO 71
<211> LENGTH: 81
<212> TYPE: DNA
<213> ORGANISM: Artificial Sequence
<220> FEATURE:
<223> OTHER INFORMATION: synthetic oligomer

<400> SEQUENCE: 71
tctccctata gtgagtcgta ttaaattgtc atatgcgacg atctcagcca ggagattcag    60
cggggcatac ggattctcac c    81

<210> SEQ ID NO 72
<211> LENGTH: 75
<212> TYPE: DNA
<213> ORGANISM: Artificial Sequence
<220> FEATURE:
<223> OTHER INFORMATION: synthetic oligomer

<400> SEQUENCE: 72
aatttaatac gactcactat agggagacca caacggtttt ctgccggtta gctggccacg    60
atatcaacta tttgg    75

<210> SEQ ID NO 73
<211> LENGTH: 34
<212> TYPE: DNA
<213> ORGANISM: Artificial Sequence
<220> FEATURE:
<223> OTHER INFORMATION: synthetic oligomer

<400> SEQUENCE: 73
ccaggagatt cagcggggca tacggattct cacc    34

<210> SEQ ID NO 74
<211> LENGTH: 27
<212> TYPE: RNA
<213> ORGANISM: Artificial Sequence
<220> FEATURE:
<223> OTHER INFORMATION: synthetic oligomer

<400> SEQUENCE: 74
cugccaauuu uugagagaac acggcag    27

<210> SEQ ID NO 75
<211> LENGTH: 57
<212> TYPE: DNA
<213> ORGANISM: Artificial Sequence
<220> FEATURE:
<223> OTHER INFORMATION: synthetic oligomer

<400> SEQUENCE: 75
cguucacuau uggucucugc auucuuuaaa aaaaaaaaaa aaaaaaaaaa aaaaaaa    57

```
<210> SEQ ID NO 76
<211> LENGTH: 22
<212> TYPE: RNA
<213> ORGANISM: Artificial Sequence
<220> FEATURE:
<223> OTHER INFORMATION: synthetic oligomer

<400> SEQUENCE: 76
cuauugucac uuccuugagu au                                              22

<210> SEQ ID NO 77
<211> LENGTH: 70
<212> TYPE: DNA
<213> ORGANISM: Artificial Sequence
<220> FEATURE:
<223> OTHER INFORMATION: Synthetic Oligomer

<400> SEQUENCE: 77
tctccctata gtgagtcgta ttaaattgtc atatgcgacg atctcagctt tgtctctaat     60
tgaccatgtc                                                            70

<210> SEQ ID NO 78
<211> LENGTH: 67
<212> TYPE: DNA
<213> ORGANISM: Artificial Sequence
<220> FEATURE:
<223> OTHER INFORMATION: synthetic oligomer

<400> SEQUENCE: 78
aatttaatac gactcactat agggagacca caacggttta atagattata taggacgaca     60
agtaaaa                                                               67

<210> SEQ ID NO 79
<211> LENGTH: 23
<212> TYPE: DNA
<213> ORGANISM: Artificial Sequence
<220> FEATURE:
<223> OTHER INFORMATION: synthetic oligomer

<400> SEQUENCE: 79
ctttgtctct aattgaccat gtc                                             23

<210> SEQ ID NO 80
<211> LENGTH: 22
<212> TYPE: RNA
<213> ORGANISM: Artificial Sequence
<220> FEATURE:
<223> OTHER INFORMATION: synthetic oligomer

<400> SEQUENCE: 80
ccacuugcga uguuuuaagu gg                                              22

<210> SEQ ID NO 81
<211> LENGTH: 58
<212> TYPE: DNA
<213> ORGANISM: Artificial Sequence
<220> FEATURE:
<223> OTHER INFORMATION: synthetic oligomer

<400> SEQUENCE: 81
aucuguuuuc cugcccaucc uuuaaguuua aaaaaaaaa aaaaaaaaa aaaaaaa          58

<210> SEQ ID NO 82
<211> LENGTH: 25
<212> TYPE: RNA
```

<213> ORGANISM: Artificial Sequence
<220> FEATURE:
<223> OTHER INFORMATION: synthetic oligomer

<400> SEQUENCE: 82
ugucacuacu uagacauuau auugu                                           25

<210> SEQ ID NO 83
<211> LENGTH: 74
<212> TYPE: DNA
<213> ORGANISM: Artificial Sequence
<220> FEATURE:
<223> OTHER INFORMATION: synthetic oligomer

<400> SEQUENCE: 83
tctccctata gtgagtcgta ttaaattgtc atatgcgacg atctcagggc tcatcgatga     60
cccaagatgg cggc                                                       74

<210> SEQ ID NO 84
<211> LENGTH: 63
<212> TYPE: DNA
<213> ORGANISM: Artificial Sequence
<220> FEATURE:
<223> OTHER INFORMATION: synthetic oligomer

<400> SEQUENCE: 84
aatttaatac gactcactat agggagacca caacggtttt aatgtctaag tagtgacatg     60
ttt                                                                   63

<210> SEQ ID NO 85
<211> LENGTH: 27
<212> TYPE: DNA
<213> ORGANISM: Artificial Sequence
<220> FEATURE:
<223> OTHER INFORMATION: synthetic oligomer

<400> SEQUENCE: 85
ggcucatcga tgacccaaga tggcggc                                         27

<210> SEQ ID NO 86
<211> LENGTH: 27
<212> TYPE: RNA
<213> ORGANISM: Artificial Sequence
<220> FEATURE:
<223> OTHER INFORMATION: synthetic oligomer

<400> SEQUENCE: 86
cgcuuccugu gugugggua ugaagcg                                          27

<210> SEQ ID NO 87
<211> LENGTH: 59
<212> TYPE: DNA
<213> ORGANISM: Artificial Sequence
<220> FEATURE:
<223> OTHER INFORMATION: synthetic oligomer

<400> SEQUENCE: 87
cgaacuugcg cacacacguc auuggattta aaaaaaaaaa aaaaaaaaaa aaaaaaaa        59

<210> SEQ ID NO 88
<211> LENGTH: 23
<212> TYPE: RNA
<213> ORGANISM: Artificial Sequence
<220> FEATURE:
<223> OTHER INFORMATION: synthetic oligomer

<400> SEQUENCE: 88
gaugcagugg gcagcuguga gga                                              23

<210> SEQ ID NO 89
<211> LENGTH: 69
<212> TYPE: DNA
<213> ORGANISM: Artificial Sequence
<220> FEATURE:
<223> OTHER INFORMATION: synthetic oligomer

<400> SEQUENCE: 89
tctccctata gtgagtcgta ttaaattgtc atatgcgacg atctcaggct gtggctgacc      60
tgaaatacc                                                              69

<210> SEQ ID NO 90
<211> LENGTH: 70
<212> TYPE: DNA
<213> ORGANISM: Artificial Sequence
<220> FEATURE:
<223> OTHER INFORMATION: synthetic oligomer

<400> SEQUENCE: 90
aatttaatac gactcactat agggagacca caacggtttc cactgcatca ggaacaaaag      60
cgtgatcttg                                                             70

<210> SEQ ID NO 91
<211> LENGTH: 22
<212> TYPE: DNA
<213> ORGANISM: Artificial Sequence
<220> FEATURE:
<223> OTHER INFORMATION: synthetic oligomer

<400> SEQUENCE: 91
gcugtggctg acctgaaata cc                                               22

<210> SEQ ID NO 92
<211> LENGTH: 24
<212> TYPE: RNA
<213> ORGANISM: Artificial Sequence
<220> FEATURE:
<223> OTHER INFORMATION: synthetic oligomer

<400> SEQUENCE: 92
ugugucuuca ggaugaaaca caca                                             24

<210> SEQ ID NO 93
<211> LENGTH: 39
<212> TYPE: DNA
<213> ORGANISM: Artificial Sequence
<220> FEATURE:
<223> OTHER INFORMATION: synthetic oligomer

<400> SEQUENCE: 93
aatttaatac gactcactat agggagacca caacggttt                             39

<210> SEQ ID NO 94
<211> LENGTH: 20
<212> TYPE: DNA
<213> ORGANISM: Artificial Sequence
<220> FEATURE:
<223> OTHER INFORMATION: synthetic oligomer

<400> SEQUENCE: 94

```
gtcatatgcg acgatctcag                                               20
```

<210> SEQ ID NO 95
<211> LENGTH: 57
<212> TYPE: DNA
<213> ORGANISM: Artificial Sequence
<220> FEATURE:
<223> OTHER INFORMATION: synthetic oligomer

<400> SEQUENCE: 95

```
aatttaatac gactcactat agggagacca caacggtttt aatgtctaag tagtgac      57
```

<210> SEQ ID NO 96
<211> LENGTH: 74
<212> TYPE: DNA
<213> ORGANISM: Artificial Sequence
<220> FEATURE:
<223> OTHER INFORMATION: synthetic oligomer

<400> SEQUENCE: 96

```
tctccctata gtgagtcgta ttaaattgtc atatgcgacg atctcagggc tcatcgatga   60
cccaagatgg cggc                                                     74
```

<210> SEQ ID NO 97
<211> LENGTH: 65
<212> TYPE: DNA
<213> ORGANISM: Artificial Sequence
<220> FEATURE:
<223> OTHER INFORMATION: synthetic oligomer

<400> SEQUENCE: 97

```
tctccctata gtgagtcggt catatgcgac gatctcaggg ctcatcgatg acccaagatg   60
gcggc                                                               65
```

<210> SEQ ID NO 98
<211> LENGTH: 65
<212> TYPE: DNA
<213> ORGANISM: Artificial Sequence
<220> FEATURE:
<223> OTHER INFORMATION: synthetic oligomer

<400> SEQUENCE: 98

```
tctccctata gtgagtcggt catatgcgac gatctcaggg ctcatcgatg acccaagatg   60
gcggc                                                               65
```

<210> SEQ ID NO 99
<211> LENGTH: 68
<212> TYPE: DNA
<213> ORGANISM: Artificial Sequence
<220> FEATURE:
<223> OTHER INFORMATION: synthetic oligomer

<400> SEQUENCE: 99

```
tggtctccct atagtgagtc ggtcatatgc gacgatctca gggctcatcg atgacccaag   60
atggcggc                                                            68
```

<210> SEQ ID NO 100
<211> LENGTH: 69
<212> TYPE: DNA
<213> ORGANISM: Artificial Sequence
<220> FEATURE:
<223> OTHER INFORMATION: synthetic oligomer

<400> SEQUENCE: 100

```
gtggtctccc tatagtgagt cggtcatatg cgacgatctc agggctcatc gatgacccaa    60
gatggcggc                                                            69

<210> SEQ ID NO 101
<211> LENGTH: 66
<212> TYPE: DNA
<213> ORGANISM: Artificial Sequence
<220> FEATURE:
<223> OTHER INFORMATION: synthetic oligomer

<400> SEQUENCE: 101
ccgttgtggt ctccctatag tcatatgcga cgatctcagg gctcatcgat gacccaagat    60
ggcggc                                                               66

<210> SEQ ID NO 102
<211> LENGTH: 68
<212> TYPE: DNA
<213> ORGANISM: Artificial Sequence
<220> FEATURE:
<223> OTHER INFORMATION: synthetic oligomer

<400> SEQUENCE: 102
cttagacgtg gtctccctat agtcatatgc gacgatctca gggctcatcg atgacccaag    60
atggcggc                                                             68

<210> SEQ ID NO 103
<211> LENGTH: 69
<212> TYPE: DNA
<213> ORGANISM: Artificial Sequence
<220> FEATURE:
<223> OTHER INFORMATION: synthetic oligomer

<400> SEQUENCE: 103
cttagacatt ttgtggtctc ccgtcatatg cgacgatctc agggctcatc gatgacccaa    60
gatggcggc                                                            69

<210> SEQ ID NO 104
<211> LENGTH: 68
<212> TYPE: DNA
<213> ORGANISM: Artificial Sequence
<220> FEATURE:
<223> OTHER INFORMATION: synthetic oligomer

<400> SEQUENCE: 104
cttagaccgt tgtggtctcc cgtcatatgc gacgatctca gggctcatcg atgacccaag    60
atggcggc                                                             68

<210> SEQ ID NO 105
<211> LENGTH: 69
<212> TYPE: DNA
<213> ORGANISM: Artificial Sequence
<220> FEATURE:
<223> OTHER INFORMATION: synthetic oligomer

<400> SEQUENCE: 105
ctacttagac atgtggtctc ccgtcatatg cgacgatctc agggctcatc gatgacccaa    60
gatggcggc                                                            69

<210> SEQ ID NO 106
<211> LENGTH: 68
<212> TYPE: DNA
```

```
<213> ORGANISM: Artificial Sequence
<220> FEATURE:
<223> OTHER INFORMATION: synthetic oligomer

<400> SEQUENCE: 106
cactacttag acaggtctcc cgtcatatgc gacgatctca gggctcatcg atgacccaag      60
atggcggc                                                              68

<210> SEQ ID NO 107
<211> LENGTH: 70
<212> TYPE: DNA
<213> ORGANISM: Artificial Sequence
<220> FEATURE:
<223> OTHER INFORMATION: synthetic oligomer

<400> SEQUENCE: 107
cttagacatt aaaaccgttg tgggtcatat gcgacgatct cagggctcat cgatgaccca     60
agatggcggc                                                            70

<210> SEQ ID NO 108
<211> LENGTH: 65
<212> TYPE: DNA
<213> ORGANISM: Artificial Sequence
<220> FEATURE:
<223> OTHER INFORMATION: synthetic oligomer

<400> SEQUENCE: 108
gtggtctccc tatagtgagt catatgcgac gatctcaggg ctcatcgatg acccaagatg    60
gcggc                                                                65

<210> SEQ ID NO 109
<211> LENGTH: 60
<212> TYPE: DNA
<213> ORGANISM: Artificial Sequence
<220> FEATURE:
<223> OTHER INFORMATION: synthetic oligomer

<400> SEQUENCE: 109
gcagtggaaa ccgttgtggt catatgcgac gatctcaggc tgtggctgac ctgaaatacc    60

<210> SEQ ID NO 110
<211> LENGTH: 60
<212> TYPE: DNA
<213> ORGANISM: Artificial Sequence
<220> FEATURE:
<223> OTHER INFORMATION: synthetic oligomer

<400> SEQUENCE: 110
gtggtctccc tatagtgagt catatgcgac gatctcaggc tgtggctgac ctgaaatacc    60

<210> SEQ ID NO 111
<211> LENGTH: 64
<212> TYPE: DNA
<213> ORGANISM: Artificial Sequence
<220> FEATURE:
<223> OTHER INFORMATION: synthetic oligomer

<400> SEQUENCE: 111
gtcacttcct tgtggtctcc cgtcatatgc gacgatctca gctttgtctc taattgacca   60
tgtc                                                                 64

<210> SEQ ID NO 112
<211> LENGTH: 61
```

```
<212> TYPE: DNA
<213> ORGANISM: Artificial Sequence
<220> FEATURE:
<223> OTHER INFORMATION: synthetic oligomer

<400> SEQUENCE: 112
gtggtctccc tatagtgagt catatgcgac gatctcagct ttgtctctaa ttgaccatgt    60
c                                                                   61

<210> SEQ ID NO 113
<211> LENGTH: 51
<212> TYPE: DNA
<213> ORGANISM: Artificial Sequence
<220> FEATURE:
<223> OTHER INFORMATION: synthetic oligomer

<400> SEQUENCE: 113
kkkkkkkkkk kkkkkkkktt taaaaaaaaa aaaaaaaaaa aaaaaaaaaa a            51

<210> SEQ ID NO 114
<211> LENGTH: 50
<212> TYPE: DNA
<213> ORGANISM: Artificial Sequence
<220> FEATURE:
<223> OTHER INFORMATION: synthetic oligomer

<400> SEQUENCE: 114
tctccctata gtgagtcgta ttaaattcgt ggctggagtc atcacctggc              50

<210> SEQ ID NO 115
<211> LENGTH: 72
<212> TYPE: DNA
<213> ORGANISM: Artificial Sequence
<220> FEATURE:
<223> OTHER INFORMATION: synthetic oligomer

<400> SEQUENCE: 115
aatttaatac gactcactat agggagatat gaatgcgacc cggaacagct gcccactgca    60
tcaggaacaa aa                                                       72

<210> SEQ ID NO 116
<211> LENGTH: 45
<212> TYPE: DNA
<213> ORGANISM: Artificial Sequence
<220> FEATURE:
<223> OTHER INFORMATION: synthetic oligomer

<400> SEQUENCE: 116
aatttaatac gactcactat agggagatat gaatgcgacc cggaa                   45
```